(12) United States Patent
Farrish

(10) Patent No.: US 12,152,225 B2
(45) Date of Patent: Nov. 26, 2024

(54) ENHANCED MACROALGAL PHOTOBIOREACTOR, ALGAE SCRUBBER, AND SEAWEED CULTIVATOR METHODS AND APPARATUSES—RESERVOIR DRAIN STRUCTURES

(71) Applicant: Bryan Harold Farrish, South Salt Lake, UT (US)

(72) Inventor: Bryan Harold Farrish, South Salt Lake, UT (US)

( * ) Notice: Subject to any disclaimer, the term of this patent is extended or adjusted under 35 U.S.C. 154(b) by 0 days.

(21) Appl. No.: 18/368,174

(22) Filed: Sep. 14, 2023

(65) Prior Publication Data

US 2024/0026258 A1   Jan. 25, 2024

Related U.S. Application Data

(63) Continuation of application No. 16/848,779, filed on Apr. 14, 2020, now Pat. No. 11,814,612, which is a continuation of application No. 15/391,415, filed on Dec. 27, 2016, now Pat. No. 10,655,095.

(60) Provisional application No. 62/366,108, filed on Jul. 24, 2016, provisional application No. 62/357,987, filed on Jul. 2, 2016, provisional application No. 62/335,617, filed on May 12, 2016, provisional application No. 62/330,185, filed on May 1, 2016, provisional application No. 62/320,448, filed on Apr. 8, 2016, provisional application No. 62/316,945, filed on Apr. 1, 2016, provisional application No. 62/316,483, filed on Mar. 31, 2016, provisional application No. 62/271,947, filed on Dec. 28, 2015.

(51) Int. Cl.
*C12M 1/00* (2006.01)
*A01G 33/00* (2006.01)

(52) U.S. Cl.
CPC ............ *C12M 21/02* (2013.01); *A01G 33/00* (2013.01); *Y02A 40/80* (2018.01)

(58) Field of Classification Search
None
See application file for complete search history.

(56) References Cited

U.S. PATENT DOCUMENTS

| 5,097,795 | A | 3/1992 | Adey |
| 11,629,082 | B1 | 4/2023 | Johnson |
| 2017/0013810 | A1 | 1/2017 | Grabell |
| 2017/0055474 | A1 | 3/2017 | Storey |
| 2017/0127656 | A1* | 5/2017 | Bee .......................... C12M 1/002 |

(Continued)

FOREIGN PATENT DOCUMENTS

WO   WO-2013138201 A1 *  9/2013  ............. A01G 33/00

OTHER PUBLICATIONS

Mullins, Algae turf scrubber—how to remove algae, 2012, retrieved from https://mullinsfarms.com/misc/algae-turf-scrubbers/.

(Continued)

*Primary Examiner* — Holly Kipouros

(57) ABSTRACT

Apparatuses and methods for reducing cost and space requirements and increasing ease of cleaning/harvesting of algae scrubbers and seaweed cultivators by utilizing illumination domes, macroalgal settlement structures, reservoirs including overflowing and pole mount, repositionable water outlet structures, 3D printed macroalgal attachment materials, and submersible macroalgal illumination devices.

20 Claims, 22 Drawing Sheets

(56) References Cited

U.S. PATENT DOCUMENTS

2017/0332568 A1  11/2017  Storey

OTHER PUBLICATIONS

Carlson, Turbo HF/Rev 3 Algae Scrubber from Turbo's Aquatics (720p) [video], Jun. 26, 2014, retrieved from https://www.youtube.com/watch?v=BTZMmU4tiqE.

* cited by examiner (Previous Art)**

(Previous Art)

(Previous Art)

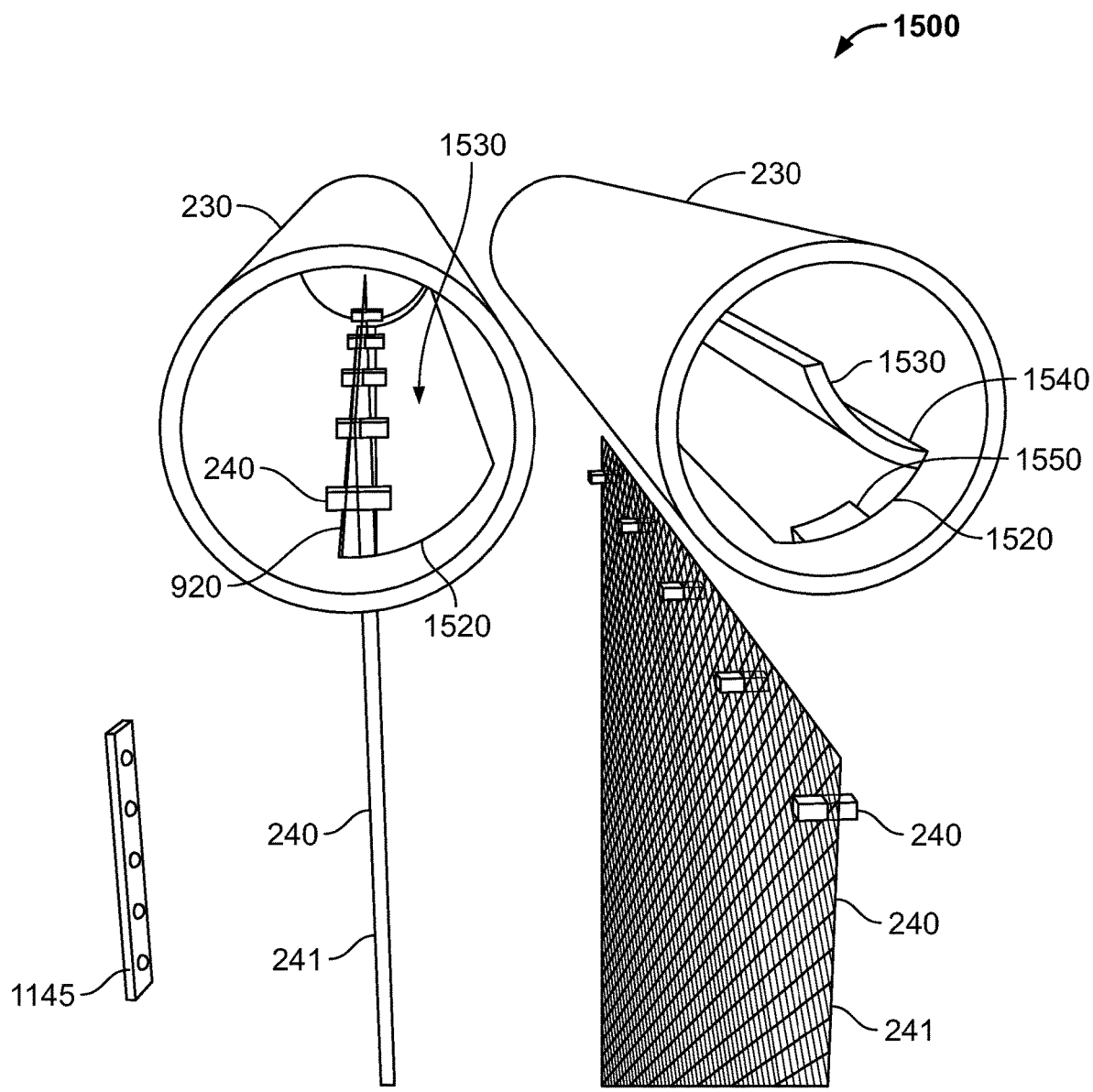
FIG. 15A  FIG. 15B

(Previous Art)

ENHANCED MACROALGAL PHOTOBIOREACTOR, ALGAE SCRUBBER, AND SEAWEED CULTIVATOR METHODS AND APPARATUSES—RESERVOIR DRAIN STRUCTURES

CROSS-REFERENCE TO RELATED APPLICATIONS

This U.S. utility patent application is a continuation of pending U.S. application Ser. No. 16/848,779 filed Apr. 14, 2020, which claims priority to U.S. provisional application 62/366,108 filed Jul. 24, 2016, U.S. provisional application 62/357,987 filed Jul. 2, 2016, U.S. provisional application 62/335,617 filed on May 12, 2016, U.S. provisional application 62/330,185 filed May 1, 2016, U.S. provisional application 62/320,448 filed Apr. 8, 2016, U.S. provisional application 62/316,945 filed Apr. 1, 2016, U.S. provisional application 62/316,483 filed Mar. 31, 2016, and U.S. provisional application 62/271,947 filed Dec. 28, 2015.

FIELD

An embodiment of the invention the generally relates to a mounting system for a waterfall style algae scrubber or waterfall style seaweed cultivator, enabling the construction to be made of fewer materials and components and the operation to be facilitated in a reduced space, an algae scrubber being an apparatus that uses illumination, rough surfaces, and a turbulent air/water interface to purposely grow attached macroalgae on the rough surfaces such that the growth of this macroalgae removes or "scrubs" nutrients out of the water. Another embodiment generally relates to an improved submersible algal growth illumination device. Another embodiment generally relates to 3D printed algal attachment materials. Other embodiments are also described and are divided into pertinent paragraphs with example claims.

BACKGROUND

Many industries such as aquaria, aquaculture, wastewater, and pool and spa rely on "clean" water for their proper operation. In these industries, "clean" is defined as water that is low in nutrients (e.g. Inorganic Nitrate, Inorganic Phosphate, Nitrite, Ammonia, Ammonium, and metals such as Copper). These nutrients cause problems in water such as excessive algae and bacteria growth, and in some cases, poisoning of livestock. In these instances, algae disperse in the water in an uncontrolled manner thereby making algae removal difficult. Thus in these industries there is a desire to remove nutrients and associated algae from the water in order to maintain "clean" water.

Despite the desire to remove nutrients and algae from water for certain applications, many industries rely on the presence of nutrients in the water for success. For example, food and biofuel industries grow algal biomass to produce their final products. This algal biomass requires a constant supply of nutrients to grow. Seaweed cultivators both filter the water of nutrients to provide clean water, and promote controlled growth of algal biomass such that the algae can be easily and efficiently harvested or otherwise removed from the water.

The rapid growth of attached macroalgae in either a filtering or cultivating application requires a turbulent air/water interface to maximize the nutrient transfer into the algae, which in the case of a waterfall is accomplished by gravity pulling a thin layer of water down a rough algal attachment surface; this requires the waterfall to be above a surrounding water surface level. A support structure for previous art waterfalls was needed to suspend the algae scrubber device above the surrounding water surface level; the support and waterfall were large and heavy because of the jolting movement of the water supply source tubing and the weight of the algal growth that was pulling downwards. Furthermore, illumination devices were in close proximity to algal attachment surfaces and had to be water resistant and heat sinked, which made them heavy and bulky also and thus requiring a more substantial frame or support. This added frame and bulk usually sat on a shelf in a sump beneath an aquarium, and provided limited access to the algae attachment surface for observation or cleaning/harvesting. Further, the entire structure of the waterfall, attached illumination devices, and water supply tubing usually took the majority of the open air space above the sump and therefore limited or eliminated access to the water below it. Thus there is a need for a simpler and space saving mounting and water delivery system for waterfall algae scrubbers and waterfall seaweed cultivators.

The illumination that drives the photosynthetic growth of the seaweed can be supplied by natural or artificial means. Light emitting diodes (LEDs) and similar artificial illumination emitters are commonly used, however they produce heat and require protection from water, especially saltwater. Common "plant-grow" hydroponic illumination units are readily available which are water resistant and even waterproof, however they usually are constructed with at least part of the enclosure being made of metal or a partially metallic material. Other waterproof illumination devices such as used for pools or boating also seal the illumination emitter from the water, but similar to hydroponic illumination units they do not protect the water itself from the metals, nor do they need to. These metals, if in continuous contact with saltwater, may slightly or rapidly corrode, and may cause serious damage to reef aquaria invertebrates. Even stainless steel is preferred to not be used. Invertebrates are very susceptible to small amounts of certain metals, and even the slightest trace of copper will kill them. Thus there is a need for a submersible non-metallic illumination device which is compact and lightweight in order to reduce the size and complexity of waterfall algae scrubbers.

For both filtration and cultivation, attachment of the macroalgae to solid surfaces is needed, and the surfaces should be rough and porous to encourage this attachment. Current rough attachment surfaces however are complex to manufacture or laborious to make manually. Thus, there is a need for algae scrubber and seaweed cultivator macroalgal attachment materials which are lower in cost and easier to manufacture.

SUMMARY

Applicant's SURF, HOG, and DROP Scrubbers® are examples of algae scrubber devices which operate using an upflowing gas bubble method, and applicant's RAIN™ algae scrubbers operates using a waterfall method. An embodiment of the current disclosure is directed towards waterfalls for supporting macroalgal attachment material and supplying water to a macroalgal attachment surface, and comprises a macroalgal attachment material that defines a macroalgal attachment surface; a reservoir structure that defines a reservoir top opening, a reservoir compartment and water outlet; and a macroalgal attachment material positioning mechanism to position the macroalgal attachment material substantially beneath the water outlet and to align the macroalgal attachment surface such that water flowing out of the water outlet contacts the macroalgal attachment surface.

Another embodiment of the current disclosure is for releasably supporting macroalgal attachment material and supplying water to a macroalgal attachment surface, and comprises a macroalgal attachment material defining a macroalgal attachment surface; a water delivery structure defining a water outlet border; a water outlet structure movable from a first position to a second position and which defines a portion of a water outlet when in the first position; and a positioning means which positions the water outlet structure in the first position abutting the water outlet border such that the macroalgal attachment material is secured substantially below the water outlet structure and water from the water outlet contacts the macroalgal attachment surface and further enables movement of the water outlet structure to the second position such that the macroalgal attachment material may be removed from the water delivery structure.

Another embodiment of the current disclosure is for supporting a structure which supports macroalgal attachment material and supplies water to a macroalgal attachment surface, and comprises a macroalgal attachment material defining a macroalgal attachment surface; a macroalgal settlement structure defining a macroalgal settlement surface; a water delivery structure which intersects a plane of the macroalgal settlement surface; a positioning mechanism to position the macroalgal attachment material such that the macroalgal attachment surface receives water from the water delivery structure; and an attachment mechanism to couple the macroalgal settlement structure to the water delivery structure and to align the macroalgal settlement surface such that macroalgae is enabled to travel from the macroalgal attachment surface to the macroalgal settlement surface.

Another embodiment of the current disclosure is for utilizing as much of a structure as possible in an overflowing manor, and comprises a reservoir structure defining a reservoir compartment, a water inlet, a water outlet; a macroalgal attachment material defining a macroalgal attachment surface; and an attachment mechanism to position the macroalgal attachment material such that water flowing out of the water outlet overflows down an external surface of the reservoir structure and makes contact with the macroalgal attachment surface.

Another embodiment of the current disclosure is for enclosing a waterfall algae scrubber or seaweed cultivator, and comprises an enclosure structure movable from a first position to a second position, the first position enclosing an algal attachment surface such that illumination from inside the structure is substantially prevented from traveling outside the structure, and the second position such that access to the algal attachment surface is substantially increased relative to the first position.

Another embodiment of the current disclosure is for illuminating macroalgal attachment surfaces under or above water, and comprises an illumination emitter, a lens, and an overmold that is substantially thermally conductive, substantially electrically non-conductive, and substantially non-metallic, the overmold to position the lens to be in optical communication with the illumination emitter and to enable illumination and heat from the illumination emitter to travel to surrounding ambient air or water such that the apparatus can operate in ambient air or submerged in water without moisture or heat damage to the illumination emitter.

Another embodiment of the current disclosure is for 3D printed macroalgal attachment surfaces, and includes a macroalgal attachment material comprising a first sheet of polymer having a top surface and a bottom surface, with a plurality of lumps positioned on the top surface whereby the lumps provide attachment surfaces for freshwater and saltwater macroalgae. The lumps extend 1-5 mm out from the top surface, and are 1-5 mm in diameter each. Each lump has a hairline thread extending from it, and all hairline threads are substantially in a uniform direction and non-touching so as to allow comb-harvesting, or are in a non-uniform direction and are touching so as to enable slime algae to attach better. The material is PETG, and is attached to a second sheet of material so as to have lumps on both sides of the sheet for freshwater and saltwater macroalgae to attach to. The sheet of material also includes one or more grommets for attachment to a stationary object, and the grommets themselves have lumps on them so as to maximize algal attachment.

BRIEF DESCRIPTION OF THE DRAWINGS

The embodiments of the invention are illustrated by way of example and not by way of limitation in the figures of the accompanying drawings, in which like references indicate similar elements. It should be noted that references to "an" or "one" embodiment of the invention in this disclosure are not necessarily to the same embodiment, and they mean at least one.

FIG. 15A shows a perspective view of a screen-release embodiment in a water pipe, of the current invention.

FIG. 15B shows a perspective view of the screen-release embodiment of FIG. 15A, with the screen removed.

DETAILED DESCRIPTION

Figure 1:
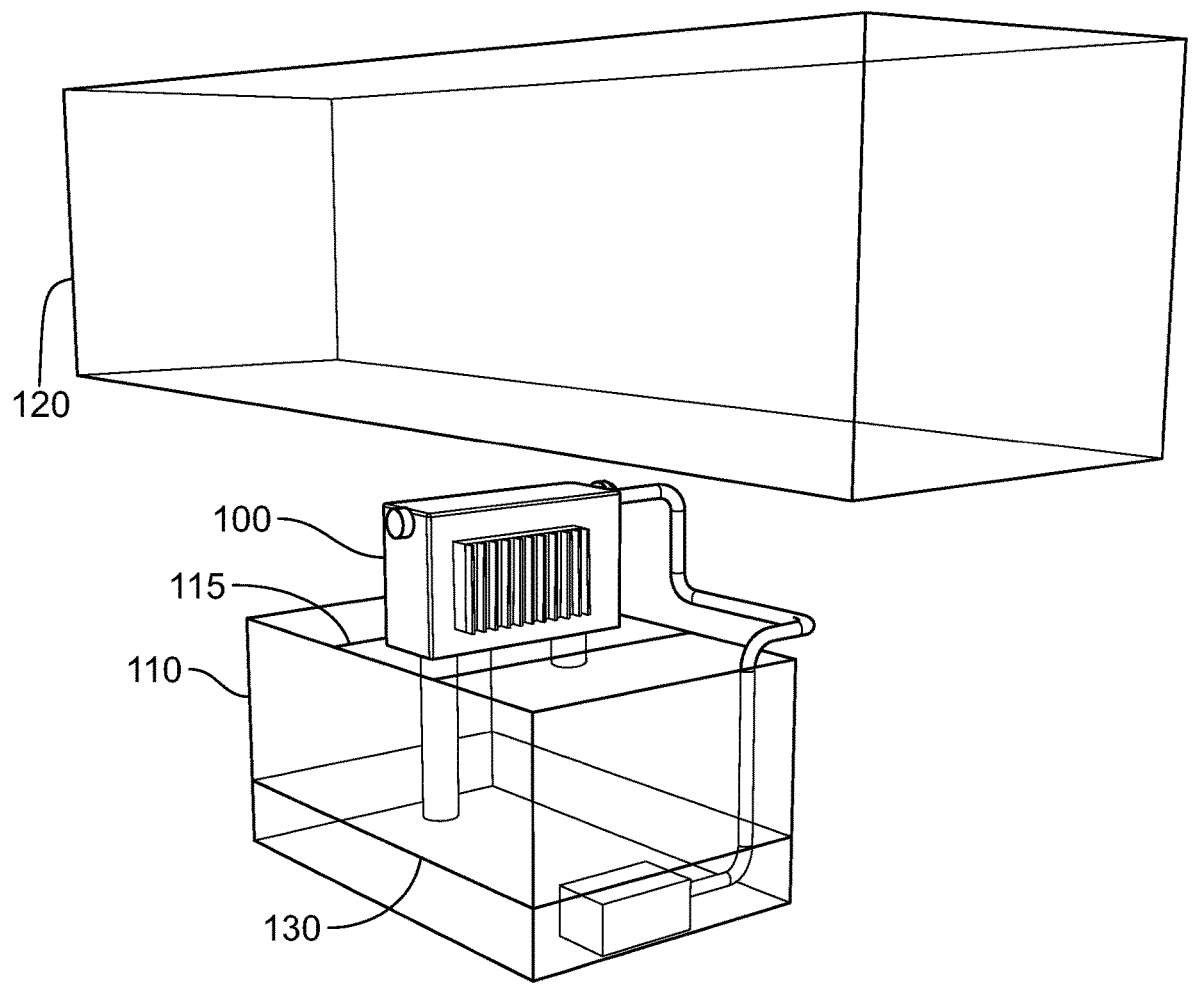
FIG. 1 shows a perspective view of a previous art waterfall algae scrubber designed in 2008, setting on a shelf in a sump beneath an aquarium.

Several embodiments of the invention with reference to the appended drawings are now explained. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

In the process of filtering water using algal filtration, the challenge has been how to grow algae easily so the algae can be removed or harvested, thus removing the nutrients from the water. If the algae are not removed they will simply die and put nutrients back into the water. For biomass growth and production, the challenge has been how to grow enough biomass, in a small space, quickly and cheaply. Algae, either for filtering or for production, fall into two main algae categories: uni-cellular and multi-cellular. Uni-cellular algae are microscopic organisms which drift freely in the water (e.g. plankton) and give the water a usually green tint. Therefore uni-cellular algae are usually called "micro" algae or "phyto" plankton. Multi-cellular algae are seaweeds that usually attach themselves to a surface. Since multi-cellular seaweeds are much larger than microalgae, they are usually called "macro" algae. It is these multi-cellular attached macroalgae seaweeds that are the focus of several of the embodiments described herein, and particularly in the descriptions below, care should be taken to observe whether the term used is microalgae or macroalgae because microalgae is a liquid that can be pumped or poured, whereas macroalgae is a solid that must be pulled or scraped.

PREVIOUS ART

The applicant's invention of the first waterfall version of an "algae scrubber" was in 2008 and was dedicated to the public domain, and has had tens of thousands of aquarists build and operate it successfully. The basic operation of a waterfall version "algae scrubber" is: Water flows down a rough surface such as a screen, and is illuminated on one or both sides of the screen. The combination of illumination, rough screen surfaces, turbulent air/water interfaces, and nutrients in the water cause algae to attach and grow on the screen thus removing nutrients from the water because the algae utilize these nutrients for growth. The algae is subsequently removed (harvested) so that the nutrients are removed also, thus completing the filtering function of the algae scrubber, or the cultivation function of the cultivator. Filtering and cultivation are the same chemical process, just described differently depending on the application; thus herein when an algae scrubber is described it also refers equally to a cultivator.

The applicant's subsequent invention of the gas bubble Upflow Algae Scrubber® (also identified as UAS®) version of an algae scrubber in 2011 (U.S. Pat. No. 9,115,008) with its companion gas bubble distribution system in 2013 (U.S. Pat. No. 9,334,184) was the opposite of a waterfall and allowed an algae scrubber or cultivator apparatus to be operated partially or completely submerged, thereby occupying little or no space above the water. This upflow design also eliminated any possibility of the algae drying out if water flow were stopped, because it was always submerged. It also could not overflow onto the floor if a drain clogged because it was already submerged and thus had no water draining. Many aquarium owners however still desire the original waterfall version if for no other reason than these designs have been around for a longer time, and these people have gone to great lengths to make space for the waterfalls to operate above the ambient water surface level in their sumps, and subsequently have tolerated overflows, drying out, water spray, large and heavy frames, and the hassles of disassembly and removal that are needed for cleaning/harvesting of these previous art waterfall designs.

Figure 10:
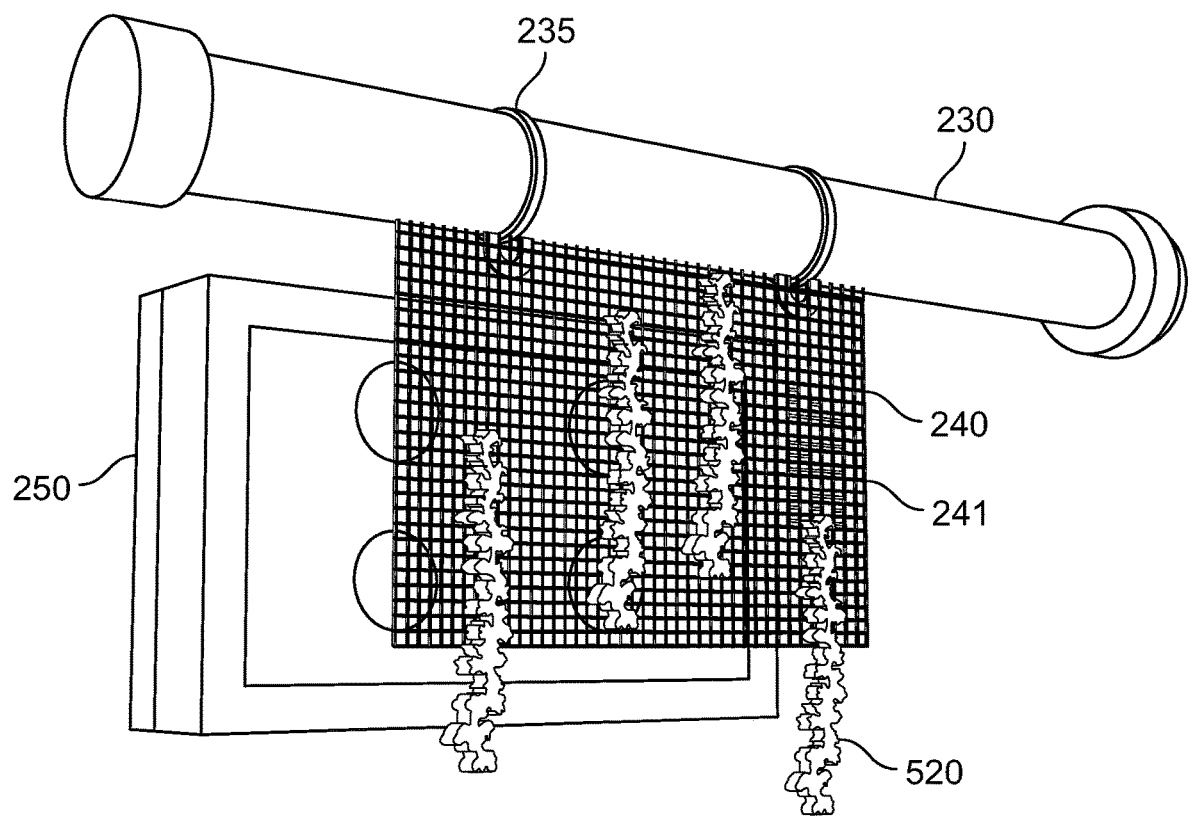
FIG. 10 shows a perspective view of components of a previous art waterfall algae scrubber designed in the year 2008.

FIG. 10 shows the basic functionality of the original previous art waterfall style "algae scrubber" as invented by the applicant and dedicated to the public domain in the year 2008. Water delivery structure 230, which was usually a PVC (polyvinylchloride) plumbing pipe 230, was fed by a water supply source (not shown). Pipe 230 had a slot (not shown) cut through its bottom side, and an algal attachment screen 240 with algal attachment surface 241 that was inserted up into this slot and held in place with screen attachment means 235 which was usually plastic tie-wraps 235. It is important to understand that screen 240 was not placed behind pipe 230 as it may appear in the drawing; screen 240 was instead inserted up into pipe 230 through a slot in the pipe. When water flowed into pipe 230 and then out of the slot, the water flowed down and stayed mostly in contact with attachment surface 241. This flowing turbulent water was illuminated on one or both sides by an illumination device 250 which was usually an LED or fluorescent bulb. Because the water came from an aquarium which had nutrients such an ammonia, ammonium, nitrite, nitrate, phosphate and CO2, photosynthetic algal growth 520 occurred which used these nutrients to grow and attach to surface 241. Cleaning/harvesting of the growth 520 (and thus nutrients) occurred by the user turning off the water supply source to pipe 230 and then removing the screen attachment means 235 and algal attachment screen 240 from water delivery structure 230; the growth 520 was then scraped off of surface 241 and discarded and screen 240 was replaced back into the slot of pipe 230 for more growth to occur.

FIG. 1 shows another previous art original waterfall algae scrubber 100 from the year 2008. These waterfalls designs were almost always positioned above a sump 110 where they sat on a shelf 115, and the sump itself was usually below a "display" aquarium 120. Water flowed from aquarium 120 down to sump 110 and was pumped back up to aquarium 120 using a pump and piping not shown. Many different things could be put into sump 110, however because algae scrubber 100 was a waterfall it needed to go above the ambient water surface level 130 of sump 110 so water could drain back down into sump 110. This placement not only blocked access to things that were kept in the water 130 of sump 110 but also blocked some access to the space above sump 110.

Figure 2:
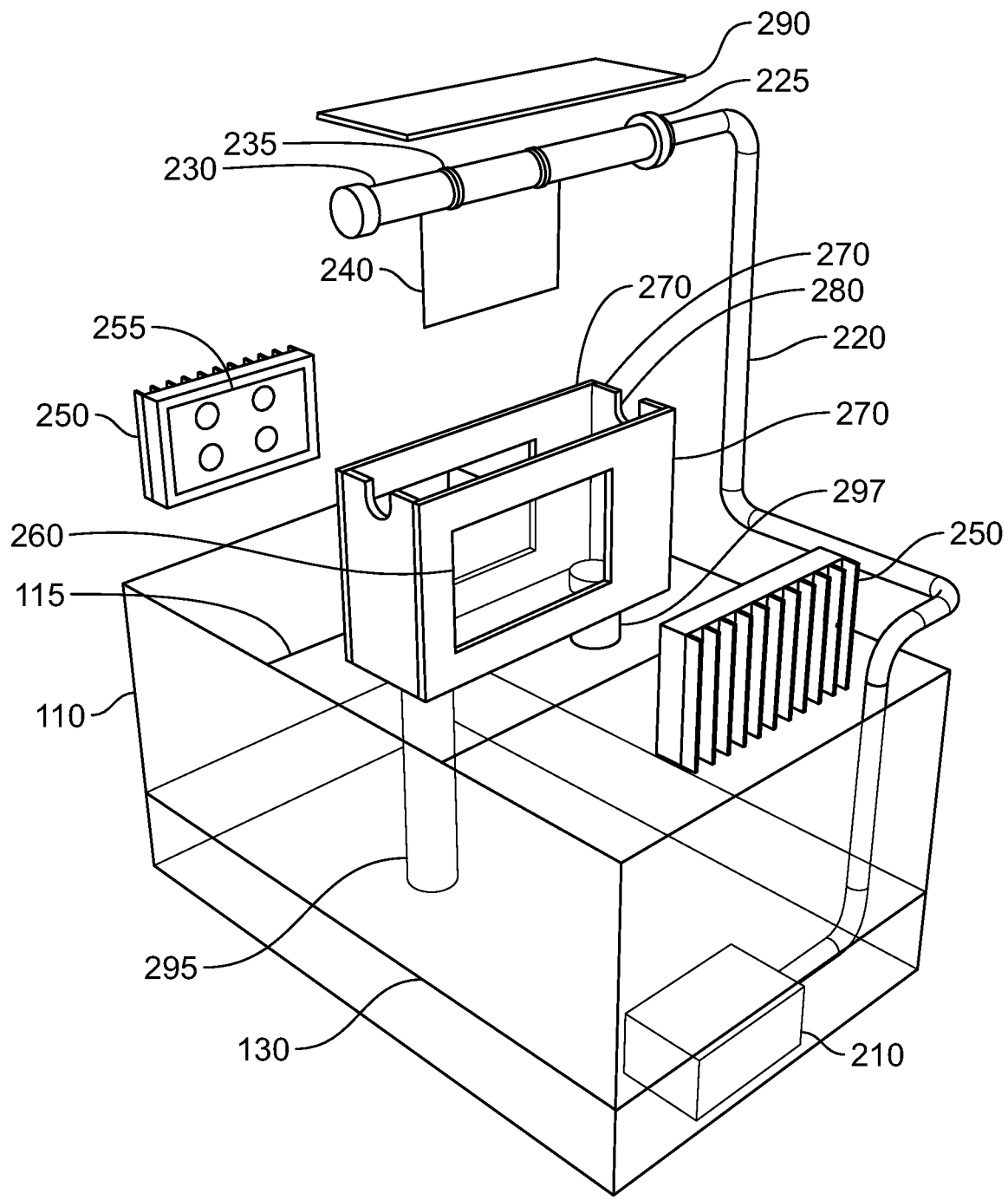
FIG. 2 shows a perspective view of the previous art waterfall algae scrubber of FIG. 1, exploded.

FIG. 2 shows an exploded view of the previous art algae scrubber 100 of FIG. 1. Water in sump 110 was pumped by water pump 210 through water source tubing 220, through coupler 225, until water reached water delivery structure 230 which here was a water pipe 230. Water then flowed out of an orifice slot (not shown) cut into the bottom of water pipe 230 and flowed down algal attachment screen 240 (held in place with screen attachment means 235) where the water was then illuminated by illumination devices 250. Illumination from illumination devices 250 traveled through illumination ports 260 which were built into the sides of water delivery support walls 270. Water delivery support walls 270 included cutouts 280 to hold water delivery pipe 230 in place during the starting and stopping of pump 210 because of the change of water pressure which tended to move water delivery pipe 230 laterally. Lid 290 held water delivery pipe 230 into cutouts 280 and also helped to contain illumination from escaping upwards. Water and sometimes algal growth flowed down drain pipe 295 to the ambient water surface level 130 below, and if pipe 295 became clogged with algal growth then secondary drain pipe 297 took over so that floods did not occur, because if water delivery support walls 270 filled up with water then an overflow would flow onto shelf 115 and then onto the ground of the room where the sump was located.

For cleaning/harvesting, lid 290 was removed and water delivery pipe 230 with water supply source tubing 220 was raised above water delivery support walls 270 in a similar fashion to this exploded drawing. Screen attachment means 235 were usually "zip ties" or "tie wraps" and were cut off, and the algal attachment screen 240 was then removed from the slot in water delivery pipe 230 and taken to a sink or elsewhere to be scraped clean of algal growth; the cleaned screen 240 was then replaced back into position in water delivery pipe 230, new screen attachment means 235 were added, pipe 230 was lowered back into locking position in cutouts 280 of water delivery support walls 270, and lid 290 was put back into position. Sometimes drain 295 or the interior area between water delivery support walls 270 would require a more thorough cleaning, and thus the entire algae scrubber would need to be lifted from shelf 115 and taken to a sink for disassembly, a process that could take several hours if there was encrusted lime/carbonate buildup that needed to be cleaned. The cleaning/harvesting process was typically repeated every 7 to 14 days.

Illumination devices 250 were protected from water by a transparent shield such as glass or acrylic over illumination ports 260, and were also somewhat protected by shelf 115 from water splashing up from the ambient water surface level 130. Illumination devices 250 might also have had a protective covering 255 directly over the illumination emitters. Illumination devices 250 had to be moved outwards as shown in this exploded view, or the algal attachment screen 240 had to be lifted upwards, in order to clean/harvest the growth on screen 240, or even to view the growth through illumination ports 260.

Because water delivery pipe 230 had to be held in position during operation, and because it supported all the weight of a fully grown and wet screen 240 in addition to water in pipe 230 itself, pipe 230 needed support from water delivery support walls 270. This was especially true because pipe 230 was connected to water source tubing 220 which sometimes had large volumes of water flowing, and when water pump 210 was turned on or off this hose 220 would jump or move around much like a garden hose when the water starts or stops. Thus support walls 270 of the structure were usually constructed of thick acrylic, usually black to contain illumination. Lid 290 sometimes was made very thick and heavy also, or had a locking feature, which prevented water delivery structure 230 from moving out of position should it be bumped accidentally. And since illumination devices 250 needed to illuminate through supporting walls 270, transparent acrylic windows 260 needed to be added, thus increasing cost and complexity because two types of acrylic needed to be fabricated together (black to stop illumination, and transparent to enable illumination) usually in a waterproof manner. This substantially solid, heavy, and fragile acrylic enclosure comprised the majority of the high cost of the waterfall designs, and was very difficult and expensive to ship.

Moving illumination devices 250 away from water delivery support walls 270 required that the illumination devices 250 themselves be self contained devices, sealed and protected from moisture and breakage, with a frame or attachment mechanism that had to be released before movement could occur. Similarly, moving algal attachment screen 240 upwards usually required that the entire water delivery source tubing 220 be lifted also, in which case water continued flowing out of the orifice slot of water delivery pipe 230 in no particular direction; or that coupler 225 be decoupled so that water delivery source tubing 220 could be disconnected from the water delivery pipe 230, but this required water pump 210 to be turned off so spraying would not occur out of the open end of water source tubing 220. Thus in this original previous art waterfall algae scrubber from the year 2008, any method of gaining access to the algal attachment screen 240 required substantial disassembly of different components, especially if the entire algae scrubber were to be lifted up and removed, and these components added to the complexity, space, and cost.

Besides the space occupied by the waterfall algae scrubber above ambient water surface level 130, other common complaints concerned the noise that the drain 295 made. Because illumination devices 250 were usually metallic, they had to be positioned far enough up above ambient water surface level 130 so no splashing water reached them. This elevated distance required drainage pipe 295 to be connected to the drain orifice (not shown) of the algae scrubber, and thus drainage pipe 295 was the source for relatively loud gurgling and surging as water drained rapidly out of the water delivery support walls 270. Further, when rapidly draining water impacted the ambient water surface level 130 below, many gas bubbles were produced in sump 110 which then circulated back to the display aquarium. Lastly, macroalgal growth tended to extend downward from attachment screen 240, subsequently piling up and attaching to the bottom of water delivery structure support walls 270. Thus when pipe 230 and screen 240 were lifted up for cleaning, macroalgae was torn apart from the bottom of support walls 270 and this caused clumps of algae to fall into sump 110 where the algae then circulated back to the display aquarium. Large portions of algae also sometimes fell onto the ground. As of October 2016, this method of constructing "enclosed" style waterfall algae scrubbers that the applicant dedicated to the public domain in 2008 is still the standard, and thus no low cost enclosed versions have been available.

Definitions

Algae Scrubber: An apparatus that uses illumination, rough surfaces, and a turbulent air/water interface to purposely grow attached macroalgae on the rough surfaces; the growth of this macroalgae removes or "scrubs" nutrients out of the water. Although algae had been utilized previously to consume nutrients from water, it was Walter Adey's U.S. Pat. No. 4,333,263 in the year 1980 that described how to utilize a turbulent air/water interface to greatly increase the rate of the algal growth; the turbulence removed the invisible boundary layer around the algae, and this allowed nutrients to enter the algae faster. The main differences in the types of algae scrubbers since then have centered on how to provide the turbulent air/water interface, and how to provide convenient placement and cleaning.

Waterfall Algae Scrubber: A version of an algae scrubber that generates the turbulent air/water interface by utilizing a cascade of water down a substantially vertical algae-attachment surface. This version of the algae scrubber was invented by the applicant in 2008 and was dedicated to the public domain. It is the opposite of upflow style gas bubble algae scrubbers as described in applicant's U.S. Pat. No. 9,115,008. For the purposes of the present application, waterfalls can also include any algae scrubber design that utilizes gravity to pull water down across the algal attachment surface, and thus requires placement above the ambient water surface level; such designs might include sloped-river designs, and dumping-bucket designs, although the applicant did not invent these.

Macroalgal Attachment Material: A material, including any mounting component, which is disposed in or on an algae scrubber and which has at least one rough macroalgal attachment surface to increases the ability of macroalgae to attach and grow on. This material, and any mounting component, might be removed from the algae scrubber in order to scrape, clean, or otherwise harvest macroalgal growth from the macroalgal attachment surface, or the material might be scraped, cleaned, or otherwise harvested in-place while still disposed in or on the algae scrubber apparatus.

Enclosure Structure: The totality of components that partially or wholly surrounds a waterfall algal attachment surface and also possibly a waterfall water delivery structure, such that illumination, water spray, and algal growth are substantially contained within the enclosure. In the current application an enclosure structure comprises at least a dome, the dome actually being any suitable shape. An enclosure structure is wholly or partially removable or repositionable so as to enable substantial access to an algal attachment surface for observation and cleaning/harvesting.

Dome: A removable or repositionable portion of an enclosure structure which substantially encloses an algal attachment surface and also possibly a water delivery structure. A dome has an external surface and a concave internal surface, and it may be substantially opaque, and may have illumination devices on its external or internal surface. A dome may substantially rest upon an algal settlement structure, in which case when the dome is removed or repositioned the algal settlement structure remains stationary.

Illumination Substantially Reduced: A low enough level of illumination lux traveling from inside an enclosure structure to outside the enclosure structure such that a user can comfortably perform duties in an around the sump area without the illumination causing visual difficulties for the user. Common lux reduction values are 50% to 100%.

Access Substantially Increased: A high enough level of access to an algal attachment surface to enable a user to observe growth on the algal attachment surface and also to physically clean/harvest the majority of growth from the algal attachment surface without needing to remove or reposition the attachment material relative to the apparatus, aquarium or sump where the apparatus is located. In other words, substantial access allows in-place harvesting of growth without having to move many things.

Headspace: The open space above the water surface level in a reservoir compartment. The top of the reservoir compartment may have a lid, however the lid is generally not air tight and thus allows the level of the water (and air) to vary up and down in the compartment. Headspace can be visualized by filling a bowl halfway with water; the unfilled upper portion of the bowl is the headspace.

Reservoir Structure: A structure defining a reservoir compartment, a water inlet to the compartment, and a water outlet structure further defining a water outlet from the compartment. The reservoir compartment itself may function as the water outlet structure. A reservoir structure enables the flow of water through the reservoir compartment from the inlet to the outlet, and the outlet may be coupled to a water delivery structure which delivers water to an algal attachment surface, or the reservoir structure may itself be a water delivery structure to an algal attachment surface; the reservoir structure may also be all or part of the physical support structure of the waterfall algae scrubber apparatus. Depending on the dimensions and shape of a reservoir structure, it may reduce water turbulence inside the reservoir compartment (a taller compartments may have less turbulence at its floor) and may also help to distribute water inside it across a larger algal attachment surface more evenly. When the reservoir structure provides physical support to a waterfall algae scrubber apparatus, the reservoir structure may also function as a pole mount, which might be self supporting from a floor of a sump. Reservoir structures, and their internal reservoir compartments, differ from water pipes primarily due to the generally open roofs ("reservoir top openings") of reservoir compartments, and if a lid is utilized on a reservoir compartment or reservoir structure it is generally not air tight. Thus the air pressure in a reservoir compartment is generally at the atmospheric pressure of the location where the apparatus is located, and a headspace of air may develop inside the reservoir compartment. In contrast, the water pressure inside a water pipe is generally elevated above the atmospheric pressure of the location where the apparatus is located, and there generally is no headspace inside the pipe. Thus a water pipe enables water to "squirt" out of the water pipe, possibly upwards into the air above the level of the pipe.

Reservoir Top Opening: A generally large opening located at an upper section of a reservoir structure, the opening being in fluid communication with the reservoir compartment of the reservoir structure. A reservoir top opening is generally not sealed and thus is open to the atmospheric pressure of the location where the reservoir structure is operating. Although there may be a lid on the opening, it is generally not air tight and thus may allow the reservoir compartment water surface level to fluctuate up and down. Water may overflow out of the opening, in which case the opening is also a water outlet. Water may also or alternately be poured into the opening, in which case the opening is also a water inlet. A reservoir top opening may be sized and shaped to complement the shape of the reservoir compartment so as to allow the user to access to the compartment, and/or to make manufacturing easier.

Ambient Water Surface Level: The water surface level in a sump or other location where an algae scrubber apparatus is disposed. Water from the waterfall algae scrubber drains down onto the ambient water surface level, and must then be pumped back up to the waterfall water delivery structure in order to recirculate. This recirculation path may include passing through other areas of an aquarium structure such as the "display" which houses the livestock.

Reservoir Compartment Water Surface Level: The internal water surface level in a reservoir compartment inside a reservoir structure. This internal water surface level will always be above the ambient water surface level, unless the waterfall itself is submerged.

Pole Mount Reservoir: A reservoir structure which physically supports a waterfall algae scrubber. Because the physical support, water supply source, and also possibly the drain are contained within a single support column of the pole mount reservoir, cost and space are considerably reduced. A pole mount reservoir may operate with or without headspace inside the reservoir compartment. In the present application, "pole mount" means the same as pole mount reservoir, e.g., it is a mount with upflowing water inside it.

Water Delivery Structure: A structure that is in fluid communication with, and supplies water to, a macroalgal attachment surface. A water delivery structure may receive water from a water supply source tubing or a reservoir compartment in a reservoir structure, or another source. Some examples of water delivery structures are a water pipe with a slot, a water pipe with holes, an open trough that overflows, and an open trough with a slot at its bottom. A water delivery structure may also be a reservoir structure by itself, whereby the reservoir structure delivers water directly to a macroalgal attachment surface. Or a water delivery structure may be a combination of pipes, troughs and reservoir structures.

Figure 13:
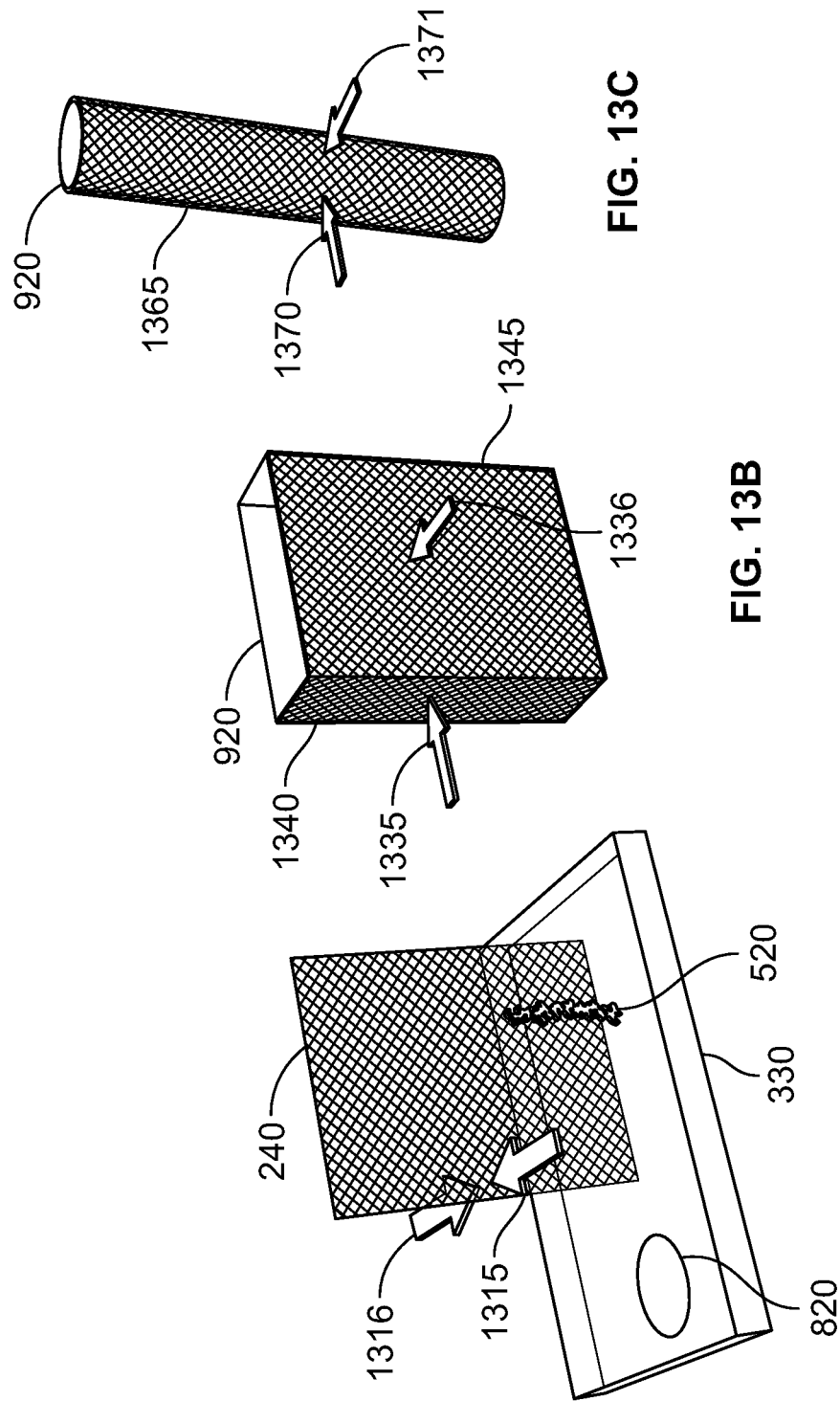
FIG. 13A shows a perspective view of a 2-sided macroalgal attachment surface, and perpendicular access.
FIG. 13B shows a perspective view of a 1-sided macroalgal attachment surface, and perpendicular access.
FIG. 13C shows a perspective view of another 2-sided macroalgal attachment surface, and perpendicular access.

Perpendicular Access: Ability of the user to make optical and physical contact with a macroalgal attachment surface by looking at or touching the attachment surface from a direction that is perpendicular to the attachment surface, without requiring removal or repositioning of the macroalgal attachment structure or a macroalgal settlement structure (illumination devices, however, may still need to be removed or repositioned). This is in contrast to a conventional box placed around a macroalgal attachment material which requires the removal of the material from the box, or the box from the material, in order to clean/harvest the growth, and in some cases even to view the growth. If the macroalgal attachment material is not planar, then a direction of perpendicular access would be that which offered the greatest access to the material. Perpendicular access is very important for harvesting, and is defined further in FIGS. 13A, 13B and 13C.

Macroalgal settlement structure: A structure that catches macroalgae that settles or falls down from a macroalgal attachment surface, yet enables perpendicular "open" access to the macroalgal attachment surface for cleaning/harvesting because the macroalgal settlement structure is below the macroalgal attachment surface including any water delivery structure. The macroalgal settlement structure does not interfere with observation or cleaning/harvesting of the macroalgal attachment surface (the settlement structure is physically "open" on the areas that are in front of the growth surfaces); thus the macroalgal settlement structure does not need to be removed or repositioned in order for cleaning/harvesting to occur. The macroalgal settlement structure has an "open" settlement surface, which is open laterally like a food plate, and not closed like a box with walls. A macroalgal settlement structure may also act substantially as a support for positioning a dome, and could be substantially stationary when the dome is removed or repositioned.

1-Sided or 2-Sided Macroalgal Attachment Material: If a macroalgal attachment material does not allow substantial illumination and water from one side of the material to reach the other side of the material, then it is 1-sided because each surface cannot benefit from the illumination and/or water flow from the other side. However if the material is thin and porous enough, and possibly also translucent enough, then some illumination and water flow from one surface will travel through the material so as to keep the algal "roots" alive longer on the other side, enabling the roots to stay attached to the material longer before dying and detaching (algae can only stay attached when alive). An example of 2-sided material is common plastic canvas "cross stitch" grid used for knitting; illumination and water travel easily through the material. String is another example, because it is too thin to block much water or illumination. An example of 1-sided material is a sheet of metal; even though it is thin and can be made rough on both sides so that algae can attach, no water or illumination can travel from one side to the other side and thus the metal is essentially two 1-sided surfaces which do not benefit each other.

Submerged Gas Compartment: An internal compartment of a submerged enclosure structure which operates similar to a diving bell. This compartment contains some or all of the water delivery structures and algal attachment structures.

Submerged Water Surface Level: The internal water surface level within a submerged gas compartment. This internal water surface level will always be below the ambient water surface level during operation.

Air tight: Substantially sealed so that gas cannot escape. A dome can be air tight so that it can operate as a diving bell, however this does not imply that bottom open sections of the structure must be sealed. An air tight dome can hold gas under water without the gas escaping upwards, even though its lower sections are not sealed or closed, just like a cup turned upside down can hold air under water.

Single Unified Component: A component made to perform the functions of multiple separate components but made as a single indivisible component which cannot easily be separated without destroying it. Most often a single unified component is made with molded plastic.

Illumination Domes

Figure 3:
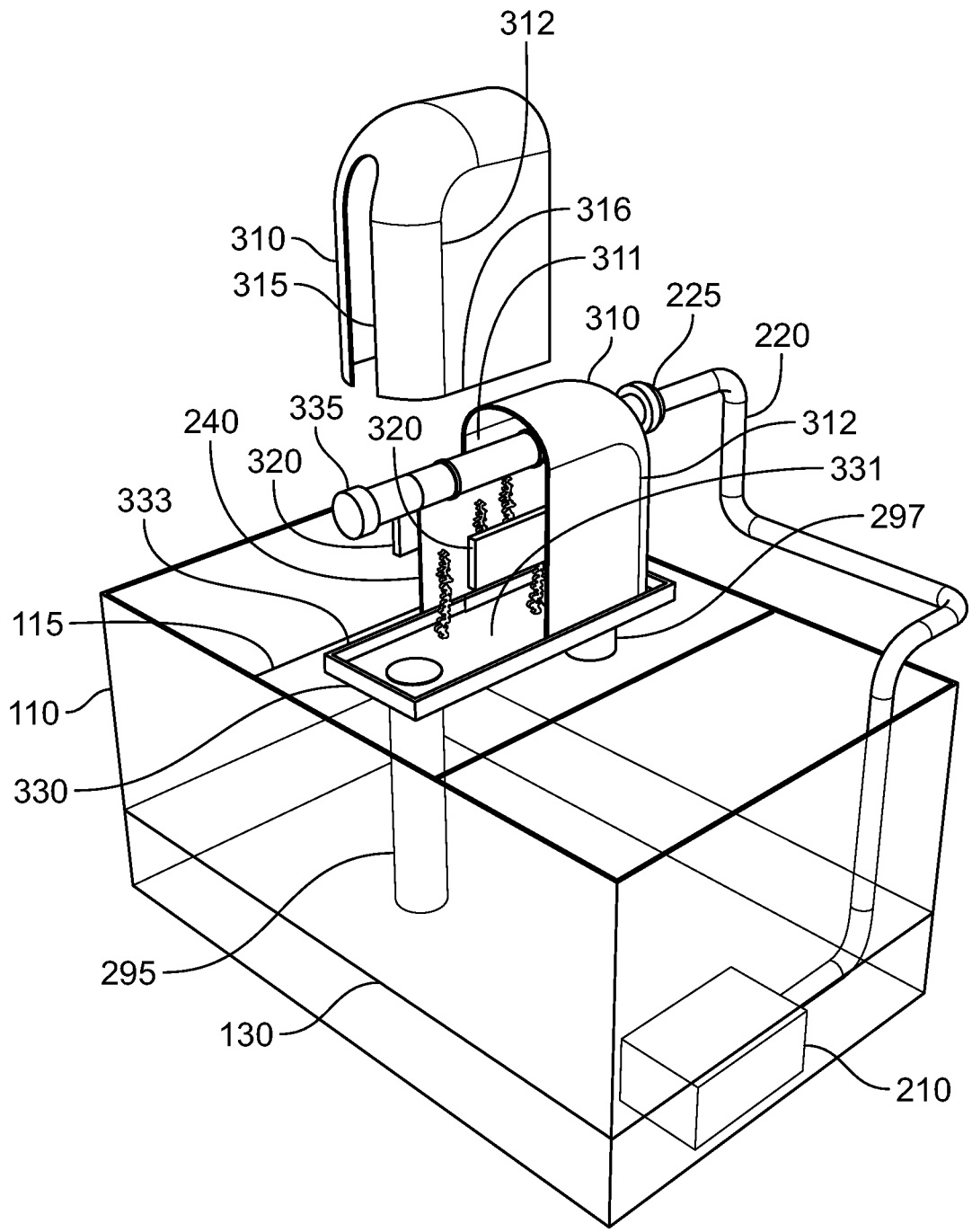
FIG. 3 shows a perspective view of an embodiment of the current invention utilizing an illumination dome.

FIG. 3 shows an embodiment of the current invention which utilizes the previous art water delivery pipe 230, screen 240, shelf 115 and pump 210 of FIG. 2, but with an enclosure structure defining an illumination dome 310 (shown divided into two halves) and a macroalgal settlement structure 330 (which in this embodiment resembles a flat tray), the dome 310 utilizing submersible illumination devices 320 described below. When illumination dome 310 is removed or repositioned in this embodiment, access to half of the algal attachment screen 240 occurs in a single step, without having to remove or reposition screen 240, water delivery structure 230, tray 330, or a separate illumination device. Dome 310 may rest in a first position on a surface such as a macroalgal settlement structure 330 as it does in this drawing, or dome 310 may hang in a first position suspended from water delivery pipe 230 or another structure adjacent to the algae scrubber. By contrast, attaching downward pointing illumination devices to the bottom of the removable previous art lid 290 in FIG. 2 would have caused illumination to be blocked by water delivery structure 230.

In this drawing, 50% of illumination dome 310 is raised upwards to a second position for observation or cleaning/harvesting of algal attachment screen 240, however any percentage or part of dome 310 may be designed to be removed or repositioned to a second position in order to view or access the space inside it, such as 5% or 10% for viewing, or 20%, 30% or 40% for partial cleaning/harvesting, or 60%, 70%, 80%, 90% or 99% for a full cleaning/harvesting in one step while still allowing a small portion of dome 310 to remain attached in a first position to water delivery structure 230 or tray 330. Cutout 315 in the elevated portion of dome 310 (in second position) allows that portion of dome 310 to slide down into first position over water delivery pipe 230, however dome 310 could also have a moveable door that encloses cutout 315 once in the lowered first position, or dome 310 could be enlarged so as to completely enclose cap 335 and coupler 225 when in the lowered first position, leaving only the water supply source tubing 220 to protrude out of dome 310.

Illumination dome 310 is defined by a generally concave inner surface 311, a generally convex outer surface 312, and a bottom edge 316 which forms a shape that complements the size and shape of tray 330. If no tray 330 is utilized, then dome 310 may be structured with a bottom edge 316 which forms a very narrow bottom shape such that minimal illumination escapes out of the lower portion of dome 310 while still enabling dome 310 to be positionable and removable from water delivery structure 230. Such a narrow shape of bottom edge 316 might be 5 mm larger than the width of water delivery pipe 230, which would still allow dome 310 to be lifted up.

Measuring the escapement of illumination from an enclosure structure can be done by placing the algae scrubber in an opaque box of similar size to a typical sump (possibly 1 meter wide, 1 meter tall, and 0.5 meters deep) which is white inside to reflect illumination, and then placing a standard illumination/lux meter inside the box. With the algae scrubber illumination devices 320 not illuminated, the lux meter should read zero. When illumination devices 320 are illuminated and the algae scrubber enclosure structure (310, 330) is enclosed in the first position (operating position), the lux meter measurement is taken. Then dome 310 or a portion of dome 310 is removed for cleaning/harvesting and the lux measurement is taken again. For example, if the measurement of a lux meter were 5 lux with dome 310 in first position, and 500 lux with dome 310 in second position, then illumination reduction would be 99%. Acceptable levels of illumination reduction could be 50%, 60%, 70%, 80%, 90%, 95%, 99%, and 100%. Another way to measure illumination escapement is with absolute lux at the location where the users eyes would be during observation of the apparatus. When dome 310 in the first position (operating), and with all other illumination sources removed or turned off, a lux meter held at the position of the user's eyes and pointed at the apparatus should preferably measure less than 100 lux, and more preferably less than 50 lux, and even more preferably less than 20 lux, and even more preferably less than 10 lux, and even more preferably less than 5 lux, and most preferably 0 lux.

The enclosure structure (310, 330) can be any size, shape or material that provides substantial illumination reduction when dome 310 is in a first position (enclosed) similar to the lowered half of dome 310, yet allows substantial access to algal attachment screen 240 when dome 310 is in a second position (opened) similar to the raised half of dome 310. For example, dome 310 and tray 330 might be made of injection molded thermoplastic such as ABS or polycarbonate, or a thermoset resin such as polyurethane. The material could be any color, or coated with any color, however usually only opaque dark colors will keep a substantial amount of illumination from traveling through the material. Lighter colors, however, especially white, reflect more light inside the enclosure structure (310, 330) and thereby increase the effective amount of illumination reaching algal attachment screen 240. Thus a two-color or two-material enclosure structure (310, 330) might be utilized, being white inside and black outside. Metal or metal foil will block illumination as well, but generally should not be used due to their chemical effect on some livestock.

In embodiments such as FIG. 3 where dome 310 supports illumination devices 320, the dome 310 should be made of material to both support the weight of, and be protected from the heat of, illumination devices 320. However because the submersible illumination devices 320 (described below) are small and lightweight with no metal to corrode, illumination devices 320 can be attached to an interior surface 311 of dome 310 with no special structure or heat reduction required of dome 310. This combination of a simple and lightweight dome 310 and illumination device 320 allows for easy access to algal attachment screen 240 by lifting up dome 310, much like lifting the lid of a cake display tray.

Other embodiments might utilize illumination devices (not shown) which are external to dome 310 and which project illumination through an illumination port similar to port 260 in FIG. 2, in order to illuminate algal attachment screen 240. These illumination devices might be attached to an external surface 312 of dome 310, thus being removed with dome 310; or they might be attached to an upper surface 331 of tray 330, in which case they would remain stationary with tray 330 as dome 310 was removed. Lastly, illumination devices might be attached to sump or aquarium objects near the algae scrubber, where the illumination devices are entirely separate from the algae scrubber but still project illumination through an illumination port in dome 310.

The shape of external surface 312 and internal surface 311 of dome 310 can be any shape which enables the structure 310 to support itself and any illumination devices 320 that may be attached, and which block a substantial amount of illumination from reaching the user. The bottom edge 316 of dome 310 could be shaped to set in a first position inside of a sidewall 333 that goes around the edge of tray 330; this would further help to contain illumination as well as water spray and algal growth. The shape of macroalgal settlement structure 330 could be just a flat shelf which supports dome 310 in a first position, possibly with pegs or notches or a sliding rail to hold dome 310. Or tray 330 could have a sidewall 333 around it as shown, in order to further hold and position dome 310 in the first position. If a sliding rail (not shown) is used to hold dome 310 in a first position on tray 330, then dome 310 could slide on the rail, either laterally or upwards, to an open second position. Tray 330 might include orifices for drain pipes such as drain pipe 295, and backup drain pipe 297, or tray 330 might not have any orifices at all and may just allow overflowing over the edges of tray 330 or sidewall 333. Lastly, the enclosure structure might not include a tray 330, in which case the bottom of dome 310 would remain open and water flowing off of algal attachment screen 240 would not be contained at all. 100% containment of illumination, as measured with a light/lux meter, is possible however if enclosure structure (310, 330) completely seals or surrounds water delivery structure 230 in addition to other structures. Any illumination that might escape down drain 295 or alternate drain 297 can be reduced or eliminated by appropriate shaping or shading of those orifices, and making those orifices black colored.

Sidewall 333 might be a short lip around the edge of tray 330; possibly only 2 to 10 mm above the top surface 331 of tray 330. Or sidewall 333 might be taller, perhaps 10 to 50 mm above top surface 331, in order to contain growth that accumulates at, or falls off of, the bottom of algal attachment screen 240. The height of sidewall 333 might be below the bottom of illumination devices 320, in which case the illumination from illumination devices 320 would travel over sidewall 333; this would allow sidewall 333 to be made of an opaque white material to reflect more illumination inside dome 310. Or the height of sidewall 333 might be above illumination devices 320, in which case sidewall 333 might be made of a transparent or translucent material so that illumination from illumination devices 320 travels though sidewall 333. Alternately, sidewall 333 might instead include an illumination port similar to label 260 of FIG. 2.

Example Claims—Illumination Domes

1. An apparatus for enclosing a waterfall algae scrubber or seaweed cultivator, comprising:
    an enclosure structure movable from a first position to a second position, the first position enclosing an algal attachment surface such that illumination from inside the structure is substantially reduced before traveling outside the structure, and the second position such that access to the algal attachment surface is substantially increased.
2. The enclosure structure of claim 1, wherein the enclosure structure substantially encloses a water delivery structure.
3. The enclosure structure of claim 1, wherein an illumination device is attached to the enclosure structure.
4. The enclosure structure of claim 3, wherein the illumination device is attached to an exterior surface of the enclosure structure such that illumination from the illumination device is directed to travel through an illumination port.
5. The enclosure structure of claim 3, wherein the illumination device is attached to an interior surface of the enclosure structure.
6. The enclosure structure of claim 1, wherein perpendicular access to the algal attachment surface is at least 50% more when the enclosure structure is in the second position than when in the first position.
7. The enclosure structure of claim 1, wherein escaped illumination measured in lux when the enclosure structure is in the first position is at least 50% less than when the enclosure structure is in the second position.
8. The enclosure structure of claim 1, wherein the enclosure structure defines a tray and a dome, the tray having an upper surface and being substantially stationary, the dome having an external surface and a concave internal surface and being substantially supported by the tray and moveable from a first position to a second position.
9. The enclosure structure of claim 8, wherein the tray includes sidewalls.
10. The enclosure structure of claim 9, wherein the height of the sidewalls is lower than an illumination device.
11. The enclosure structure of claim 9, wherein the sidewalls are translucent or transparent and the height of the sidewalls is above an illumination device.
12. The enclosure structure of claim 1, wherein the enclosure structure substantially encloses all water delivery devices and algal attachment surfaces.
13. The enclosure structure of claim 12, wherein the enclosure structure is substantially air tight.
14. The enclosure structure of claim 13, wherein the enclosure structure defines a tray and a dome, the tray having an upper surface and being substantially stationary, the dome having an external surface and a concave internal surface and being substantially supported by the tray and moveable from a first position to a second position.
15. The enclosure structure of claim 14, wherein the tray includes sidewalls.
16. The enclosure structure of claim 15, wherein the height of the sidewalls is lower than an illumination device.
17. The enclosure structure of claim 15, wherein the sidewalls are translucent or transparent and the height of the sidewalls is above an illumination device.
18. The enclosure structure of claim 13, wherein the enclosure structure includes an air-bleed valve.
19. The enclosure structure of claim 13, wherein the enclosure structure is injected with gas.
20. The enclosure structure of claim 19, wherein the gas is injected by an air pump.
21. The enclosure structure of claim 19, wherein the gas is injected by a Venturi valve attached to a water delivery source.
22. The enclosure structure of claim 19, wherein the enclosure structure is weighted so as to remain submerged.
23. The enclosure structure of claim 1, wherein the enclosure structure defines a dome, the dome having an external surface and a concave internal surface and being substantially supported in the first position by a water delivery device.
24. The enclosure structure of claim 23, wherein illumination from the apparatus as measured in lux at a location of a user's eye is to be less than 100 lux when the dome is in the first position.
25. The enclosure structure of claim 23, wherein the dome includes an illumination device attached to an internal surface of the dome.
26. The enclosure structure of claim 23, wherein the illumination device is attached to an exterior surface of the enclosure structure such that illumination from the illumination device is directed to travel through an illumination port.

27. An enclosure structure substantially as hereinbefore described with reference to FIG. 3.

Pole Mounts

Figure 4:
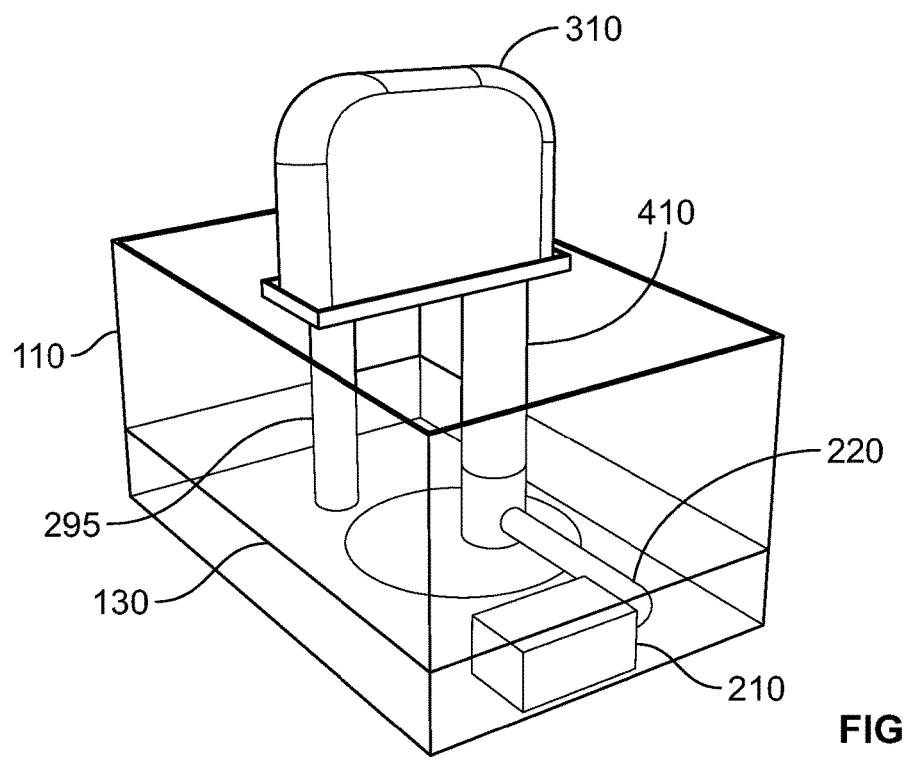
FIG. 4 shows a perspective view of an embodiment of the current invention utilizing an illumination dome and a pole mount reservoir.

FIG. 4 shows an embodiment of the current invention which utilizes a pole-mount reservoir 410 as well as a non-divided illumination dome 310 shown in a first position which encloses substantially all of the water delivery structure and algal attachment surface inside it. A pole mount reservoir is called such because in addition to it's mounting function, it is generally a larger diameter than a simple water pipe and thus holds more water similar to a reservoir.

Because a shelf is no longer needed as in FIG. 3 label 115, there is no possibility of overflowing onto the floor, and thus no secondary backup drain is needed; drain 295 provides all needed drainage and in effect the entire enclosure structure is it's own backup drain because any clogging of drain 295 simply causes water to flow down the sides of the algae scrubber to water surface 130 of sump 110 where it would have gone anyway. And because pump 210 pumps water through water source supply tubing 220 up through the inside of pole-mount reservoir 410, no pipes or tubing need to go through dome 310; thus dome 310 can be constructed of just one simple lightweight box or dome shape without any cutouts or ports. Very lightweight and low cost materials such as corrugated plastic or thermoformed styrene may be used. If illumination devices (not shown) are mounted on the tray instead of dome 310, then dome 310 carries no weight and can be made of plastic as thin as 0.5 mm, and if the shape of dome 310 is made to be rectangular then it could fold flat for shipping. Therefore by utilizing pole-mount reservoir 410 with illumination dome 310, manufacturing costs are reduced, spills on the floor of the room are eliminated, space above the algae scrubber is increased, and access to the water in the sump is also increased because of the removal of the shelf. The sump itself may also be less costly because of this. Lastly, pole mount 410 and drain 295 might be angled instead of vertical as shown; an angle of 10, 20, 30, 40, 50, or 60 degrees from vertical reduces or eliminates the falling sound of water within drain 295. If drain 295 were coupled to pole mount 410, then drain 295 could aid pole mount 410 in providing support, and one or both could be angled.

Figure 5:
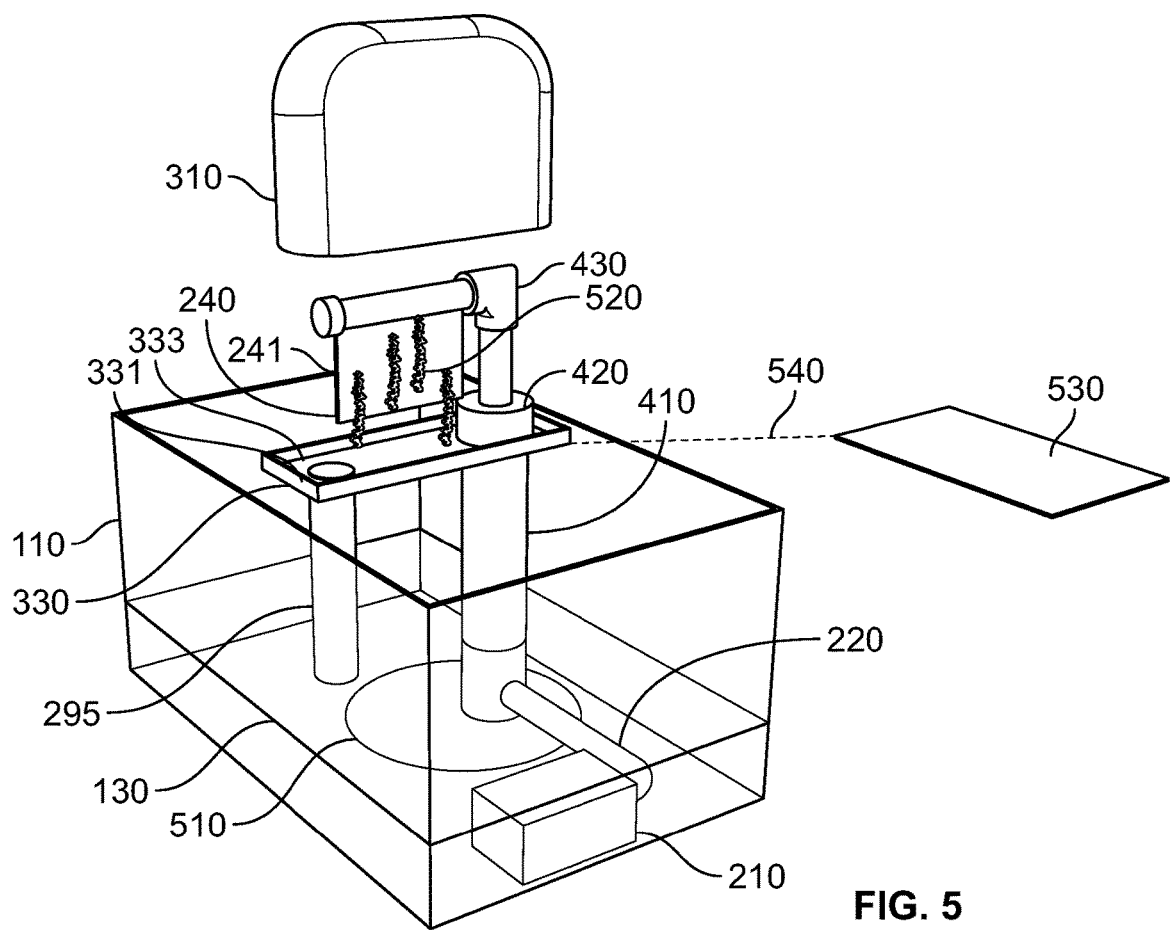
FIG. 5 shows a perspective view of the embodiment of FIG. 4 with the illumination dome lifted upwards.

FIG. 5 shows the embodiment of FIG. 4 with the illumination dome 310 raised upwards to a second position and with the assumption that illumination devices (not shown) are mounted to the interior of dome 310. Instead of utilizing alternate drain 297 in FIG. 2 as a drain, it is instead utilized in exactly the opposite way: it is reversed in flow so that water flows up into the algae scrubber instead of down out of it, and its pipe is extended downward into sump 110 so that it can physically support the entire waterfall algae scrubber, thus becoming a pole mount reservoir 410 with coupler 420 and base 510. Water supply tubing is not normally thought of as a support structure such as this. A lightweight illumination dome 310 can then replace the heavy and bulky illumination devices 250 of FIG. 2 because heavy supporting walls 270 of FIG. 2 are no longer needed. In FIG. 5 these changes completely eliminate water delivery support walls 270, the heavy and bulky illumination devices 250, and the portion of water source supply tubing 220 which rises above ambient water surface level 130. Thus by moving the water supply source from above the algae scrubber to below it, and also by utilizing this same water source as a physical support mount, the high cost construction and space utilization problems of FIG. 2 are solved, including shelf 115 which is no longer needed. And although described as a "pole", the shape of pole mount reservoir 410 can be any height, width, cross sectional area, or cross sectional shape such that it functions as described herein.

Illumination dome 310 is shown raised upwards into a second position for observation/cleaning/harvesting of algal attachment screen 240 and/or water delivery structure 430. Water is pumped by pump 210 through the submerged portion of water supply source tubing 220 into pole mount reservoir 410 and then through coupler 420 into water delivery structure 430, which in this embodiment is comprised of a vertical and horizontal pipe connected together with an elbow fitting. Water then flows down attachment surface 241 of attachment material 240 onto algal settlement tray 330, and then continues down drain 295 back down to ambient water surface level 130 of sump 110. Lightweight illumination dome 310 has internal illumination to facilitate algal growth 520, and this combined with the small space requirement of water delivery structure 430 allows for a very compact and low cost construction because algal settlement tray 330 must only support algal growth 520, lightweight dome 310, and drain 295. And if dome 310 is held in position by water delivery structure 430, then tray 330 only need support algal growth 520 and drain 295.

When lowered to a first position where it is touching algal settlement tray 330, especially when surrounded by sidewall 333, illumination dome 310 completely encloses water delivery structure 430 thus requiring no components to intersect dome 310. Thus raising dome 310 to second position as shown is relatively easy because no water delivery pipes or long water supply source tubings are attached or pass through dome 310 as they do in FIG. 2. Lastly, water flowing up pole mount reservoir 410 can continue when dome 310 is raised to the second position during observation of the growth, because the flow of water through water delivery structure 430, down algal attachment surface 241, onto tray 330, and down drain 295, is not interrupted as it would be in FIG. 2. Further simplicity may be had by routing drain 295 downwards through pole mount 410 such that water exits below ambient water surface level 130, as will be shown in a subsequent drawing; this allows the algae scrubber to be essentially a single column. It is also contemplated that the diameter of pole mount reservoir 410 could be enlarged to match the width and shape of tray 330, thus making a true single column apparatus.

Coupler 420 is attached or molded on to algal settlement tray 330 such that pole mount reservoir 410 and/or water delivery structure 430 decouple from tray 330 for cleaning/harvesting. Pole mount 410 or it's base 510 which sits on the floor of sump 110 may be weighted so that pole mount 410 stays stationary in sump 110 while tray 330 and water delivery structure 430 are removed; this preserves the positional relationship between water delivery structure 430 and tray 330 which helps prevent algal growth from being pulled apart. Coupler 420 could alternately be attached or molded on to both tray 330 and pole mount 410, whereby only water delivery structure 430 would decouple, leaving tray 330 and pole mount 410 remaining in the sump. Lastly, coupler 420 could be releasably attached to water delivery structure 430, tray 330, and pole mount 410 so that they could all be removed separately.

Macroalgal settlement surface 331 defines a plane that is represented by rectangle 530 which is shown at the same elevation as surface 331 by dotted line 540. One of the defining factors of a pole-mount embodiment of the current invention is that the water can be supplied to the apparatus from below the apparatus through pole mount reservoir 410 instead of from above the apparatus as in previous art algae scrubbers. So by requiring that the path of water through pole mount 410 (and water delivery structure 430) intersect plane 530 of settlement surface 331, it can be seen how water must then come from below surface 331 instead of from above it. Furthering this concept is requiring that pole mount 410, or water delivery structure 430, actually contact macroalgal settlement structure 330 such as it does in FIG. 5. Such contact might be a simple weighted tray 330 that sits on a lip of pole mount 410, or a releasable mechanism that allows easy detachment of tray 330 from pole mount 410, or tray 330 might be permanently coupled to pole mount 410, possibly by being made of the same molded material as pole mount 410. And although shown that pole mount 410 transitions to water delivery structure 430 at the point of intersection with tray 330, the transition could instead be above or below the point of intersection. Lastly, water delivery structure 430, settlement structure 330, and pole mount 410 could be a single unified component.

Figure 6:
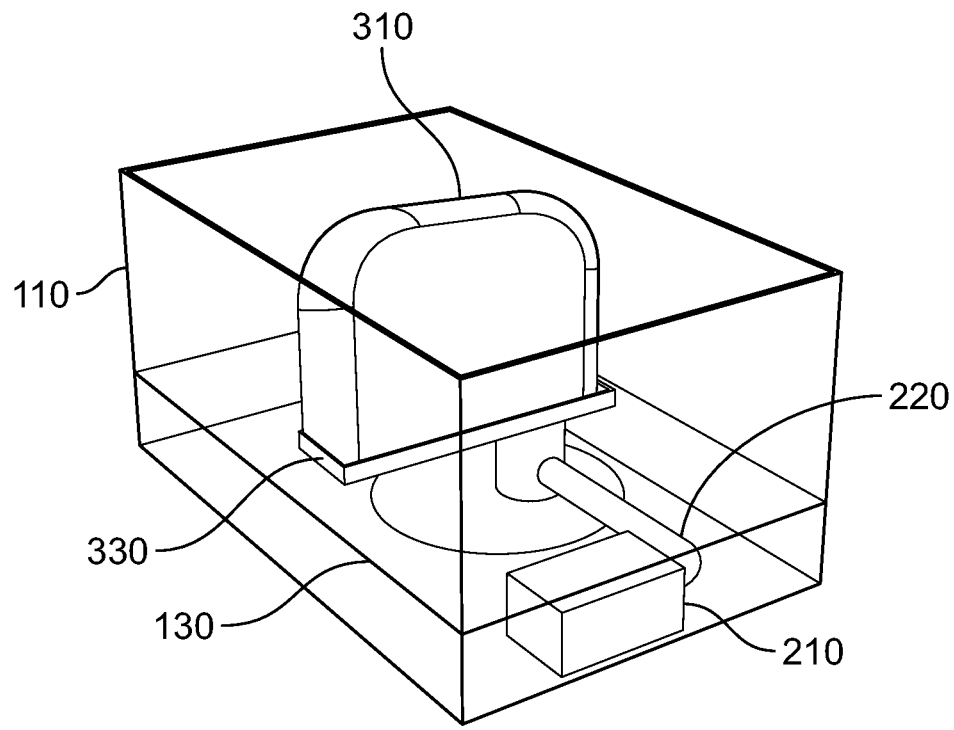
FIG. 6 shows a perspective view of the embodiment of FIG. 4 lowered to operate at the water level in the sump.

FIG. 6 shows a pole mounted algae scrubber embodiment similar to FIG. 5 except the algae scrubber is positioned just above the ambient water surface level 130 of sump 110. This position contributes even more open space above sump 110, and eliminates the need for drain pipe 295 of FIG. 5 entirely because the drain orifice (not visible) is essentially now already at the height of the ambient water surface level 130. This eliminates all gurgling and surging sounds produced by some drain pipes, and further reduces cost by requiring less length for the long pole mount reservoir 410 of FIG. 5. And the physical strength needed by tray 330 can be even further reduced because if dome 310 hangs on water delivery structure 430 of FIG. 5 instead of sitting on tray 330, then tray 330 need only support algal growth 520 of FIG. 5 and nothing else. Pump 210 might also be made smaller because the required height that water must be pumped up to is less; water supply source tubing 220 would carry the same volume of water however.

The water level 130 in many sumps varies greatly, and this is another reason why previous art waterfall algae scrubbers were positioned far above (10-30 cm) the ambient water surface level 130. However the current embodiment of FIG. 6 has no problem with a rising water level 130 at all, because at worst, the water inside dome 310 overflows tray 330 and spill back down to water level 130 where is would have gone anyway. The algae scrubber will continue to operate in elevated water levels 130, although the effective waterfall distance inside dome 310 will be less as the water level 130 rises. This too can be accounted for as shown in the next figure.

Figure 7:
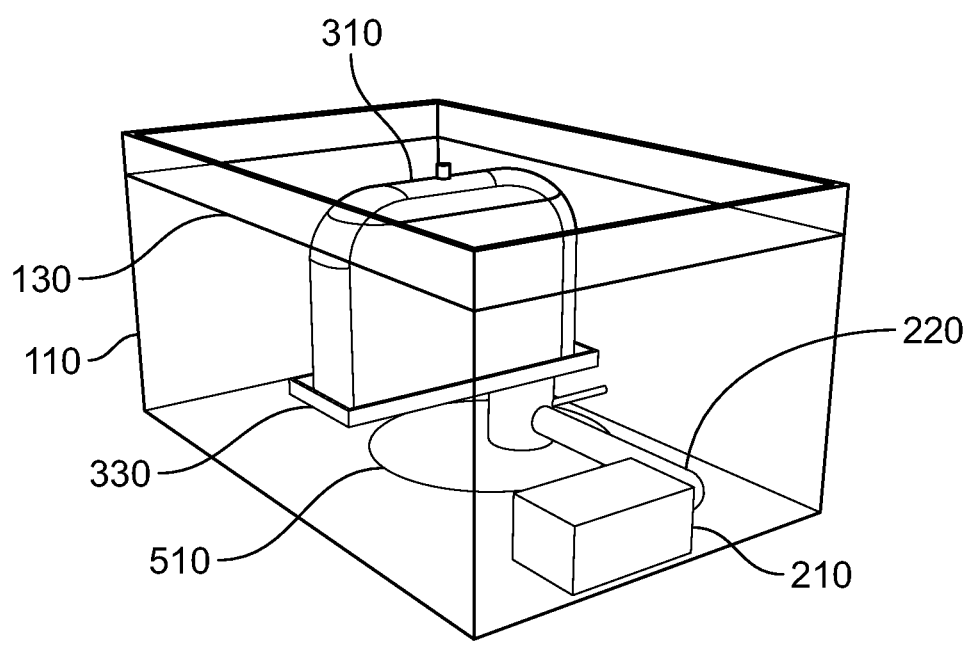
FIG. 7 shows a perspective view of an embodiment of the current invention utilizing an illumination dome for submerged waterfall operation.

FIG. 7 shows a pole mounted embodiment similar to FIG. 6 with the same pump 210 and water tubing 220, except that dome 310 is now an air tight illumination dome 310 for submerged operation. Air tight dome 310 can be an illumination dome 310 as in the previous figures or it can be a dome without attached illumination, instead enclosing a stationary illumination device that perhaps is attached to tray 330. Dome 310 is shown mostly submerged below ambient water surface level 130, however dome 310 could instead be operated totally submerged, or slightly submerged, depending on the ambient water surface level 130 in sump 110. Any part of the apparatus, including base 510 if dome 310 were latched on to tray 330, might be weighted so as to keep the apparatus submerged. Submerged operation such as this can require the least amount of space of all the waterfall embodiments, and can be made to be dry-out (desiccation) proof as shown in the next figure. It is also contemplated that pump 210 could be self contained within base 510 or pole mount 410, thus eliminating tubing 220 and adding weight to keep the structure submerged.

A submerged waterfall embodiment such as this has interesting applications, such as the possibility of placing the algae scrubber in the actual aquarium instead of the sump. Users typically prefer to not have waterfall algae scrubbers above their aquariums because of the large space occupied by the scrubber; this space is usually needed to access the inside of the aquarium from the top. Also, the draining of water into the aquarium from above it tends to splash, and in saltwater aquariums it causes a buildup of salt on nearby surfaces and wires. Lastly, an escapement of illumination from previous art scrubbers is very visible above an aquarium, especially at night. Previous art scrubbers almost never block all illumination from escaping because of the bulky illumination devices that must be easily removed for observation and cleaning; they cannot be completely sealed shut.

Figure 8:
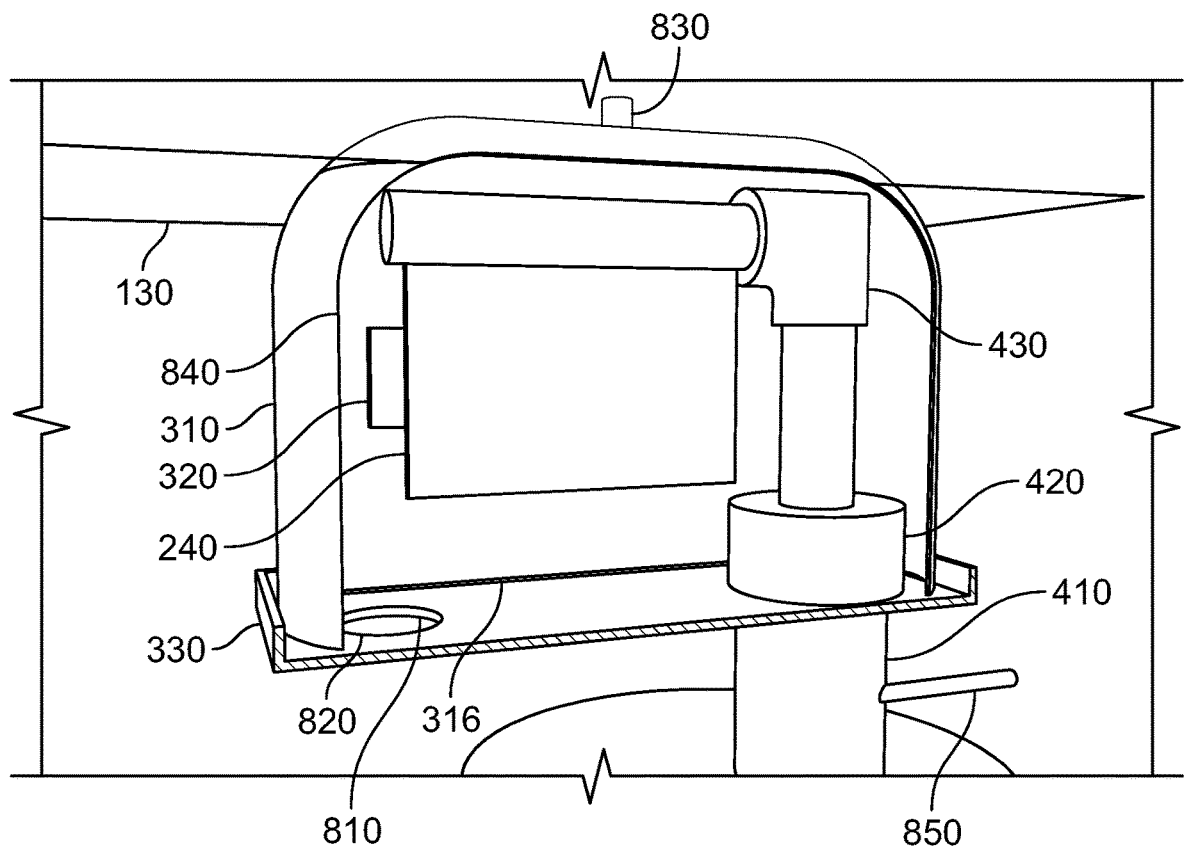
FIG. 8 shows a perspective cutaway underwater view of the embodiment of FIG. 7.

The present invention embodiment however allows a waterfall algae scrubber to be placed submerged in the main aquarium, possibly hidden behind (or decorated as) rocks or plants, with no splashing or gas bubbling (very little gas escapes dome 310), and with practically no escapement of illumination. For aquariums without sumps, the submerged waterfall embodiment of FIG. 7 may be the only option if the user desires a waterfall algae scrubber instead of an upflow scrubber (as described in applicant's U.S. Pat. No. 9,115, 008). Small aquariums also, such as the popular desktop "all in one" styles that have pseudo sumps on their back walls (instead of beneath), might also have smaller sized waterfall algae scrubber embodiments installed which can fit into one of the submerged compartments in the back. Operation of the submerged embodiment of FIG. 7 is shown in FIG. 8:

FIG. 8 shows an underwater cutaway view of the submerged embodiment of FIG. 7. Dome 310 is shown almost completely submerged beneath ambient water surface level 130, with only the topmost portion of dome 310 above water surface 130, as well as an air-bleed valve 830. Because dome 310 is an air tight enclosure per the definition herein, pushing dome 310 below the water surface 130 causes the submerged water surface level 810 inside dome 310 to also push downwards, just as if you took an empty cup and pushed it under water while it was upside down (open side facing down). It's also the same concept as a diving bell, which has an open port on the bottom to allow divers to jump "down" into the water even though the whole structure is already submerged. Therefore it can be seen here where the ambient water surface level 130 exists on the outside of dome 310 but this water level does not continue to exist on the inside of dome 310. The inside is dry. And this allows the waterfall algae scrubber to operate under water.

The air pressure inside dome 310 keeps the submerged water surface level 810 approximately at the bottom edge 316 of dome 310, which is also approximately at the bottom level 810 of drain orifice 820 of algal settlement structure tray 330. Tray 330 is not needed for submerged operation however; if tray 330 were removed then submerged water surface level 810 would remain approximately the same. Weights (not shown), or a weighted material to make dome 310 heavier, holds dome 310 down so that it rests on tray 330 and does not float upwards. Alternately as explained in FIG. 7, dome 310 might be latched onto tray 330. As in FIG. 5, water is pumped up through pole mount 410, through coupler 420, into water delivery structure 430 where it then flows down algal attachment screen 240. Illumination is provided on the rear side of screen 240 with illumination device 320; a second device 320 on the front side of screen 240 is not visible in this cutaway view.

The pumping of water into submerged compartment 840 would normally cause air to be pushed downward out of drain orifice 820, which does occur to a small extent when the flow out of water delivery structure 430 first begins, however once flowing, this new quantity of water then exits submerged compartment 840 through orifice 820, thus equalizing the pressure inside submerged compartment 840 (water input equals water output) so that submerged water level 810 remains approximately constant. Some leakage via gas bubbles does occur out of drain orifice 820 when water is flowing rapidly down algal attachment screen 240 because of turbulence and entrained gas bubbles created when water impacts tray 330 (or impacts submerged water level 810). If this gas leakage were not replaced, internal water level 810 could slowly rise inside dome 310. Replacing this escaped gas can be done by injecting gas into dome 310 directly, or into the flow of water going through pole mount 410 by using gas tube 850, either of which could be done with an air pump. Injecting gas into pole mount 410 via gas tube 850 also has the option of using a Venturi valve as shown by applicant's U.S. Pat. No. 9,115,008 in FIG. 3, label 305. If operated as a Venturi tube, gas injection tube 850 could be extended upwards so that it pulls air from above ambient water surface level 130.

Besides the relatively small space occupied by this algae scrubber under water, submerged operation offers an advantage to users who have electric utility power outages on a regular basis. With above-water waterfall algae scrubbers, an electric power outage stops the water flow to the algae scrubber, causing any growth on the algal attachment screen 240 to eventually dry out and die. However because dome 310 is submerged in this embodiment, compartment 840 can be allowed to slowly fill with water so as to keep the algal growth wet; wet growth can stay alive for many days without any water flow or illumination, thus giving the user time to restore electrical power. This filling of dome 310 with water can be accomplished by air bleed valve 830. When an electric power outage occurs, gas injection into dome 310 will stop and air bleed valve 830 will allow gas inside submerged compartment 840 to slowly escape, such that submerged water level 810 will slowly rise until it is level with ambient water surface level 130. This will then keep algal attachment screen 240 submerged until electric power is restored. Air bleed valve 830 could be adjusted by the user so that very little gas normally escapes, thus reducing the required volume of injected gas during normal operation, yet still allowing submerged compartment 840 to fill with water when needed to keep algal growth alive.

Another useful application of a submerged embodiment is automatic feeding for livestock. As just explained, turning off electric power can enable compartment 840 to fill up with water. At these times, and if there is no tray 330 (or if drain orifice 820 is large enough), livestock can enter compartment 840 and eat algal growth that has grown on material 240. Then when electric power is restored, gas will once again start to fill compartment 840 and the livestock will be pushed out downwards. Automatic feeding can also be accomplished with upflow scrubbers (U.S. Pat. No. 9,115,008), however they are never lifted above the ambient water surface level and thus cannot use gas as a way to prevent livestock from eating the algal growth continuously.

Figure 9:
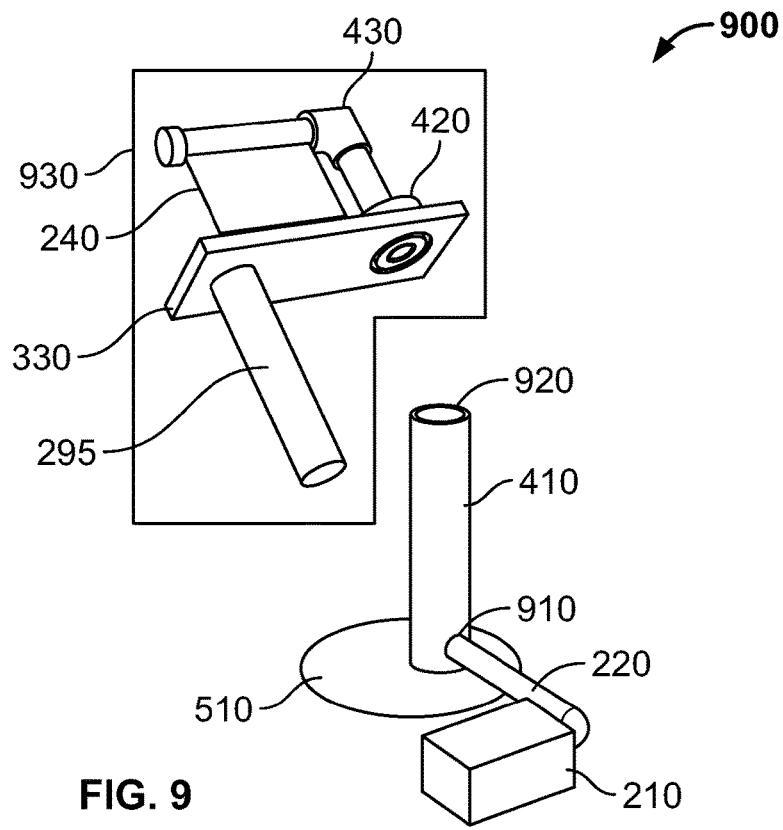
FIG. 9 shows a perspective view of the embodiment of FIG. 5 separated from its pole mount reservoir.

FIG. 9 shows a pole mount reservoir embodiment 900 which is the embodiment of FIG. 5 but with the upper portion 930 removed for cleaning, harvesting, or maintenance. In this embodiment 900, upper portion 930 includes water delivery structure 430, coupler 420, macroalgal attachment material 240, macroalgal settlement tray 330, and drain pipe 295. Coupler 420 is shown attached to algal settlement tray 330 which is attached to drain pipe 295, thus enabling drain pipe 295 to be removed for cleaning because it often clogs when algal growth is thick; coupler 420 is also shown attached to water delivery structure 430 which is attached to algal attachment screen 240, thus enabling any macroalgal growth, including algae settled upon algal settlement tray 330, to be easily removed together for harvesting. This is useful because as shown in FIG. 5 and FIG. 10, the macroalgal growth 520 in those figures tends to extend downward from attachment surface 241, subsequently piling up on settlement tray 330, sometimes several centimeters thick. Thus by keeping screen 240 and tray 330 together as they are removed for cleaning, algal growth 520 in FIG. 5 and FIG. 10 will not be pulled apart; pulling macroalgae apart can cause pieces of algae to fall into the sump where the algae will circulate back to the aquarium; large portions of algae might also fall on to the floor. Coupler 420 is shown detached from water outlet 920 of pole mount reservoir 410 and base 510; unlike previous art FIG. 2 where continuing to operate water supply source pump 210 would cause water to be sprayed randomly, in FIG. 9 it can be seen that water supply source pump 210 could continue to operate, having water only to smoothly overflow back downwards because of the slow velocity of water inside large diameter pipe 410. When upper portion 930 is lowered back into operating position, coupler 420 releasably positioned on pole mount reservoir 410, possibly with a friction fit or held in place by the weight of the upper portion 930. Locking, alignment, or other latching mechanisms could also be utilized to keep algal settlement tray 330 horizontally level or in a particular orientation; this would prevent rotation around pole mount reservoir 410.

At first it did not seem like good practice to detach upper portion 930 of a structure that had upflowing water in it, only to leave a lower portion still in position in a sump, because if this were done with water flowing then the water might shoot upwards out of outlet 920 causing short circuits of nearby electrical wires in the sump area. Similarly, when upper portion 930 is lowered into operating position, the water velocity from the lower section might push upper section 930 back upwards. Even though locks could be used to hold the upper portion 930 into operating position, this requires extra hardware and time to lock it, and also requires the user to remember to lock it, which may not always happen. However by utilizing pole mount reservoir 410 for the mount, instead of a narrow water pipe, it turns out that the large diameter of pole mount reservoir 410 enables the upwards velocity of water to be much slower than a narrow pipe for a given amount of water volume. Thus not only does the larger diameter of pole mount reservoir 410 provide for a stable physical mounting base, and the larger amount of water in mount 410 adds weight and even more stability, but the reduced water velocity inside it allows the water to continue to flow in a slow controlled manner when upper portion 930 is removed; the water just smoothly overflows back down the external walls of pole mount reservoir 410. The upper portion 930 need not be locked down into position, and water flow need not be turned off. Water pump 210, tubing 220, water inlet 910, and base 510 remain in sump 110 or can also be removed for cleaning or maintenance. When the user needs to remove the entire algae scrubber 900 from the sump, the water pump 210 is turned off and water inside mount 410 drains out, making the structure lightweight for removal.

Typical water flow values for an algal attachment screen 240 of width 25 cm are 1500 lph (liters per hour); for such a water flow the pole mount reservoir 410 has an inside diameter of 5-8 cm, thus providing strong physical support if made of standard PVC pipe without causing water to shoot up into the air when upper portion 930 is lifted. A larger algal attachment screen 240 of width 50 cm has 3000 lph of water flow, and pole mount reservoir 410 has an inside diameter of 10-12 cm. As long as water does not rise up more than about 3 cm above water outlet 920 when upper portion 930 is lifted, then the inside diameter of pole mount reservoir 410 should be sufficient as long as it provides enough physical support for the weight of upper portion 930.

Example Claims—Pole Mount Reservoirs

1. An apparatus for supporting macroalgal attachment material and supplying water to a macroalgal attachment surface, comprising:
   a macroalgal attachment material defining a macroalgal attachment surface;
   a macroalgal settlement structure defining a macroalgal settlement surface;
   a water delivery structure, the water delivery structure to intersect a plane (530,1470) of the macroalgal settlement surface;
   a positioning mechanism, the positioning mechanism to position the macroalgal attachment material such that the macroalgal attachment surface receives water from the water delivery structure;
   an attachment mechanism, the attachment mechanism to couple the macroalgal settlement structure to the water delivery structure and to align the macroalgal settlement surface such that macroalgae is enabled to travel from the macroalgal attachment surface to the macroalgal settlement surface.
2. The apparatus of Claim 1, wherein the water delivery structure and the macroalgal settlement structure remain coupled when the macroalgal settlement structure is removed for cleaning/harvesting.
3. The apparatus of Claim 2, wherein the water delivery structure and the macroalgal settlement structure remain in position relative to each other when the macroalgal settlement structure is removed for cleaning/harvesting.
4. The apparatus of Claim 1, wherein the macroalgal attachment material is supported by the water delivery structure.
5. The apparatus of Claim 1, wherein the macroalgal attachment material is supported by the macroalgal settlement structure.
6. The apparatus of Claim 1, wherein the water delivery structure is a water pipe.
7. The apparatus of Claim 1, wherein the water delivery structure is a reservoir.
8. The apparatus of Claim 1, further comprising:
   a pole mount;
   a pole mount coupler, the pole mount coupler to couple the macroalgal settlement structure to the pole mount such that water traveling up the pole mount continues to travel into the water delivery structure.
9. The apparatus of Claim 8, wherein the pole mount supports the apparatus from ground level (1170).
10. The apparatus of Claim 9, further comprising a drain pipe, the drain pipe coupled to the pole mount.
11. The apparatus of Claim 9, wherein the drain pipe is disposed within the pole mount 12. The apparatus of Claim 11, wherein the drain pipe is angled.
13. The apparatus of Claim 1, further comprising:
   a pole mount;
   a pole mount coupler, the pole mount coupler to couple the water delivery structure to the pole mount such that water traveling up the pole mount continues to travel into the water delivery structure.
14. The apparatus of Claim 13, wherein the pole mount supports the apparatus from ground level (1170).
15. The apparatus of Claim 13, further comprising a drain pipe, the drain pipe coupled to the pole mount.
16. The apparatus of Claim 15, wherein the drain pipe is disposed within the pole mount
17. The apparatus of Claim 17, wherein the drain pipe is angled.
18. The apparatus of Claim 1, wherein the water delivery structure and the macroalgal settlement structure are a single unified component.
19. The apparatus of Claim 8, wherein the pole mount and the macroalgal settlement structure are a single unified component.
20. The apparatus of Claim 8, wherein the pole mount, macroalgal settlement structure, and water delivery structure are a single unified component.
21. An apparatus for supporting macroalgal attachment material and supplying water to a macroalgal attachment surface substantially as hereinbefore described with reference to FIGS. 4-9.

Reservoir Overflows

Figure 11:
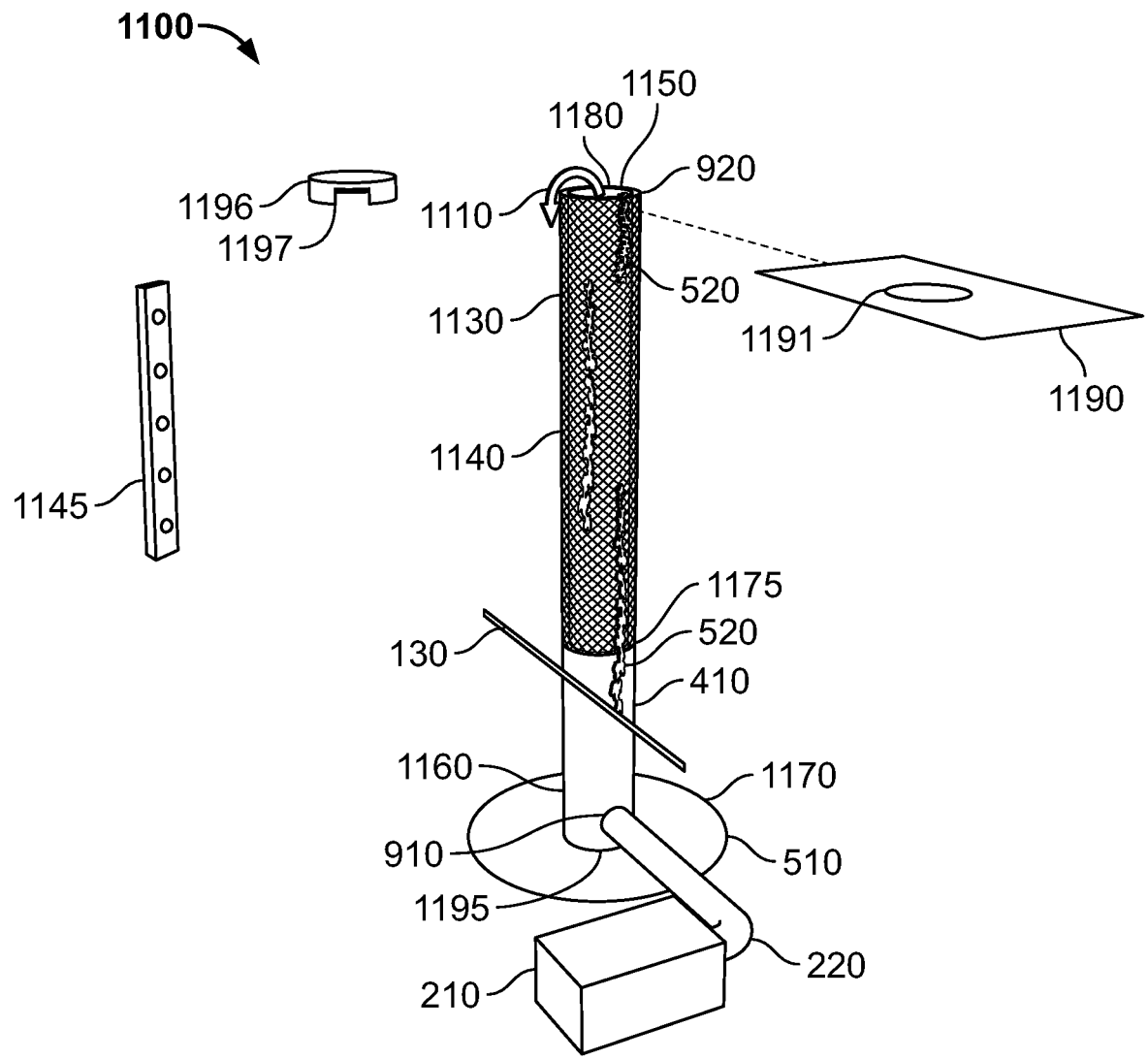
FIG. 11 shows a perspective view of a pole mount reservoir overflow embodiment of the current invention.

FIG. 11 shows an embodiment 1100 of the present invention which is essentially what remains after upper portion 930 in FIG. 9 is removed. As a matter of fact, is was while drafting FIG. 9 and describing the overflowing action of water down pole mount 410 that it was realized that pole mount 410 would grow algae on itself if illuminated, and therefore could operate independently as a very simple waterfall algae scrubber embodiment itself if algal attachment surfaces were placed on its external wall and if illumination were pointed at these surfaces. Algal growth on plumbing tubing is normally not desired on aquarium equipment, but because of the small footprint required on the sump floor, and the small number of components required, this embodiment is ideal for many situations. "External surface" is defined herein to be the outside wall (of a pipe or structure) that contacts the ambient air or water surrounding the pipe or structure, and is the surface the user sees when looking at apparatus 1100 while in operation. In contrast, "internal surfaces" of a pipe or structure would not be in contact with the surrounding air or water, and would not be visible to the user in normal operation unless the user purposely looked inside of the pipe or structure.

Pole mount reservoir 410 is supported by base 510 which sets at ground level 1170 of a sump (not shown). Water pump 210 pushes water through water supply source tubing 220 into pole mount reservoir water inlet 910, where the water then flows up an internal surface 1180 of a reservoir compartment (not shown) inside pole mount reservoir 410. Because embodiment 1100 is essentially made of a single length of plumbing pipe, internal surface 1180 of the internal reservoir compartment is simply be the inside surface (inside diameter) of pole mount reservoir pipe 410.

Because water continues to flow upward and out of pole mount reservoir 410, if the water does not have enough upwards velocity to "shoot" up into the air above outlet 920 then the water will overflow the rim of outlet 920 and turn downwards in the direction of arrow 1110 where the water then flows down external surface 1160 of pole mount reservoir 410. One way of keeping the upwards velocity of water low so that it does not shoot up into the air is to define that the area of water outlet 920 which is represented by circle 1191 be larger than the area of water inlet 910; the area of water inlet 910 is approximately the cross sectional area of water pump tubing 220. This will slow down the velocity of water from pump 210 as the water enters pole 410, although of course the volume of water in liters per minute will be the same. For example, under typical aquarium sump operating conditions of a 10, 15 or 20 cm diameter pole 410, if the ratio of water outlet area 920 to water inlet area 910 is at least 5, then the upwards velocity of water inside pole 410 should not be enough to shoot into the air more than 3 cm above pole 410. Larger ratios such as 10, 15, 20, 30, 40 or 50 would allow even more water to be pumped by pump 210 into larger diameter reservoirs 410 without the water shooting into the air more than 3 cm After overflowing the rim of water outlet 920, the water then comes into contact with algal attachment surface 1130 of macroalgal attachment material 1140 before finally returning back to ambient water surface level 130 (represented as line 130) of the sump (not shown). If the plane that is represented by rectangle 1190 of the rim of outlet 920 is substantially horizontally level, similar to cup of water on a table, then the downward water flow will contact attachment surface 1130 in a substantially equal amount around the circumference of pole mount reservoir 410. The combination of water flow, rough attachment surface 1130, and illumination from an illumination source such as source 1145 causes macroalgal growth 520 to attach to and grow on attachment surface 1130. And although FIG. 9 shows pole mount reservoir 410 supporting and mounting upper portion 930, in FIG. 11 pole mount reservoir 410 is essentially supporting and mounting itself and macroalgal attachment material 1140, and thus continues to be a mount as well as a reservoir.

Two features of embodiment 1100 are of note: The first is that the water overflows substantially all the way around pole mount reservoir 410 outlet 920 instead of just part of outlet 920. Whether the shape of pole mount reservoir 410 (or outlet 920) is round as shown or another shape such as square or rectangular, this feature of water overflowing substantially equally around the entire circumference of outlet 920 maximizes the utility of pole mount reservoir 410 compared to water simply overflowing over a portion of the circumference, or over a wall such as a sump wall, which is normally thought of when a waterfall is described. All parts of the rim and pole are utilized for algal attachment and for receiving illumination, not just some parts. And because pole mount reservoir 410 physically supports itself above ambient water surface level 130, this usage of the entire circumference of pole mount reservoir 410 allows the maximum area of algal attachment surface 1130 for a given size of pole mount reservoir 410, thus minimizing manufacturing costs. Alternately to complete circumference water flow, a cap 1196 (shown separate from apparatus 1100) with water outlets 1197 could be place on top of outlet 920 so as to provide a cover. It is contemplated that water outlets could additionally be located below outlet 920 in wall 1150, although they would need to be reduced in size because of the increase in water pressure below outlet 920.

The second feature of note is that only a single thin wall 1150 is needed for the structure of pole mount reservoir 410. Water flowing up the internal reservoir compartment of pole mount reservoir 410 will be in contact with internal water retaining compartment surface 1180 of wall 1150, and the resulting overflowing water coming downwards will be in contact with external surface 1160 of pole mount reservoir 410 where attachment material 1140 is disposed. This usage of water coming into contact with both sides (internal and external) of a single wall 1150 all the way around the circumference of pole mount reservoir 410 again makes maximum usage of the structure of pole mount reservoir 410, as compared to for example a horizontal river algae scrubber design which only makes use of an upper surface of it's entire structure, or an overflowing wall of a sump which only makes use of one of it's several walls. Typical thicknesses of wall 1150 might be the same as the pipe used to construct it: 2-5 mm for typical aquarium sump applications. If large tubing such as 30 cm diameter is utilized, then wall 1150 thickness might be as high as 10 mm. If decorations such as gravel or rock are placed on external surface 1160 then the operating thickness will be wall 1150 thickness plus decoration thickness. This decoration may also act as the attachment material 1140, in which case the external surface of the decoration could be attachment surface 1130. Further, the thickness of a decoration might vary based on location on external surface 1160. For example, the entire algae scrubber 1100 might be decorated as a volcano, with 1 cm decoration thickness at the level of water outlet 920, and 20 cm decoration thickness at the ambient water surface level 130. Thus if wall 1150 thickness of pipe 410 were 1 cm, the effective wall thickness would be at total of 2 cm at water outlet 920, and a total of 21 cm at water surface level 130.

Embodiment 1100 makes further use of the concept of utilizing the majority of its structure, by physically supporting itself on base 510 which rests at ground level 1170 which may be the floor of a sump. Although FIG. 9 shows pole mount reservoir 410 also physically supporting upper section 930 on base 510, upper section 930 is a separate, additional set of components. Contrastingly, FIG. 11 shows pole mount reservoir 410 to be practically the entire algae scrubber itself. In fact if water pump 210 is not taken into consideration or were included inside of pole mount 410, and if pole mount reservoir 410 had a large enough diameter to prevent falling over, and if macroalgal attachment surface 1130 were obtained by simply roughing up the exterior surface 1160 of pole mount 410, then the total number of components required to construct this embodiment would be just one (the pole).

Embodiment 1100 also has advantages of non-clogging, and self-correcting flow. Regular water hoses with slots or small holes (often used in gardening to soak the soil) can lose flow because the small orifices are easily clogged by particles in aquarium water, or by hard lime/carbonate buildup similar to that in showers and sinks. The large outlet 920 on pole mount reservoir 410 however would rarely clog if the diameter of outlet 920 were just one centimeter or larger; and since it is contemplated that the diameter of outlet 920 would be in excess of 3-10 cm, it could be stated that a clog would simply never occur. And if plane 1190 of outlet 920 were substantially horizontally level, then any non-balanced flow would self correct because when a section of the rim of outlet 920 begins to have larger/higher algal growth than other sections do, it will start to block and slow down water flow at that section and will thus increase flow at other sections on the rim. Thus the areas of higher algal growth on the rim of outlet 920 will then receive less nutrients from the reduced water flow and will begin to grow less compared to the shorter growth areas which now receive more overflowing water flow and more nutrients. The sections with shorter algal growth will then soon catch up with the taller sections, and the amount of water overflowing the rim around the circumference of outlet 920 will again be equalized. The area 1191 of outlet 920 on pole mount reservoir 410 might be equal to or greater than the area of the reservoir compartment's water surface (not shown) on the inside of pole mount reservoir 410, or the area 1191 of outlet 920 might be less, such as 90%, 80%, 70%, 60%, or 50% of the area of the reservoir compartment's water surface. This reduced outlet 920 area reduces the volume of water required to completely overflow all portions of the rim of outlet 920.

Lastly there is the possibility of embodiment 1100 being self-stabilized at ground level 1170 solely from the weight of the water inside it with no base 510 or additional weights required. There are factors that the user has control over which also determine stability, such as the height of the ambient water surface level 130 (a lower water level 130 increases the relative weight and thus stability of pole mount reservoir 410) and the placement of illumination devices on one, two or multiple sides of pole mount reservoir 410 (algal growth on one side would be least stable whereas growth on all sides would be most stable), however the stability is generally sufficient when the height-to-diameter ratio is less than 2 when the height of ambient water surface level 130 is below half the height of pole mount reservoir 410. For example if the height of pole mount reservoir 410 is 30 cm (from bottom 1195 to outlet 920) and the inside diameter is 15 cm, and if the ambient water surface level 130 is 15 cm (half the height of pole mount reservoir 410), then the weight of the water inside pole mount reservoir 410 when operating should by itself provide enough stability to keep pole mount reservoir 410 in a vertical operating position without additional weights or braces, and without base 510 being needed. This is especially true if pump 210 is disposed inside and at the bottom of pole mount reservoir 410. This simplicity enables pole mount reservoir 410 to be constructed with just a single section of circular or square tubing, sealed at the bottom 1195 at ground level 1170. If water pump 210 is disposed in the bottom of pole mount 410 then the entire structure 1100 can be lifted out and taken to a sink for cleaning without having to disconnect anything.

Also with regards to weight is the advantage that embodiment 1100 has when water pump 210 is turned off; water drains back out of pole 410 via pump 210 or via a separate small drain hole (not shown), and this removes a large amount of weight from embodiment 1100. This is important for sump areas with fragile equipment, so pole 410 can be removed for cleaning without knocking other things over. If pole 410 is made of lightweight and thin wall pvc pipe such as type "SDR-35" sewer drain pipe, then a 6" (15 cm) diameter of height 24" (60 cm) would only weigh about 2 kg when empty, compared to 12 kg when full. This full-to-empty ratio is 6 and is typical of embodiment 1100 because almost all of the structure is used for water containment internally and growth surface externally. Other full-to-empty weight ratios might be 5, 4, 3, or 2 for smaller diameter reservoirs 410 because more weight of material is used for a given size of reservoir, or 8, 10, 12, 15, 20 or 30 for larger diameter reservoirs 410 because less weight of material is used for a given size of reservoir.

Maximizing effectiveness with minimal material can also be achieved by defining that embodiment 1100 have a high amount of internal water reservoir volume compared to external algal attachment area, especially when the embodiment is not a simple cylindrical pipe. For example a 100 cm tall volcano decoration as described above with an external algal attachment surface 1130 area of 10,000 square cm with a common 1" (2.5 cm) diameter water pipe 410 (water volume=490 cubic cm) inside it would have a volume/area ratio of 0.049 which is very low. However if a 6" (15 cm) diameter pipe 410 were used instead (water volume=17,663 cubic cm) then the ratio would become 1.77 which is much higher. And the larger pipe would have a more realistic larger water outlet 920 at the top of the volcano decoration which would further provide benefits no clogging or water shooting into the air. Other types of decorations or structures might have less external area, thus the volume/area ratio would be higher. A straight cylindrical pipe with no decorations has the highest ratio (6" pipe ratio=3.75 and 1" pipe ratio=0.62) and larger diameter pipes have higher ratios than smaller diameter pipes, but the ratio should generally be more than 1.0 including decorations.

If the user has a very crowded sump with no room for base 510 or even a large diameter reservoir 410, it may be desired to have a narrow but tall embodiment 1100. It is contemplated that stability in this situation might be obtained by attaching a hanging means such as a wire or rope to an upper section of reservoir 410 near outlet 920; the other end of the rope might be attached to the roof of the cabinet where the sump is located. Further, embodiment 1100 might actually be hung from this rope such that no part of reservoir 410 touches the sump; instead bottom 1195 could be at or just above or below ambient water surface level 130 and could actually be above other equipment in the sump so that no open space on the floor of the sump is needed at all for pole 410. A very low cost version of this would be embodiment 1100 hanging from the hose that drains water from the aquarium down into the sump; a simple cylindrical bucket 410 with it's own hanging means would suffice as reservoir 410, with algal attachment material 1140 attached to the exterior 1160 of the reservoir bucket 410, and an aquarium drain hose inserted into the reservoir bucket 410 through opening 920. The water capacity of the reservoir bucket 410 could be reduced to limit the hanging weight, and the attachment material 1140 could be lengthened beyond the bottom of reservoir bucket 410 so there would be more surface 1130 for algal growth to attach to and for illumination source 1145 to illuminate. It might appear to be a hanging mop.

Tall narrow embodiments are also useful if the user wishes to operate the apparatus outdoors using solar illumination. Pole 410 could be set up similar to fence posts, as tall as the user requires; this makes the most use of solar illumination because narrower that pole 410 is, the less shadow is casts on poles behind it, and the pole does not need to be a minimum diameter in order to capture the most illumination from an artificial illumination bulb source; solar light is free. Common fence materials be used such as hollow vinyl fence posts in 4", 5" or 6" (10, 12.5 or 15 cm) diameter sizes. After macroalgal attachment surfaces are added to the exterior of these posts they can be positioned relatively near each other so they can still grow substantial algae with solar illumination alone. Example dimensions of these posts 410 are 150 cm tall, and 15 cm outside diameter, giving a height-to-diameter ratio of 10. Other height-to-diameter ratios such as 15, 20, 25 or 30 make better use of the available ground area.

If the user wishes to reduce the overall area that algae grows on pole 410 because of smaller filtering needs or lack of water pump capacity, it is envisioned that partial or positional dam segments could be placed at outlet 920 such that water only flows down over a portion of the circumference of pole 410. Cap 1196 would accomplish this, however the top of cap 1196 is closed. If the user prefers to keep water outlet 920 open so as to be able to reach down into pole 410, then extending wall 1150 upwards in some sections of outlet 920 but not others would confine water flow to the desired sections. These extended upward sections of wall 1150 could be individual segments that could be added or removed from outlet 920, thus allowing for adjustable flow levels and direction, or a cap 1196 could be used which itself has a removable top, thus keeping opening 1197 in place to alter water flow but allowing the user to reach into pole 410 from the top. Changing algal attachment 1130 area and/or pole 410 height can also be accomplished with an adjustable-height pole 410, possibly with a telescopic 2-section pole 410; these section could slide over one another and be locked down or glued by the user into position. A telescoping movement of pole 410 could also be achieved by a screw rotation of one section of pole 410 into the other section, and the needed screw threads might be molded into the material that pole 410 is made of.

Decorations can alter the stability. If the decorations are above ambient water surface level 130 then the extra weight of the decoration (and the water flow on it) farther away from the vertical axis of mount 410 will reduce stability, and thus lighter materials such as foam might be used and the thickness of the decoration minimized. If the decorations are below ambient water surface level 130 then the decorations should set on ground level 1170 and should be more dense than water so as to increase stability.

Macroalgal attachment material 1140 could be any material or surface in the art which enables substantial amounts of macroalgal (seaweed) growth 520 to attach and grow. For example, roughened plastic canvas in 1-3 mm thickness with 5-10 grids per inch as described in applicant's U.S. Pat. No. 9,115,008 could be permanently or removably secured to the exterior of pole 410. If removable, the roughened plastic canvas could be removed for cleaning/harvesting without needing to remove pole 410 or turn off pump 210. Material 1140 might be attached to pole mount reservoir 410 by friction fit, or supported by a lip at the bottom 1175 of material 1140 such that material 1140 could be lifted off of pole mount reservoir 410. If pole 410 is square or rectangular, then material 1140 might just be a flat sheet the roughened plastic canvas which hangs on a flat side of mount 410. Material 1140 might be rigid so as to maintain it's shape (in FIG. 11, cylindrical) when removed, or it might be flexible or cloth-like, such that it can be flattened and scraped on a flat surface. Another material 1140 might be sand or small gravel of grain size 1-3 mm glued to pole 410 or to a sheet of plastic which is then wrapped around pole 410. Yet another material 1140 might be a woven non-organic cloth such a polyamide (nylon) or fiberglass cloth in a very coarse 10-20 threads per inch density. Material 1140 might alternately be a 3D printed grid as described later in this application. Or material 1140 might simply be a roughened portion of the exterior surface 1160; this simplifies construction and does not require disassembly however it requires either that the cleaning/harvesting be done while still in the sump, or that the entire apparatus 1100 be removed, possibly leaving only the pump 210 in the sump. To achieve a rough enough surface 1130 which allows macroalgal seaweed to attach, simple sanding of the exterior surface 1160 is not sufficient because heavy macroalgal seaweed growth 520 will fall off (thick growth can become 5 cm thick and weigh several kg per square meter). Instead, deep rough cuts 1130 will need to be made into the material of pole 410 such that shards or edges of the material stick out laterally 1-3 mm from exterior surface 1160; this type of roughened surface 1130 sometimes resembles a cactus. If mount 410 is decorated such as the volcano described above, then material 1140 might be removable landscape textures that are or resemble sand or gravel.

If apparatus 1100 is to be operated in a sump with water level 130 then it is preferred that rough surface 1130 be above water level 130 (shown approximately at height 1175) and not below it, so that debris circulating in the sump water will not be caught by surface 1130. Rough surface 1130 would thus be only on an upper portion of pole 410. It is also envisioned that pole 410 might be utilized as the means of transferring water from the sump back up to the aquarium above it, and from the aquarium back down to the sump. In previous art, this transfer function was usually done by a separate pump (not shown), often called a "return pump" which pumped water from the sump up to the aquarium where the water then went through an overflow in the aquarium and then down through a drain hose back down to the sump. However embodiment 1100 can be utilized for this transfer function, thus eliminating the extra return-pump and extra overflow hose. To accomplish this, water pump 210 becomes the "return" pump, and pumps water into the bottom of pole 410 which then transfers this water up the inside of pole 410 to outlet 920 located in the aquarium above (water does not immediately overflow down pole 410). Only after circulating within the aquarium above does the water then overflow from the aquarium down the outside of pole 410, flowing down algal attachment surface 1130. A water divider mechanism can be affixed to water outlet 920 to cause this desired flow pattern into and out of the aquarium; such a water divider mechanism is usually a wall with separate passages on each side of the wall. Pole 410 can also be made to be easily removed for cleaning/harvesting of growth from it, and pump 210 does not need to be turned off during cleaning because water will just recirculate in the sump. If pole 410 is utilized in this manner, rough attachment surface 1130 might only be on a lower portion of pole 410 such that the entire height of pole 410 need not be illuminated.

The diameter of pole mount reservoir 410, other than being sized for a particular size of aquarium or sump, should be such that water overflowing in the direction of arrow 1110 be capable of completely overflowing the entire circumference of the rim of outlet 920 at normal operating water flow and subsequently also be capable of flowing down completely over all macroalgal attachment surface area 1130 completely around the circumference of attachment surface 1130 all the way around exterior surface 1160. Generally this water flow (provided by water pump 210 or by another source) is at least 60 lph (liters per hour) per centimeter of overflow circumference. For example a pole mount reservoir 410 with outside diameter of 15 cm (radius of 7.5 cm) has an overflow circumference of 2(pi)(7.5)=47.1 cm and thus should have a minimum total water flow of 60(47.1)=2826 lph. Similarly, a square shaped pole mount reservoir 410 with each side measuring 15 cm would have a total overflow circumference of 4(15)=60 cm, and thus would require at least 60(60)=3600 lph of total water flow. The diameter of pole 410 also has an effect on receiving illumination from illumination sources such as LED 1145 because a tall and narrow structure of embodiment 1100 would tend to allow some illumination to miss algal attachment surface 1130. Thus by reducing the height-to-diameter ratio to below 2 as described above, the portion of embodiment 1100 above the ambient water surface level 130 will be wider and thus will receive more of the illumination. It is also contemplated that the height-to-diameter ratio might be less than 3, 4, 5 or 6. If decorations are added to the exterior of wall 1150 such as the example volcano described above (which is wider at the bottom than at the top) then the water flow may not completely cover all exterior surfaces 1130 at the bottom because of the much larger surface area there, even though the flow does covers all surfaces 1130 at the top.

An alternate embodiment of 1100 might change water inlet 910 to be at the top of pole mount 410 so that there is just one opening 920, such that water enters pole mount reservoir 410 from the top instead of from the bottom. In this case water is poured into outlet 920 from above, or a water supply source tubing might be inserted into outlet 920. If a water supply source tubing is inserted into outlet 920 then the tubing might extend partially down into pole mount reservoir 410 or the tubing might extend substantially to the bottom of pole mount reservoir 410. Extending further down into pole mount reservoir 410 gives less turbulence at outlet 920 because the water has a longer vertical distance to travel upwards before overflowing outlet 920 and has had more time to reduce any swirling or random motions, thus leveling the flow pattern overflowing outlet 920. A more even flow pattern overflowing outlet 920 helps equalize algal growth on all sides of pole mount reservoir 410. The water however still achieves a turbulent air/water interface motion when it falls down attachment surface 1130 thus maximizing photosynthetic growth and filtering.

Another alternate embodiment of 1100 has macroalgal attachment material 1140 located below pole mount reservoir 410 instead of on the side of pole mount reservoir 410. This is possible if base 510 or a separate bracket (not shown) elevates pole mount reservoir 410 such that the bottom 1195 of pole mount reservoir 410 is above ambient water surface level 130. This allows water to cascade off the bottom 1195 of pole mount reservoir 410, and thus if macroalgal attachment material 1140 were disposed below pole mount reservoir 410 then the water would travel out of outlet 920, down surface 1160, then down to the attachment material 1140. It is contemplated that base 510 could be discrete supporting legs, such as for a table, and this would enable attachment material 1140 to be wrapped around the legs like a fence, and an additional illumination source placed inside the legs which would then provide illumination on both sides of macroalgal attachment material 1140. Attachment material 1140 could also be placed both below and on the sides of pole mount reservoir 410. If material 1140 is string or ribbon as shown in FIGS. 9A-9E of co-pending U.S. utility patent application Ser. No. 14/380,926 then water will flow on both the inside and outside of the material 1140.

Yet another alternate embodiment of 1100 might have base 510 made of supporting legs with the attachment material positioned within the legs instead of around the legs, and pole mount reservoir 410 shaped in a pointed fashion, pointing down, such that water flowing down exterior surface 1160 converges at the bottom 1195 of pole mount reservoir 410 and thereby transfers to attachment material 1140.

Illumination of pole mount reservoir 1100 could be solar if the apparatus were outside or near a window. For artificial illumination, any suitable illumination source could be utilized, especially long narrow sources such as fluorescent tubes or strings of LEDs (light emitting diodes) 1145 because they would complement the shape of pole mount reservoir 410. If decorated, such as a volcano, then various illumination sources 1145 could be placed around the circumference of reservoir 410.

Figure 12:
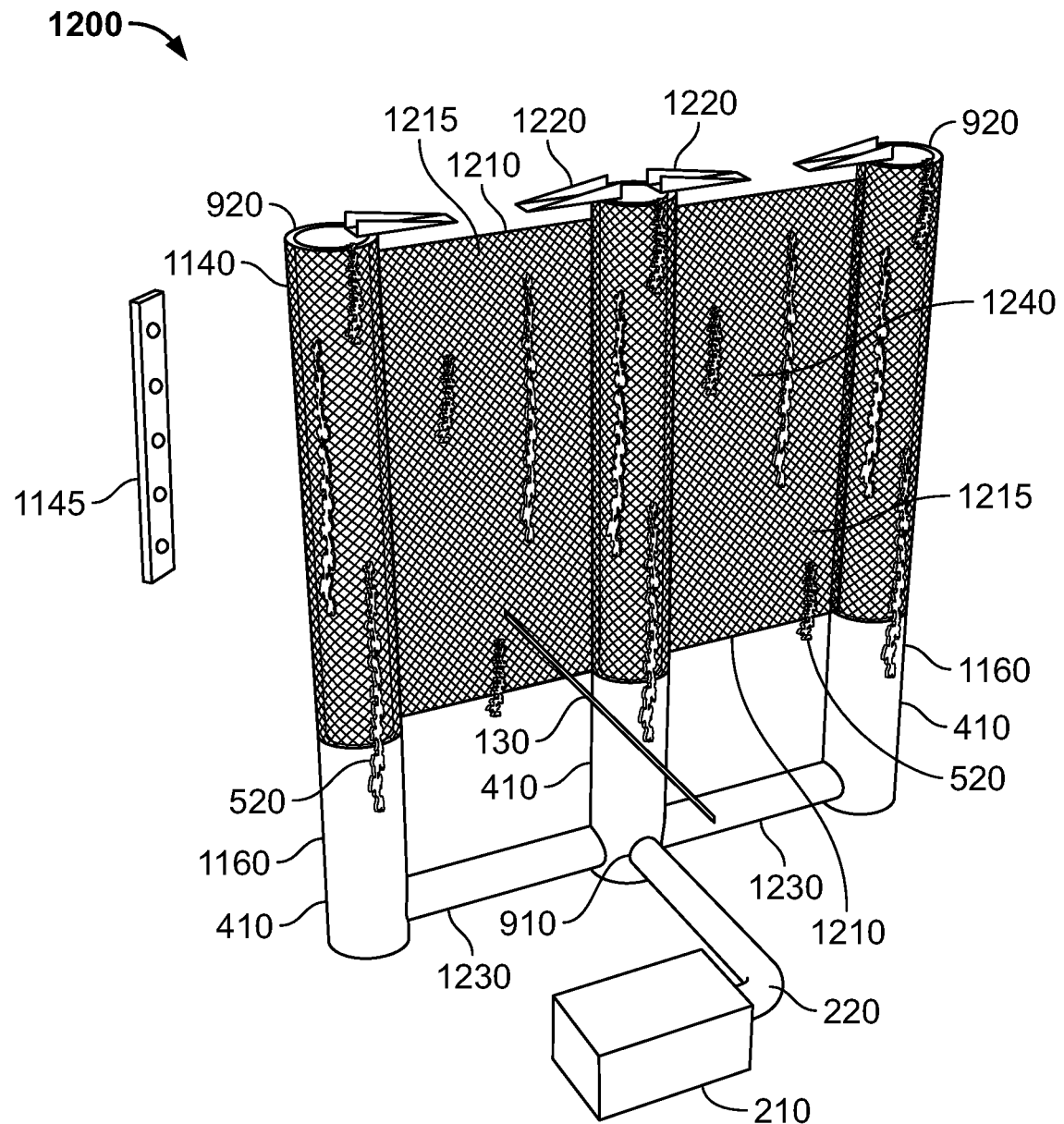
FIG. 12 shows a perspective view of another pole mount reservoir overflow embodiment of the current invention.

FIG. 12 shows an embodiment 1200 of the current invention which utilizes multiple pole mount reservoirs 410 to support a bridging macroalgal attachment material 1210 which has a bridging macroalgal attachment surface 1215. Embodiment 1200 also supplements water flow to middle sections 1240 of bridging macroalgal attachment material 1210 by utilizing water delivery structures 1220 which may be attached to pole mount 410 by any conventional means such as glue, welding, or friction fit. Because there is no waterfall delivery pipe with an orifice slot as was utilized in previous art FIG. 2 and FIG. 10, there is nothing to clog with growth. Instead water delivery structures 1220 of the current embodiment 1200 of FIG. 12 cannot clog because any growth on a water delivery structure 1220 simply causes water to flow up and over it where the water still falls into contact with bridging macroalgal attachment surface 1215. The growth cannot stop the water.

Utilizing bridging macroalgal attachment material 1210 also allows for 2-sided macroalgal attachment instead of 1-sided. When algal growth 520 gets more than a few millimeters thick it begins to self-shade, such that the "root" layers of growth which attach to attachment surface 1215 receive less illumination and water flow than newer outer layers of growth do. This causes less growth for the important root attachment layers, and if illumination and water flow are reduced enough then the root layers will completely detach and flow away with the water. Thus by utilizing a thin bridging macroalgal attachment material 1210 and providing water flow and illumination devices 1145 on both sides of material 1210, the roots of the macroalgae 520 will be kept alive and in full attachment for a longer period of time such that the algae can be cleaned/harvested properly instead of falling off prematurely onto the ambient water surface level 130 (represented by line 130). This 2-sided concept is explained further in FIGS. 13A, 13B and 13C below.

Water pump 210 pushes water through water supply source tubing 220 into a pole mount reservoir 410 through water inlet 910, where the water is then divided into delivery pipes 1230 to the adjacent pole mount reservoirs 410. However water supply source tubing 220 could instead have been itself divided using a standard pipe divider so that water flowed through multiple water supply source tubings 220 into each water inlet 910 of each pole mount reservoir 410. Water then travels up the internal reservoir compartments (not shown) of each of the pole mount reservoirs 410 where the water then exits water outlets 920, then the water both overflows the rims of outlets 920 and also comes into fluid communication with water delivery structures 1220 which direct the water to flow laterally away from the exterior surfaces 1160 of pole mount reservoirs 410 such that central portions 1240 of the bridging macroalgal attachment surfaces 1215 are contacted by the water. Thus the water delivery structures 1220 enable water to reach more bridging attachment surface 1215 than would otherwise occur. The flowing water, rough attachment surfaces, and illumination source 1145 cause algae to attach and grow, removing nutrients from the water.

Embodiment 1200 works well in solar illuminated outdoor pond applications because the large bridging material surface area captures sunlight well and can also be used as a fence to hold livestock. Pole mounts 410 cannot clog; a clog could be troublesome if the algae scrubber 1200 is not easily accessible such as in the middle of a pond. Algal attachment material (1210, 1140) could be designed to slide upwards off of pole mount reservoirs 410 for cleaning/harvesting, or embodiment 1200 might not be cleaned/harvested at all. Non-cleaning of algae scrubbers changes their purpose from nutrient removal devices to nutrient conversion devices; nutrients in the water are simply converted from inorganic (ammonia, nitrite, nitrate, phosphate, $CO_2$) into organic food for the livestock, thus keeping the water chemically "clean". Freshwater growth 520 tends to be long and stringy, which flows down to the pond water level 130 and gets eaten by the livestock, and growth 520 above the pond water line 130 tends to get consumed by snails that travel upwards. So a solar illuminated pond embodiment 1200 can be self-filtering and self-feeding once set up, only requiring a water pump 210 and tubing 220.

FIG. 13A shows an example of a 2-sided macroalgal attachment material 240 (further described in applicant's U.S. Pat. No. 9,115,008 as used for an upflow version) supplied by water from a water source (not shown) from above material 240. Arrow 1315 shows how illumination reaches the front side of macroalgal attachment material 240, and arrow 1316 shows how illumination reaches the back side of macroalgal attachment material 240. Water flow (not shown) flows down both sides of material 240. Arrow 1316 is shown partially visible through material 240, emphasizing the open or porous nature of material 240. This open or porous structure allows illumination and water from the front of material 240 to also partially reach the back of material 240, and vis versa. Macroalgal growth 520 is shown partially hanging off the bottom of material 240, however it often starts its growth in thin layers which cover material 240 completely like a blanket; thus if arrow 1315 were illumination, it and water flow would have difficulty reaching the front surface of material 240 when growth 520 became thick across the whole width of material 240. It is at this time that illumination represented by arrow 1316, and also water flow from the back side of material 240, penetrate material 240 to aid in keeping the algal roots alive on the front of material 240. And the process is the same for illumination and water from the front of material 240 aiding the roots on the back of material 240. It has been shown that this 2-sided construction can add up to a week of time before the "roots" begin to die and detach due to lack of illumination and water flow reaching the roots. This greatly increases (doubles) filtering capacity for the same size of apparatus.

FIG. 13B shows an example of a 1-sided macroalgal attachment material attached to a rectangular pole mount reservoir structure; the attachment material is fed by water overflowing out of outlet 920. The walls of the structure are opaque, including left wall 1340 and front wall 1345, thus illumination represented by arrow 1335 on the left wall and 1336 on the front wall does not travel through the attachment material. Nor does water. So when growth (not shown) gets thick on the attachment material, the roots which are nearest to the opaque walls of the structure will begin to die sooner than growth on FIG. 13A.

FIG. 13C shows another example of a 1-sided macroalgal attachment material attached to a cylindrical reservoir structure, the attachment material is fed by water overflowing out of outlet 920. Cylinder wall 1365 is opaque as in FIG. 13B, so no illumination or water travels through the wall; illumination (represented by arrows 1370 and 1371) and water flow are stopped.

FIGS. 13A, 13B and 13C also demonstrate "perpendicular access" for cleaning/harvesting. The same arrows 1315, 1316, 1335, 1336, 1370 and 1371 that represented illumination are also used here to represent the user reaching to the macroalgal attachment material to clean or harvest it. Perpendicular access is defined to mean the user having substantially open access to reach perpendicularly (or normal) to the growth surface, in the direction of the arrows. For example in FIG. 13A the user would have perpendicular access to the front or back of material 240 all the way across the material (even though the arrows are only on the left side of the material); in FIG. 13B the user would have perpendicular access to all four sides of the structure (even though only two arrows are shown); and in FIG. 13C the user would have perpendicular access all the way around the circumference of the cylinder (even though only two arrows are shown). In FIG. 13C especially, there would be substantially no part of the structure of the waterfall apparatus on the sides of the cylinder that would prevent perpendicular access from any direction.

When applied to illumination domes as described in earlier figures, perpendicular access can be measured when the dome is in the first and second positions. Looking at FIG. 13A from the front, e.g. viewing from the direction of arrow 1315, the macroalgal attachment material has an area that is its width multiplied by height. As shown in FIG. 13A which has no illumination dome, perpendicular access to material 240 would be 100% because all the area of the material is reachable. However if an illumination dome were placed on tray 330 in a first position, and the dome covered half of the width of material 240 such that only half the width were viewable and reachable, then the illumination dome would prevent perpendicular access to 50% of the attachment material. And of course if an illumination dome completely covered all of material 240 in the first position but allowed full access to all of material 240 when the dome was removed to a second position, then perpendicular access would be 0% in the first position and 100% in the second position. Perpendicular access is important for the cleaning and harvesting of algae scrubbers because it defines how many steps will be needed to obtain access to the growth; the less steps, the better.

Lastly, FIG. 13A also shows macroalgal settlement structure 330 supporting attachment material 240. Material 240 is shown here rigid and attached to tray 330 using glue (not shown) or another standard attachment mechanism. Material 240 might instead be flexible and held up with vertical braces (not shown) attached to tray 330. Material 240 might be several rigid upright structures, possibly with added weight that set on tray 330 and thus do not require a fastening mechanism. Being attached to or set on tray 330 instead of a water delivery structure ensures that macroalgae 520 will not be torn apart when tray 330 and material 240 are removed for cleaning/harvesting. Drain orifice 820 continues to allow drainage of water from tray 330, when tray 330 collects algal growth.

Example Claims—Reservoir Overflows

1. An overflowing reservoir apparatus for supplying water to a macroalgal attachment surface, comprising:
   a first reservoir structure (410), the first reservoir structure defining a first reservoir compartment, a first water inlet, and a first water outlet defining a first rim with a first circumference, the first reservoir compartment having a height and a diameter;
   a first macroalgal attachment material defining a first macroalgal attachment surface;
   a first attachment mechanism, the first attachment mechanism to position the first macroalgal attachment material such that water flowing out of the first water outlet flows down an external surface of the first reservoir structure and makes contact with the first macroalgal attachment surface.

2. The apparatus for supplying water of claim 1, wherein the first reservoir structure supports itself from ground level (1170).

3. The apparatus for supplying water of claim 1, wherein an external surface of the first reservoir structure and an internal surface of the first reservoir compartment are two sides of a same wall.

4. The apparatus for supplying water of claim 1, wherein the first rim of the first water outlet defines a plane, the plane being substantially horizontally level such that an amount water flowing out of the first water outlet is substantially equal around the entire circumference of the first water outlet.

5. The apparatus for supplying water of claim 4, wherein the first macroalgal attachment material encircles the exterior surface of the first reservoir structure such that water flows down substantially equally around the circumference of the first macroalgal attachment surface.

6. The apparatus for supplying water of claim 1, wherein the first water outlet is open to the atmosphere.

7. The apparatus for supplying water of claim 6, wherein an area (1191) of the first water outlet is at least 50% of an area of the water surface inside the first reservoir compartment.

8. The apparatus for supplying water of claim 1, wherein a height to diameter ratio of the first reservoir compartment is less than 6.

9. The apparatus for supplying water of claim 1, wherein a ratio of first water outlet area (1191) to a reservoir compartment water surface level height is less than 3.

10. The apparatus for supplying water of claim 1, wherein the first water inlet is the first water outlet.

11. The apparatus for supplying water of claim 1, wherein a first water supply source tube is placed into the first water outlet.

12. The apparatus for supplying water of claim 11, wherein the first water supply source tube extends substantially to the bottom of the first reservoir compartment.

13. The apparatus for supplying water of claim 1, wherein the first macroalgal attachment material is positioned on a side external surface of the first reservoir structure.

14. The apparatus for supplying water of claim 1, wherein the first macroalgal attachment material is positioned below a bottom (1195) of the first reservoir structure.

15. The apparatus for supplying water of claim 2, wherein the weight of the first reservoir structure provides sufficient stability to keep the first reservoir structure in upright operating position when the first reservoir compartment is filled with water and the ambient water surface level is less than half the height of the reservoir structure.

16. The apparatus for supplying water of claim 1, further comprising:
   a second reservoir structure, the second reservoir structure defining a second reservoir compartment, a second water inlet, and a second water outlet defining a second rim;
   a second macroalgal attachment material defining a second macroalgal attachment surface;
   a bridging macroalgal attachment material defining a bridging macroalgal attachment surface;
   a second attachment mechanism, the second attachment mechanism to position the second macroalgal attachment material such that water flowing out of the second water outlet flows down an external surface of the second reservoir structure and makes contact with the second macroalgal attachment surface.
   a third attachment mechanism, the third attachment mechanism to secure the bridging macroalgal attachment material to the first and second reservoir structures and to align the bridging macroalgal attachment surface such that a portion of the water which flows out of the first water outlet and a portion of the water which flows out of the second water outlet makes contact with the bridging macroalgal attachment surface.

17. The apparatus for supplying water of claim 16, further comprising:
   a water delivery structure,
   a water delivery structure attachment means, the water delivery structure attachment means to secure the water delivery structure to a reservoir structure and to position the water delivery structure such that it receives water flowing out of a water outlet and delivers a portion of the water to the bridging macroalgal attachment surface.

18. The apparatus for supplying water of claim 1, wherein a ratio of a first water outlet area to a first water inlet area is at least 5.

19. The apparatus for supplying water of claim 1, wherein the first macroalgal attachment surface is circular with a larger circumference at the bottom of the first reservoir structure than the top of the first reservoir structure.

20. The apparatus for supplying water of claim 3, wherein a thickness of the wall is less than 10 mm.

21. The apparatus for supplying water of claim 1, wherein a ratio of weight of the apparatus when full of water to a weight of the apparatus when empty of water is greater than 2.

22. The apparatus for supplying water of claim 1, wherein a ratio of first reservoir compartment volume to first macroalgal attachment surface area is at least 1.

23. The apparatus for supplying water of claim 1, wherein the first macroalgal attachment surface is a portion of an external surface of the first reservoir structure.

24. The apparatus for supplying water of claim 1, wherein the first macroalgal attachment material is removable from the first reservoir structure.

25. The apparatus for supplying water of claim 1, further comprising a water divider mechanism, the water divider mechanism to route water from the first water outlet into an aquarium, and from the aquarium to the first macroalgal attachment surface.

26. The apparatus for supplying water of claim 1, further comprising positionable dam segments.

27. The apparatus for supplying water of claim 2, wherein the height of the first reservoir structure is adjustable.

28. The apparatus for supplying water of claim 27, wherein the height adjusts telescopically.

29. The apparatus for supplying water of claim 28, wherein the telescopic height adjustment is accomplished with screw threads.

30. The apparatus for supplying water of claim 10, further comprising a hanging means, the hanging means to support the reservoir structure.

31. The apparatus for supplying water of claim 1, further comprising a water pump.

32. The apparatus for supplying water of claim 31, wherein the water pump is internal to the reservoir structure.

33. The apparatus for supplying water of claim 1, further comprising:
   an illumination source;
   a bracket, the bracket to position the illumination source external to the first reservoir structure such that illumination from the illumination source reaches the first macroalgal attachment surface.

34. An apparatus for supplying water to a macroalgal attachment surface substantially as hereinbefore described with reference to FIGS. 11-13C.

Water Pipe Screen Removal

In the previous art waterfall of FIG. 10, when algal growth 520 grew up into water delivery structure 230 (a water pipe) the growth would clog the water outlet (not shown) and require that the entire structure 230 be removed for cleaning. As shown in previous art FIG. 2, the entire apparatus needed disassembly, and the water supply source turned off, so that attachment material 240 could be removed and the inside of water delivery structure 230 cleaned out. If that algae scrubber structure were not disassembled, growth 520 would just be pushed further up into the slot in water delivery structure 230.

FIG. 15A shows an embodiment 1500 of the present invention which offers a solution to this problem. By modifying structure 230 such that part of the structure itself moves away from outlet 920, attachment material 240 can be removed and the inside of structure 230 can then be cleaned without disassembly of the algae scrubber and possibly even without turning off the water supply source. Operation is as follows: Water delivery structure 230, which in this embodiment is a water pipe 230, is in operating position. It is a perspective view looking through pipe 230, and the pipe is open on both ends for clarity. In actual operation, one end of pipe 230 is closed and the other end is a water inlet connected to a water supply source. As water enters pipe 230, the water exits water outlet 920 which is shown as slot 920 at the bottom of pipe 230. This slot 920 would be similar to the slot (not shown) on the previous art algae scrubber in FIG. 10, however in FIG. 10 there is no way to enlarge the slot because it is just cut into pipe 230. The embodiment of FIG. 15A however includes water outlet structure 1530, which is shown as part of pipe 230 that has been cut out at water outlet border 1520. Because water outlet structure 1530 is still in position within, and abutting, water outlet border 1520, the water outlet structure 1530 defines a portion of water outlet 920. Water pipe 230 defines the remaining portion of water outlet 920. And because water outlet structure 1530 cannot move downwards because of tab 1550, water outlet structure 1530 is locked into a first position by water pressure inside pipe 230. As water flows down macroalgal attachment surface 241, surface 241 is illuminated by illumination source 1145 thus causing algal growth on material 240.

Positioned in outlet 920 is macroalgal attachment material 240 which defines macroalgal attachment surface 241; material 240 is shown here as a screen hanging down from outlet 920, and also as mounting blocks above outlet 920 to keep screen 240 from falling. However material 240 could be any shape which fits into outlet 920 securely and allows water to flow out of outlet 920. Water outlet structure 1530 cannot move downward because of mechanical stops 1550 that are in place, thus water flows out of outlet 920 and down screen 240 into the area of illumination source 1145.

FIG. 15B shows water outlet structure 1530 moved upwards to a second position and attachment material 240 removed downwards from pipe 230. Unlike previous art FIG. 10, the current embodiment 1500 in FIG. 15B does not require any disassembly at all; instead water outlet structure 1530 is pushed upwards into pipe 230 via positioning means 1540 which in this case is a hinge. Once outlet structure 1530 is moved upwards to second position, attachment material 240 is enabled to be removed downwards through water outlet border 1520. No disassembly of structure 230 is required and it is also not required to turn off the water supply source because the water would simply continue to flow down out of water outlet border 1520 into a sump (not shown) below as it was doing anyway. And it can be seen again in FIG. 15B that attachment material 240 includes the protruding square mounting pegs at the top of material 240. These protruding mounting portions of material 240 are enlarged sections of material 240, possibly just a thickened screen 240; the square pegs are simply shown to demonstrate how a larger section of material 240 can be used to lock material 240 into position in pipe 230.

Water outlet structure 1530 and water outlet border 1520 can be any size or shape which, when water outlet structure 1530 abuts water outlet border 1520 in a first position as in FIG. 15A, secures an upper section of material 240 into pipe 230 such that the majority of material 240 hangs substantially below water outlet structure 1530 and also such that water which exits water outlet 920 is enabled to flow down attachment surface 241. "Below" is defined herein as the direction water will travel when poured. FIG. 15A shows water outlet border 1520 and water outlet structure 1530 to be a rectangular cutout of pipe 230; structure 1530 thus fits into pipe 230 like a door, being held in first (closed) position by a peg, lip or other protrusion 1550 from pipe 230, and this peg, lip, or other protrusion prevents structure 1530 from moving downwards. Structure 1530 can only move upwards into pipe 230 via positioning means 1540. Other shapes and sizes of border 1520, structure 1530, and positioning means 1540 are contemplated such as structure 1530 being larger than border 1520, or structure 1530 being weighted to hold itself in a locked downward first position thus requiring no hinge 1540, or structure 1530 being capable of rotating inside pipe 230 such that rotation in one direction locks material 240 into slot 920 in a first position and rotation in the opposite direction opens slot 920, or lastly that outlet structure 1530 is actually half of the entire pipe 230 (pipe cut in half lengthwise like a clam shell) with a hinge or other mechanism at the top of pipe 230 thus causing outlet 920 at the bottom to open when the pipe 230 is opened to a second position.

Alternately to moving up into water delivery structure 230, water outlet structure 1530 might move downwards to its second position, possibly becoming disconnected from structure 230. One example of this would be reversing the operating direction of positioning means 1540 such that the hinging action is downwards instead of upwards. Hinge 1540 might then be replaced entirely by a peg, lip, or other protrusion which prevents structure 1530 from moving up into pipe 230, thus allowing structure 1530 to only move down and away from pipe 230. In this case structure 1530 might be held into an upward operating first position by a releasable latch, or by flexible straps that go around pipe 230. Or as previously stated, structure 1530 could move rotationally, this time along the outside of pipe 230 much like a larger pipe over a smaller pipe. Any of these positioning means allow water outlet 920 to be opened up and material 240 to be removed for cleaning and un-clogging without requiring any disassembly of the rest of the algae scrubber apparatus as was needed in previous art FIGS. 2 and 10.

Figures 16A, 16B:
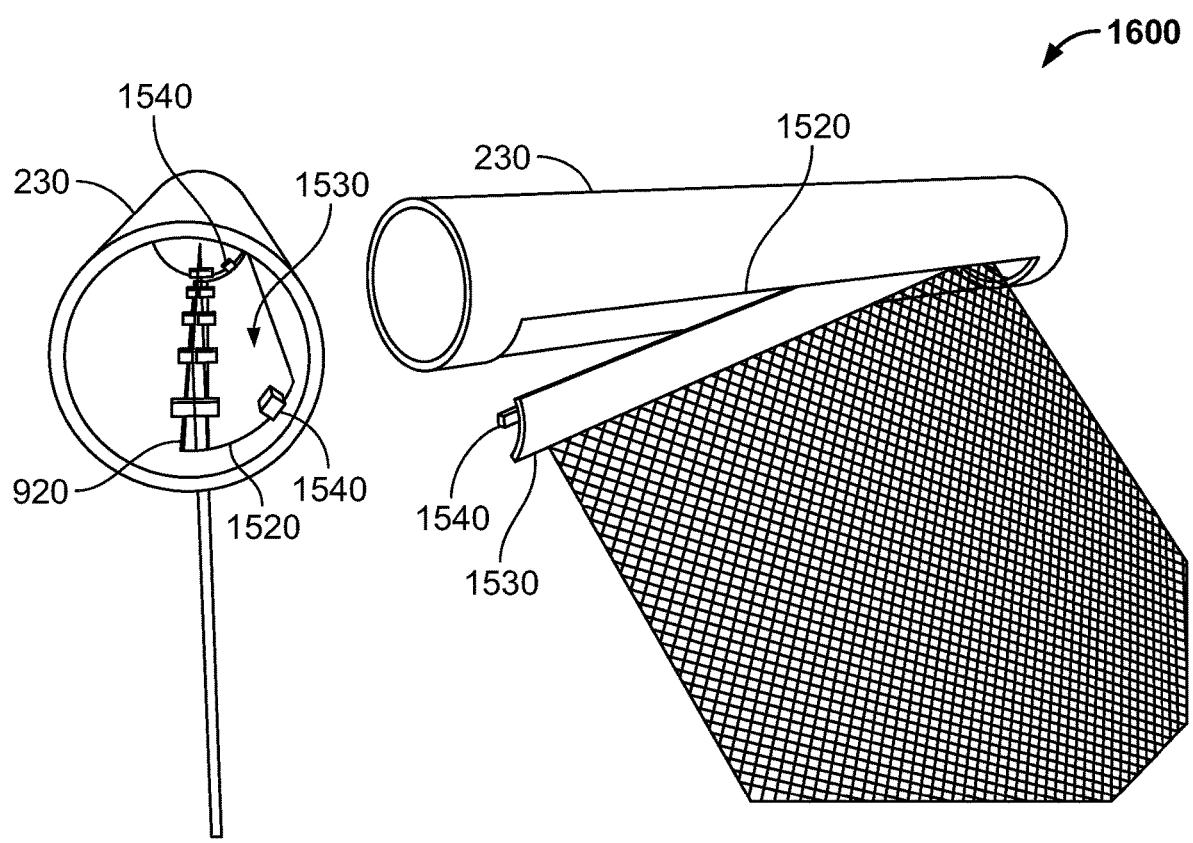
FIG. 16A shows a perspective view of another screen-release embodiment in a water pipe, of the current invention.
FIG. 16B shows a perspective view of the screen-release embodiment of FIG. 16A, with the screen removed.

FIG. 16 shows an embodiment 1600 where water outlet structure 1530 is combined with macroalgal attachment material 240, thus forming a single unified component. Although simply shown "glued" together, they are a smoothly transitioning seamless molded component. Of note in FIG. 16A is that the positioning means hinge 1540 of FIGS. 15A and 15B has been replaced by positioning means pegs 1540 in FIG. 16. Because pegs 1540 are not attached to pipe 230, the entire water outlet structure 1530 and attachment material 240 combination can be removed together. However, positioning means 1540 prevents structure 1530 from coming directly out of pipe 230; instead, structure 1530 must be pushed upwards into pipe 230 and then moved lengthwise inside pipe 230, and then one end of structure 1530 can be removed downward out of pipe 230 as shown in FIG. 16B. This single unified component (structure 1530 and material 240) allows it to be easily molded into one removable part, sized and shaped such that it fits up and locks into pipe 230 yet removes easily for cleaning of material 240 and outlet 920.

An alternate way of removing unified structure 1530 and material 240 from pipe 230 is to make the unified component with flexible material such as a flexible rubber or resilient plastic. Thus the unified component (structure 1530 and material 240) could be somewhat compressed like a sponge, and then removed from pipe 230, and after cleaning could be compressed again and put back into water outlet border 1520 and released so as to allow the unified component (structure 1530 and material 240) to expand back into a locking position inside pipe 230.

Example Claims—Water Pipe Screen Removal

1. An apparatus for releasably supporting macroalgal attachment material and supplying water to a macroalgal attachment surface, comprising:
    a macroalgal attachment material defining a macroalgal attachment surface;
    a water delivery structure defining a water outlet border;
    a water outlet structure, the water outlet structure movable from a first position to a second position and defining a portion of a water outlet when in the first position.
    a positioning means, the positioning means to position the water outlet structure in the first position abutting the water outlet border such that the macroalgal attachment material is secured substantially below the water outlet structure and water from the water outlet contacts the macroalgal attachment surface, and further to enable movement of the water outlet structure to the second position such that the macroalgal attachment material may be removed from the water delivery structure.
2. The support and release apparatus of claim 1, wherein the water outlet structure abuts a top inside surface of the water outlet border.
3. The support and release apparatus of claim 1, wherein the water outlet structure abuts a bottom outside surface of the water outlet border.
4. The support and release apparatus of claim 1, wherein the positioning means defines a hinge.
5. The support and release apparatus of claim 1, wherein the water outlet structure slides laterally from the first position to the second position.
6. The support and release apparatus of claim 1, wherein the water outlet structure rotates from the first position to the second position.
7. The support and release apparatus of claim 6, wherein the water outlet structure rotates inside the water delivery structure.
8. The support and release apparatus of claim 6, wherein the water outlet structure rotates outside the water delivery structure.
9. The support and release apparatus of claim 1, wherein the water outlet structure defines at least one panel.
10. The support and release apparatus of claim 1, wherein the water outlet structure and macroalgal attachment material are a single unified component.
11. The support and release apparatus of claim 10, wherein the single unified component is flexible.
12. The support and release apparatus of claim 10, wherein the single unified component can be lifted from the first position to the second position and subsequently rotated and removed through the water outlet border.
13. The support and release apparatus of claim 1, wherein the positioning means defines tabs.
14. An apparatus for releasably supporting macroalgal attachment material and supplying water to a macroalgal attachment surface substantially as hereinbefore described with reference to FIGS. 15A-16B.

Reservoir Slots

While the water pipe screen removal embodiments above are useful for water pipes, an open-top reservoir embodiment described below may make screen cleaning easier because the user can reach into the reservoir from above and remove blockages without removing the screen, and might also be able to remove the screen in an upwards direction instead of downwards, which may help avoid crowded areas of a sump. In addition, surging of water inside of a water pipe during operation (regardless of how the slot is cleaned) often causes more water to flow out of one end of the slot than the other; the large amount of water in a reservoir, by contrast, gives water more time to reduce velocity before going through the water outlet and thus stabilizes the flow from one part of the water outlet to another.

Figure 14:
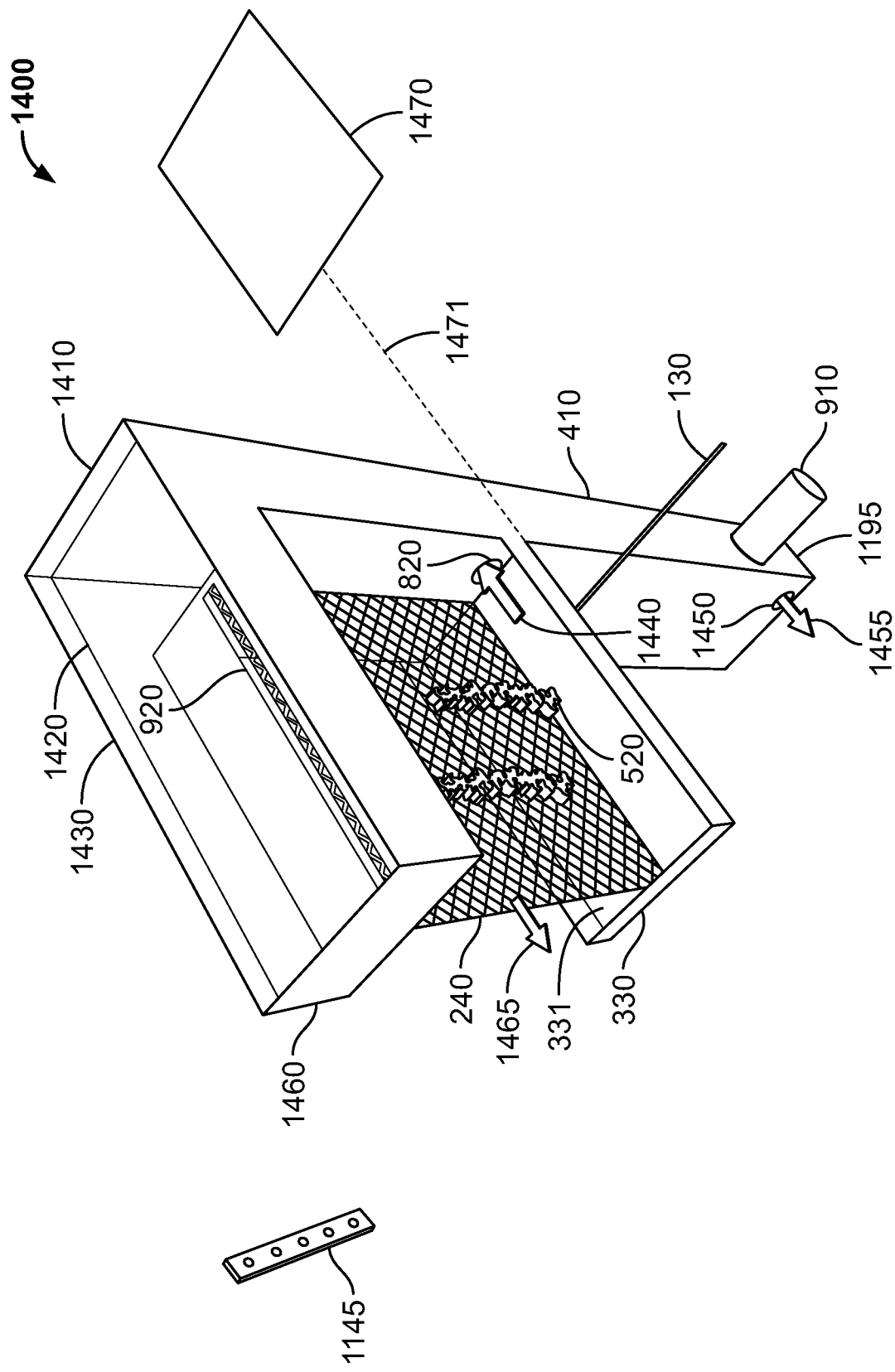
FIG. 14 shows a perspective view of a pole mount reservoir-fed embodiment of the current invention.

FIG. 14 shows an embodiment 1400 of the current invention which brings together several of the previously described embodiments including a reservoir, pole mount, settlement tray, and adds a drain internal to the pole mount for a very compact apparatus. Pole mount reservoir 410 is here depicted as rectangular with a bottom 1195 which sets on a base (not shown) which can support pole mount reservoir 410 on the floor of a sump (not shown) beneath sump water level 130. Water is pumped into pole mount reservoir 410 through water inlet 910 where the water then turns upwards and progresses towards reservoir top opening 1410, which is also the opening of reservoir compartment 1430 of reservoir structure 1460. The water forms a surface 1420 which is the reservoir compartment 1430 surface level 1420, and the open space between this water surface level 1420 and the top of the reservoir top opening 1410 is the headspace. This open reservoir structure 1460 allows the user to reach into reservoir structure 1460 to access and clean the top of macroalgal attachment material 240 and water outlet 920 (which commonly clogs with algal growth); this cannot be achieved with the closed water pipe of previous art FIG. 2. Reservoir structure 1460 and reservoir compartment 1430 are shown here as being substantially the same, however reservoir compartment 1430 could alternately be smaller than reservoir structure 1460.

Water subsequently exits reservoir compartment 1430 through water outlet 920 and flows down in waterfall fashion over macroalgal attachment material 240 which is secured substantially below water outlet 920. "Substantially below water outlet" is defined herein to mean that more than half of macroalgal attachment surface 241 is on the side of the water outlet that water will flow towards gravity. "Above" is herein defined to mean a position farther from the center of the earth, compared to another position. The flowing water (not shown) and any elongated algal growth 520 enabled by illumination source 1145 go down onto macroalgal settlement surface 331 of macroalgal settlement tray 330; the macroalgal growth substantially stays on tray 330 while the water exits tray 330 through drain orifice 820; this exiting water is represented by arrow 1440. Drain orifice 820 is connected to a drain pipe (not shown) internal to pole mount reservoir 410; this internal drain pipe extends down to drain outlet 1450 where the water then flows back into the sump following arrow 1455. The internal drain pipe keeps the downflowing water separate from the upflowing water inside pole mount reservoir 410 that enters from inlet 910.

In this embodiment 1400, settlement tray 330 is coupled to pole mount reservoir 410, and attachment material 240 is supported by reservoir structure 1460 such that removal of apparatus 1400 from a sump does not alter the positional relationship between attachment material 240 and tray 330. This is important because when attachment material 240 is full of growth 520 which extends down and collects in thick mats on tray 330, having to pull material 240 away from tray 330 causes algal growth 520 to rip apart into at least two portions and often many more pieces which fall into the sump, or clog drain orifice 820, or fall onto the floor of the room where apparatus 1400 is located. By preserving the positional relationship between material 240 and tray 330 when apparatus 1400 is removed for cleaning/harvesting, no broken algal strands travel to the sump or the floor. If desired of course, the user could alternately reach down into reservoir top opening 1410 and pull attachment material 240 upwards if algal growth is not too thick; this is a fast and easy cleaning option although some growth 520 may be scraped off. The water source flowing into water inlet 910 could be turned off before such a cleaning operation. And another option that preserves the positional relationship between material 240 and tray 330 is to attach material 240 to tray surface 331 (or to a separate tray that sets on surface 331 as in FIG. 13A) and enable material 240 to slide out laterally in the direction of arrow 1465. As material 240 slides out of water outlet 920 in this manner, any growth piled up at the bottom of material 240 will be preserved in one piece because tray 330 (or separate tray on top of tray 330) will slide out with material 240. Water outlet 920 will then be open for cleaning.

Reservoir top opening 1410 does not have a lid shown, however a lid may be used which generally would not be air tight; this enables a headspace to develop between opening 1410 and compartment water level 1420. An open reservoir compartment 1430 such as this allows the user to reach into compartment 1430 to clean reservoir water outlet 920, which in this embodiment is a slot with a rigid screen 240 inserted through it. A simple brushing of the top of outlet 920 is usually sufficient to dislodge any macroalgae which has grown up into outlet 920. This is contrasted with the previous art FIG. 2 where lid 290 must be removed, pump 210 turned off, water delivery pipe 230 lifted out, attachment rings 235 cut off, and finally screen 240 removed; then pipe 230 and screen 240 can be removed to be cleaned, and then the parts re-assembled using new attachment rings 235. If brushing the macroalgae off of the orifice slot in previous art FIG. 2 is attempted without disassembly, the algae get pushed further up into pipe 230, often making the blockage worse.

Macroalgal settlement surface 331 defines a plane that is represented by rectangle 1470 which is shown at the same elevation as surface 331 by dotted line 1471. As described in FIG. 5, one of the defining factors of a pole-mount embodiment of the current invention is that water can be supplied to the apparatus from below the apparatus through pole mount reservoir 410, instead of from above the apparatus as in previous art. So by requiring that water delivery structure 410 intersect the plane of settlement surface 331, water can then come from below surface 331 instead of from above it. Furthering this concept is requiring that the water source structure, such as pole mount reservoir 410, actually contact macroalgal settlement structure 330 such as it does in FIG. 14. Such contact might be a simple weighted tray 330 that sits on a ledge of pole mount reservoir 410, or a releasable mechanism that allows easy detachment of tray 330 from pole mount reservoir 410 such that tray 330 might slide out laterally (for example, in direction of arrow 1465), or tray 330 might be permanently coupled to pole mount reservoir 410 as shown, possibly by being made of the same material as pole mount reservoir 410. Any other attachment mechanism in the art may also be used. And although shown that pole mount 410 transitions to reservoir structure 1460 at the point of intersection with tray 330, the transition could instead be above or below the point of intersection.

Figure 17:
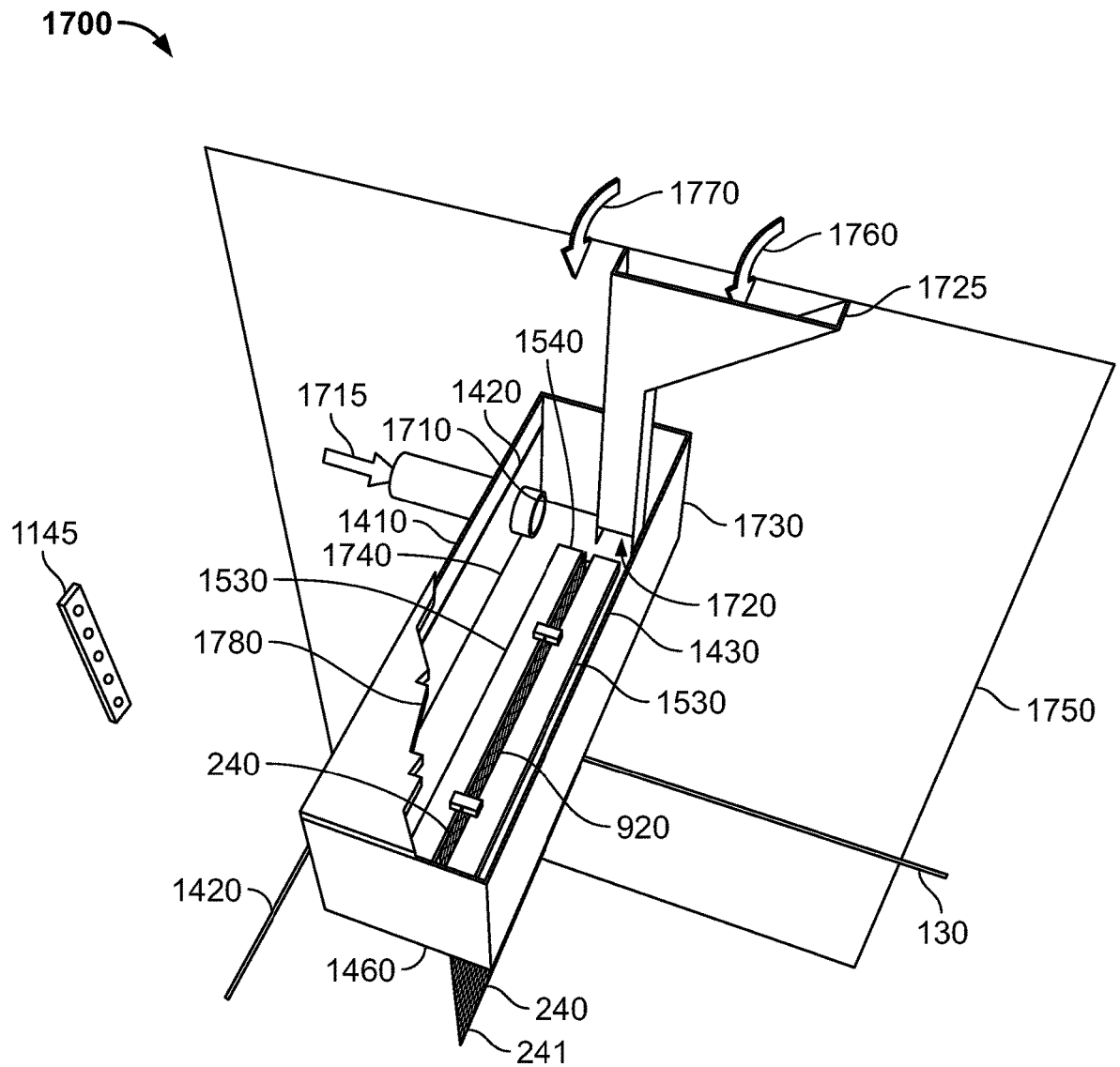
FIG. 17 shows a perspective view of a reservoir embodiment, attached to and supplied water by a sump wall overflow.

FIG. 17 shows an embodiment of the current invention that makes use of reservoir embodiments and screen removal embodiments described above. 1700 is a waterfall algae scrubber that is positioned adjacent to wall 1750 of a sump (not shown but similar to sump 110 of FIG. 1) with the addition of sump wall 1750 (also called a partition) in the middle of the sump such that water can overflow the top of sump wall 1750 from one section of the sump to another section as shown by arrows 1760 and 1770. And if using sump wall 1750 as a support for algae scrubber 1700, no other support needs to be added, including no pole mount, and no shelf. Sump walls or partitions such as 1750 are already included in many types of sumps. Operation is as follows:

Reservoir structure 1460 is positioned adjacent to sump wall 1750 by a mechanism not shown, but the mechanism could be glue, or a hanger or a hook over the top of wall 1750, or a support which sits on the bottom of the sump below sump water level 130, or any other mechanism in the art; the operational water level inside reservoir compartment 1430 is represented by line 1420. Water (not shown) enters compartment 1430 through water inlet 1710; water flowing through inlet 1710 is represented by arrow 1715. Inlet 1710 is on sidewall 1730 of compartment 1430, however inlet 1710 might be on a floor 1740 of compartment 1430. If on a sidewall 1730, inlet 1710 might be above the compartment water level 1420, or might be below water level 1420 as shown. Alternately, water might enter compartment 1430 by overflowing wall 1750 via arrow 1770 and subsequently falling down into compartment 1430 through reservoir top opening 1410, or overflowing via arrow 1760 and subsequently traveling through an overflow capture 1725 which leads to reservoir compartment water inlet 1720. Similar to inlet 1710, the placement of inlet 1720 can be on a sidewall 1730 as shown, and might be below the compartment water level 1420 as shown or above water level 1420. Overflow capture 1725 has an advantage of aggregating overflowing water 1760 from a larger area than compartment 1430 would by itself. Reservoir compartment 1430 is shown in this embodiment as being substantially the same structure as reservoir structure 1460, however reservoir compartment 1430 could be a smaller portion of reservoir structure 1460 such that more of reservoir structure 1460 were used for support or other needs instead of the containment of water.

Once inside reservoir compartment 1430, water then travels down through water outlet 920 which in FIG. 17 is defined by water outlet structure 1530 and floor 1740. As in FIG. 15A, water outlet structure 1530 defines the shape of water outlet 920, and structure 1530 can be positioned on a floor 1740 of compartment 1430 by any suitable type of positioning means (not shown). Although water outlet structure 1530 in FIG. 15A defined one panel 1530, in FIG. 17 structure 1530 defines two panels, each panel 1530 defining a side portion of water outlet 920. This concept of water outlet structure 1530 being comprised of panels 1530, all of which contribute to defining water outlet 920, can be extended to any number of water outlet structure 1530 panels, each defining a portion of water outlet 920. Water outlet structure 1530 positioning means 1540, which in FIGS. 15A and 15B is a hinge, is instead a groove (not shown) in floor 1740 below panels 1530. This positioning means 1540 allows panels 1530 to simply set on floor 1740 and attachment material 240 can then be lowered through water outlet 920. For removal, attachment material 240 is simply lifted upwards; prior removal of panels 1530 can be performed but is not required because they will be pushed upwards and sideways by the upwards movement of material 240. It is for this reason that panels 1530 are not permanently attached to floor 1740 in this embodiment.

Once water (not shown) has exited water outlet 920, the water then flows down macroalgal attachment surface 241 and is illuminated by an illumination source such as LED 1145 such that macroalgae (not shown) attaches to and grows on surface 241. The water then continues downwards until it reaches the ambient water surface level below which is represented as line 130; if water level 130 is below the bottom of attachment material 240 then the water simply falls off material 240. Lid 1780, shown as a cutaway view, may be used to cover compartment 1430. Compartment 1430 might be an upper section of reservoir structure 1460 as shown, which simplifies the use of lid 1780 because reservoir top opening 1410 is approximately the same size and shape as the upper portion of reservoir compartment 1430. Lid 1780 generally will have a headspace below it, above compartment water level 1420, such that water level 1420 is enabled to vary in height above outlet 920. This non-sealed nature of lid 1780 allows it to be removed by the user for observation of water outlet 920 without altering the flow of water through outlet 920, and this type of in-service observation of the top of outlet 920 is not possible with a sealed water pipe.

In order to obtain uniform flow of water in the reservoir compartment and thus through outlet 920, a taller compartment 1430 can be utilized so that compartment water level 1420 can be increased; this will keep uneven flow (waves) at water surface level 1420 farther away from water outlet 920 and will allow a more uniform flow out of water outlet 920 to provide attachment surface 241 with more uniform water coverage, instead of some areas with high flow and other areas with low flow as often happens with previous art water pipes where water shoot towards the end of the pipe slot. A problem with these previous art water pipes (as in FIG. 2), especially when there was not yet any growth on the screen, was that the water pressure inside the pipe forced most of the water to the end of the pipe, and thus most of the water flowed out only at the end of the slot; the other end of the slot received little or no flow; the present embodiment of FIG. 17 allows the water movement to slow down and stabilize before exiting outlet 920. A reservoir compartment water surface level 1420 of at least 3 cm will suffice for small algae scrubbers 1700 with slow water flow, however larger algae scrubbers with more flow might need at least 4, 5, 6, 7, 8, 9, 10, 12 or 15 cm, and even larger algae scrubbers might need at least 20 cm.

Another way of obtaining uniform water outlet 920 flow is to have a large volume of water in reservoir compartment 1430 relative to the size of outlet 920. The area size of outlet 920 in FIG. 17 is defined on the long sides by water outlet structures 1530 and on the short sides by the cutout in floor 1740 of reservoir compartment 1430, thus forming a rectangle. For example, the long sides are typically the same length as attachment material 240, in this example possibly 15 cm, and the short sides are typically 0.3 cm, for a cross sectional area of 4.5 square cm. And because reservoir compartment 1430 is essentially the same dimensions as reservoir structure 1460 in FIG. 17, specifying a large size for reservoir top opening 1410 essentially specifies a large amount of water above outlet 920 which will be more uniform during larger flows into compartment 1430 and with less variation of flow from one section of outlet 920 to another. A ratio of reservoir top opening 1410 area to water outlet 920 area of at least 15 has shown to be a good minimum, however larger algae scrubbers 1700 with more water flow, especially when the user must reach through top opening 1410 to access material 240, might need ratios of 30, 50, or 100.

Yet another way to define reservoir structure 1460 dimensions in order to provide uniform water flow out of outlet 920 is to state how long water should continue to flow uninterrupted out of outlet 920 once water is turned off from the water inlet 1710 or 1720. The longer time that water can sustain flow out of outlet 920 without being replenished by water from a water inlet, the more water is being held in reservoir compartment 1430 relative to the size of outlet 920. Uninterrupted flow is defined to be water continuing to flow out of all parts of outlet 920 in one continuous horizontal stream without breaking into segments of smaller horizontal streams and without air passing through outlet 920. A time of 2 seconds has shown to be sufficient for smaller algae scrubbers 1700, although larger algae scrubbers with more flow might need 3, 5, 10, 20, 30, 40, 50 or 60 seconds of uninterrupted water flow out of outlet 920 after water input is stopped.

Figures 18A, 18B:
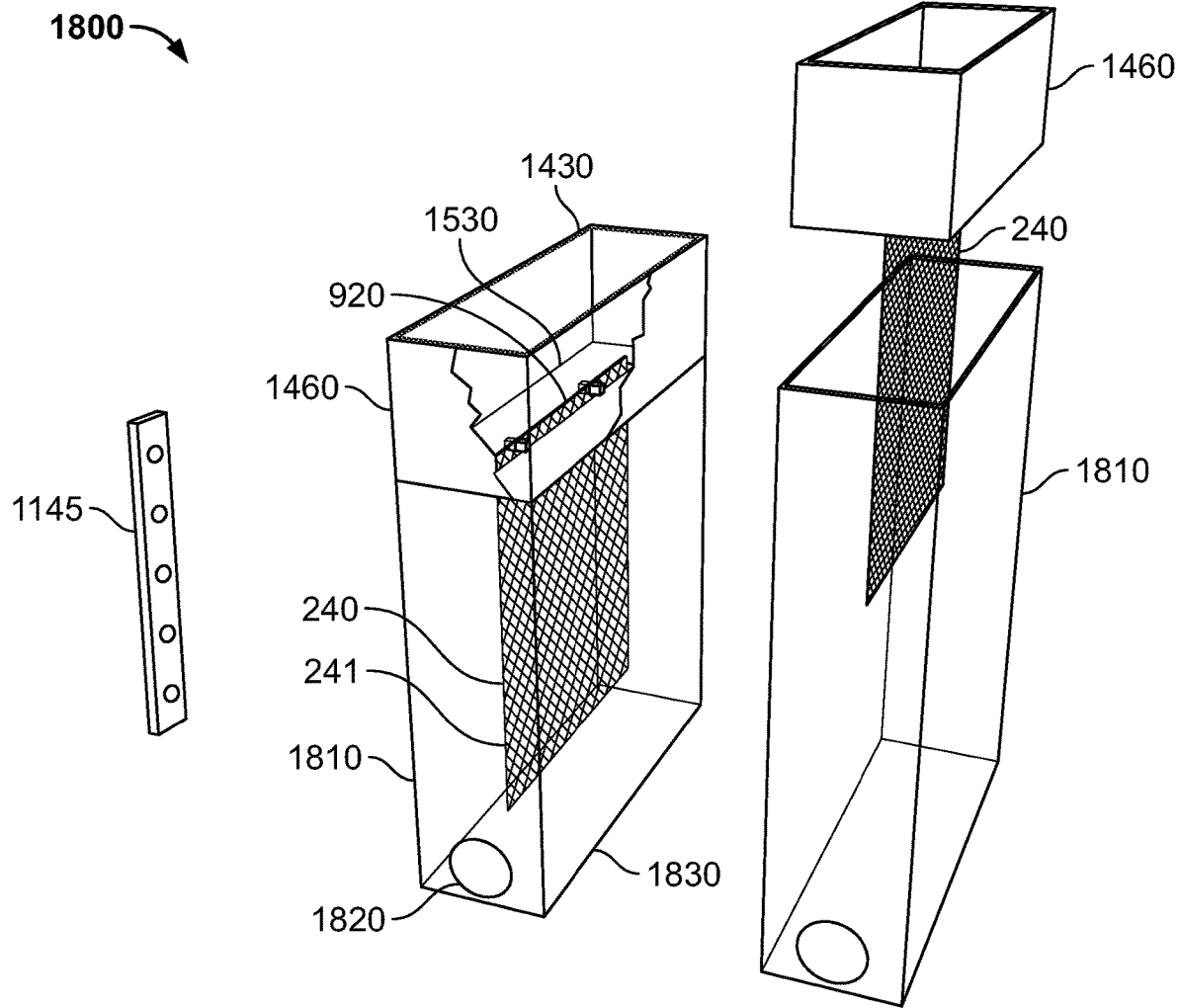
FIG. 18A shows a perspective view of a reservoir embodiment, self supported on a transparent growth container.
FIG. 18B shows a perspective view of the reservoir embodiment of FIG. 18A, lifted out of the transparent growth container.

FIG. 18A shows an embodiment where the screen removal and cleaning process of a reservoir is simplified even further. In FIG. 17, after water outlet structure 1530 has been lifted and material 240 removed, the user may want to access underneath reservoir structure 1460 in order to clean algal growth which may have attached there in the sump, but accessing this area may require reaching between many things in a sump, or lifting the entire apparatus 1700 out. FIG. 18A however combines reservoir compartment 1430 and water outlet structure 1530 into a single unified component which in this embodiment is also the entire reservoir structure 1460 such that lifting reservoir 1460 up allows the user access to both the top and bottom of water outlet 920. Thus material 240 might not need to be removed at all from compartment 1430 because the top and bottom of outlet 920 can be accessed and cleaned without doing so. The water inlet of reservoir structure 1460 might be any of the same inlets of FIG. 17 and thus are not shown here. Water and algal growth (not shown) fall onto floor 1830, and growth on attachment surface 241 can be scraped down onto floor 1830 also; water exits transparent containment wall 1810 through drain hole 1820.

FIG. 18B shows reservoir structure 1460 lifted out of transparent containment wall 1810 so that the algal growth collected on floor 1830 can be removed; containment wall 1810 and floor 1830 serve as a box to carry the growth. Compared to FIG. 17, a main difference of FIGS. 18A and 18B is the support structure 1810 which is shown as a simple transparent container 1810 that can also function as a macroalgal growth containment wall 1810. Reservoir structure 1460 abuts and fits onto containment wall 1810 and is held in place by a friction fit, but might instead be held by a lip at the top of structure 1460 or by other common attachment or positioning techniques. Containment wall 1810 might only be one side of structure 1460 such as a single planar supporting wall, or containment wall 1810 might encircle more or all of structure 1460 as it does in FIGS. 18A and 18B. Instead of acting as a support, containment wall 1810 might instead simply hang from reservoir structure 1460, for example if structure 1460 were supported by some other means. In this case containment wall 1810 might not have floor 1830, and water flowing down macroalgal attachment surface 241 would simply fall off of the bottom of surface 241. And because containment wall 1810 can be transparent or translucent, or opaque with illumination ports, illumination from illumination source 1145 reaches attachment surface 241 and enables algal growth to occur. Illumination source 1145 might alternately be inside of containment wall 1830, possibly mounted onto an internal surface of containment wall 1830 thus allowing containment wall 1830 to be opaque to substantially contain illumination.

Because attachment material 240 can remain coupled to water outlet structure 1530 when the top and bottom of water outlet 920 are accessed for cleaning, a cost saving manufacturing embodiment might be to combine water outlet structure 1530, reservoir structure 1460, and attachment material 240 into a single unified component. FIG. 18B shows that when water outlet structure 1530, reservoir structure 1460, and attachment material 240 are lifted out of containment wall 1810 they can essentially be one molded part that gives full access to the top and bottom of water outlet 920 (not visible in FIG. 18B) and yet still provide the flow stabilizing benefits of a reservoir 1460. A last option for simplicity might be if the entire structure of FIG. 18A were a single unified component. With the possible exception of floor 1830, a single transparent or translucent structure could perform the functions of reservoir structure 1460, reservoir compartment 1430, water outlet structure 1530, macroalgal attachment material 240, and growth containment wall 1810. If the upper portion of the structure could be made or painted opaque, possibly black, then the water outlet could be shielded from illumination source 1145 while the attachment material 240 could still receive illumination. And if the illumination source were internal to growth containment wall 1810, then the entire unified structure could be opaque.

Example Claims—Reservoir Slots

1. An apparatus for supporting macroalgal attachment material and supplying water to a macroalgal attachment surface, comprising:
   a macroalgal attachment material defining a macroalgal attachment surface;
   a reservoir structure defining a reservoir compartment, a reservoir top opening, and a water outlet on a floor of the reservoir compartment;
   a macroalgal attachment material positioning mechanism, the macroalgal attachment material positioning mechanism to position the macroalgal attachment material substantially below the water outlet and to align the macroalgal attachment surface such that water flowing out of the water outlet contacts the macroalgal attachment surface.
2. The apparatus for supporting macroalgal attachment material of Claim 1, further comprising a water inlet to the reservoir compartment.
3. The apparatus for supporting macroalgal attachment material of Claim 2, wherein the water inlet is located on a side wall of the reservoir compartment.
4. The apparatus for supporting macroalgal attachment material of Claim 2, wherein the water inlet is located below the reservoir compartment water surface level.
5. The apparatus for supporting macroalgal attachment material of Claim 2, wherein the water inlet is located on a floor of the reservoir compartment.
6. The apparatus for supporting macroalgal attachment material of Claim 2, wherein the water inlet is located above a water surface level of the reservoir compartment.
7. The apparatus for supporting macroalgal attachment material of Claim 2, wherein the water inlet is the reservoir top opening.
8. The apparatus for supporting macroalgal attachment material of Claim 6, wherein water falls down into the reservoir top opening.
9. The apparatus for supporting macroalgal attachment material of Claim 8, wherein the water is overflowed from a wall.
10. The apparatus for supporting macroalgal attachment material of Claim 9, wherein the reservoir structure is coupled to the wall.
11. The apparatus for supporting macroalgal attachment material of Claim 2, wherein the water inlet (1720) passes through the reservoir top opening.
12. The apparatus for supporting macroalgal attachment material of Claim 11, wherein the water inlet (1720) extends substantially to a floor of the reservoir compartment.
13. The apparatus for supporting macroalgal attachment material of Claim 1, further comprising:
    a water outlet structure;
    a water outlet structure positioning means, the water outlet structure positioning means to position the water outlet structure such that the water outlet structure defines a portion of the water outlet.
14. The apparatus for supporting macroalgal attachment material of Claim 13, wherein the water outlet structure is releasably coupled to the macroalgal attachment material.
15. The apparatus for supporting macroalgal attachment material of Claim 13, wherein the water outlet structure and the macroalgal attachment material are a single unified component.
16. The apparatus for supporting macroalgal attachment material of Claim 13, wherein the water outlet structure is moveable from a first position for operation to a second position for removal of the macroalgal attachment material.
17. The apparatus for supporting macroalgal attachment material of Claim 16, wherein the second position is above the first position.
18. The apparatus for supporting macroalgal attachment material of Claim 13, wherein the water outlet structure defines at least one panel.
19. The apparatus for supporting macroalgal attachment material of Claim 13, wherein water outlet structure positioning means defines a hinge.
20. The apparatus for supporting macroalgal attachment material of Claim 1, further comprising a macroalgal growth containment wall, the macroalgal growth containment wall configured to abut the reservoir structure.

21. The apparatus for supporting macroalgal attachment material of Claim 20, wherein the containment wall includes an illumination source.
22. The apparatus for supporting macroalgal attachment material of Claim 20, wherein the containment wall supports the reservoir structure.
23. The apparatus for supporting macroalgal attachment material of Claim 20, wherein the containment wall is releasably coupled to the reservoir structure.
24. The apparatus for supporting macroalgal attachment material of Claim 20, wherein the containment wall substantially surrounds the macroalgal attachment material.
25. The apparatus for supporting macroalgal attachment material of Claim 20, wherein the reservoir compartment, water outlet structure, and macroalgal attachment material are a single unified component.
26. The apparatus for supporting macroalgal attachment material of Claims 13 and 20, wherein the reservoir compartment, water outlet structure, macroalgal attachment material, and macroalgal growth containment wall are a single unified component.
27. The apparatus for supporting macroalgal attachment material of Claim 1, wherein a reservoir compartment water surface level height is at least 3 cm above the water outlet.
28. The apparatus for supporting macroalgal attachment material of Claim 1, wherein a ratio of a reservoir top opening area to a water outlet area is at least 15.
29. The apparatus for supporting macroalgal attachment material of Claim 1, wherein the reservoir compartment holds enough water to sustain water flow out of the water outlet for at least 3 seconds when no water enters the reservoir compartment.
30. The apparatus for supporting macroalgal attachment material of Claim 1, wherein the macroalgal attachment material is 2-sided.
31. An apparatus for supporting macroalgal attachment material and supplying water to a macroalgal attachment surface substantially as hereinbefore described with reference to FIGS. 14 and 17-18.

Illumination Devices

An embodiment of the present invention describes a low cost and easy to manufacture illumination apparatus which has no metallic components in contact with water, and further describes a method for encapsulating illumination emitters by utilizing essentially a single step. Reducing the encapsulation process of illumination devices to essentially a single step allows the cost of the final product to be low enough for small aquarium owners, and by being completely encapsulated with no metallic components in contact with water, the method and apparatus provide the highest corrosion protection for the illumination emitter as well as the highest safety for aquarium livestock. Applicant's GEM™ lights are examples of such devices. Following are definitions specific to the present methods and apparatuses for illumination devices:

Illumination Emitter: A source of illumination that has electrical input such as wires, and also produces heat, and also must be protected from water and moisture. Illumination Emitters are commonly light emitting diodes (LED) but could be other electrical devices.

Overmold: Thermally conductive and electrically insulative encapsulation thermoplastic or thermoset resin that is placed or poured into a mold cavity around an illumination emitter, lens, and electrical power cable. When solidified, the overmold becomes the outer casing of the illumination apparatus, and although it can be placed or poured in more than one step by allowing a previously placed or poured resin to substantially solidify first, it is preferred to have a single placement or pouring to reduce labor and time costs. Overmold and overmolding are the actions of making an overmold.

Lens: A substantially optically transparent or translucent material that covers and protects an illumination emitter. The lens may be comprised of several different layers including an innermost layer in contact with the emitter itself, and an outermost layer in contact with ambient air or water, and the lens may also be buoyant or have a buoyant attachment to assist with encapsulation positioning.

Ambient: Surrounding air or water where the illumination apparatus is to be operated. The air is commonly the air in an enclosed cabinet and generally can be as high as 38 C, and the water is commonly the water in an aquarium or sump and can be as high as 32 C or a seaweed cultivator which can be as high as 45 C. Heat from the illumination emitter is transferred to the ambient.

Pre-Mold Structure: A non-metallic substantially rigid component which includes the illumination emitter and lens, and optionally any braces or floats or other components necessary for positioning the illumination emitter in a mold cavity prior to placement or pouring of the overmold.

Mold Cavity: The concave portion of a mold that is filled with overmold encapsulation thermoplastic or thermoset resin.

Brace: A substantially rigid component internal to a mold cavity which holds a pre-mold structure in position until the overmold can be placed or poured and subsequently solidified; the brace may be part of the pre-mold structure or a separate component. The brace becomes embedded within and thus part of the resulting solidified overmold.

Fill Level: The uppermost surface level of liquid resin after it is poured into a mold cavity. The fill level cannot be above the top of a mold cavity; above the fill level is ambient air.

Outer Perimeter: The outermost locations of a mold cavity that overmold material will flow into and solidify, up to and including the fill level.

Holding Force: A force which holds the pre-mold structure in position until the overmold is solidified. The holding force may come from a holding device, van der Waals forces, magnets, or other sources.

Holding Device: A device external to the pre-mold structure and resultant overmold, which holds the lens and thus the pre-mold structure in position until the overmold material is placed and solidified. The holding device may attach to a lens temporarily by suction, adhesive, van der Waals forces, or any combination of these.

Lens-Mold Interface: A location in a mold cavity where a lens is positioned in contact with a wall of the cavity. A lens may be held in position at a lens-mold interface by an external force, or may be adhered to the lens-mold interface with a temporary adhesion technique such as van der Waals force or a removable or dissolvable adhesive.

Lens Outer Surface: A surface of the lens, which after molding of the illumination emitter is completed, is exposed to ambient and thus allows illumination to travel from the illumination emitter to the ambient.

Substantially Not Covered By Resin: A state of cleanliness after molding, wherein a lens outer surface does not require a substantial machining step to remove residual thermoplastic or thermoset resin; any residual plastic or resin can be easily removed by hand wiping.

No Heat or Moisture Damage: Ability of an illumination emitter to operate continuously for at least six months without failing due to heat or moisture.

Bond Line: Area on an outer perimeter of a resultant overmold that is in contact with ambient air or ambient water, where the overmold thermoplastic or thermoset resin is in contact with another material. The other material may be a lens, brace, electrical power cable, or another portion of thermoplastic or resin which had previously solidified. Bond lines should be minimized in order to reduce pathways for moisture to enter, and can be expressed as a bond line ratio defined further below. A bond line should not be confused with a mold line, which is the result of separation of a two-part mold of a single pouring of liquid resin.

Substantially Non-Metallic: Will not corrode in long term usage in freshwater or saltwater.

Substantially Electrically Non-Conductive: Electrical resistance of at least 10 ohm-cm.

Substantially Thermally Conductive: Thermal conductivity of at least 0.5 w/mk.

Substantially Encapsulated: An illumination emitter surrounded and contained on all surfaces except for its lens, electrical power cable, and any braces.

The difficulty of encapsulating an illumination emitter in a low cost manner is the number of manufacturing steps needed, especially the number of steps of overmolding because these steps require the handling of liquid plastic that must be allowed to solidify, and if a thermoset resin is used it must sit undisturbed for hours at a time in order to cure. The seemingly simple process of mixing and pouring a base layer of resin, allowing it to cure, then placing illumination emitters and lenses on it and subsequently mixing and pouring more resin over it and allowing it to also cure, is at least twice the number of overmolding steps as a single pouring. This can greatly increase the cost of the final product due to high labor costs of overmolding which are sometimes the highest cost of the product. A second difficulty is water ingress, because a two-step overmolding process leaves a bond line all the way, or substantially all the way, around the overmold thus increasing the potential pathways for moisture to enter.

In particular, trying to encapsulate an illumination emitter with a single step of mixing and pouring thermoset resin proves difficult because there is nothing to hold the emitter in position (no bottom supporting layer of cured resin) while allowing the newly poured resin to solidify. If not held in place the emitter will sink to the bottom of the mold cavity and will be exposed to ambient air or water when removed from the mold. If a pedestal or pins are used to position the emitter during curing, they will become part of the overmold and will add additional bond lines and thus potential water pathways, not to mention that if a pedestal is not heat conductive itself then it will partially block heat removal from the emitter. Multi-part molds, for example with two halves which are split apart after curing, do not help because the emitter must still be held in position during the curing so that the emitter does not touch any of the outer perimeters. The present invention proposes to hold the emitter in position via the lens. While being a delicate part of an illumination apparatus, it might seem that the lens would not be a good place to manipulate the emitter, yet it turns out that because of the large size and relatively flat lenses needed for macroalgal photosynthetic growth usage (very wide optical dispersion), the lens has enough surface area to allow it to support a high power emitter via only non-permanent manipulating forces. Since these forces simply let go during demolding, they do not require an additional disassembly machining step, and further do not leave anything remaining inside the overmold material itself.

The basis of the illumination apparatus functionality of the present invention is the cured overmold. The material which makes up the overmold may be a thermoplastic such as ABS or PET, or a thermoset resin such as epoxy or polyurethane. The plastic will generally need a thermally conductive filler to be added such as boron nitride or aluminum oxide (alumina). The bright white color of these two fillers in particular adds to the optical reflectivity of the overmold, especially if the overmold is shaped into a dish for illumination reflection; however the true usefulness of these fillers is their ability to conduct heat without conducting electricity. Thermal conductivity of the cured plastic should generally be greater than 0.5 w/mk (watts per meter-kelvin), and preferably greater than 1.0 w/mk, and more preferably greater than 1.5 w/mk, and most preferably greater than 2.0 w/mk, and electrical insulation of the cured resin should generally be greater than $1 \times 10^{12}$ ohm-cm. A higher thermal conductivity will allow a smaller overmold to be used, thus reducing size and cost. So instead of having several sections of the illumination apparatus for different functions (thermal, electrical, casing), a single overmold material performs all the functions. This is what allows for a low cost consumer product.

A desire of the present invention is to reduce the cost of the final consumer product further by reducing the overmolding steps to just one. While there are many steps to manufacturing an illumination apparatus (such as soldering, etc), the application of an overmold is time consuming, and the application of a thermoset resin in particular requires long curing times and can pose the largest cost in time and labor. Automated injection molding and other methods can be used but they don't overcome the need to hold the emitter in place during overmolding. A feature of the present method invention is easily-detachable pre-mold lens positioning, whereas a feature of the present apparatus invention is an emitter overmold with no bond lines except for the required bond line for the lens and possibly the electrical power cable. This is accomplished by positioning the emitter by using a force on the lens itself.

Figure 19:
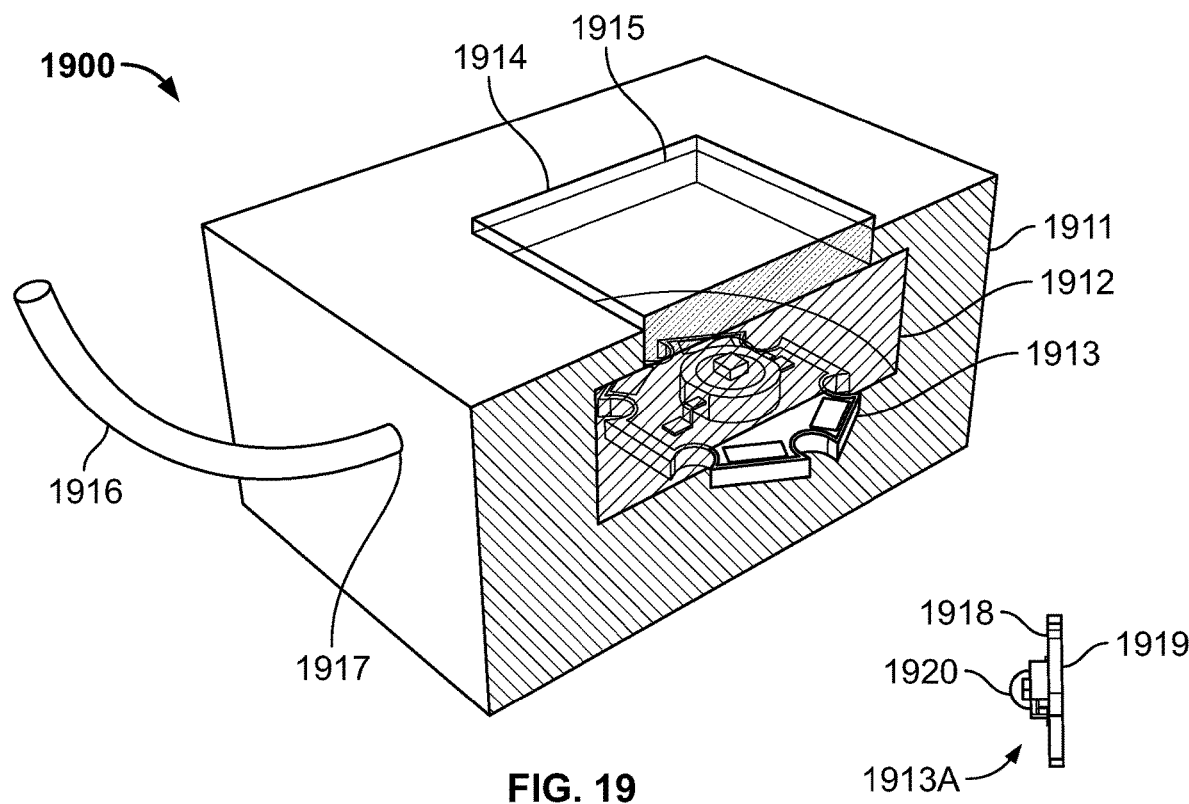
FIG. 19 shows a perspective sectioned view of a submersible illumination emitter embodiment of the current invention.

FIG. 19 shows a perspective partial-cutaway view of an embodiment 1900 of the present apparatus invention, and end result 1900 of the present method invention using overmold 1911. 1900 is a completely sealed illumination apparatus, in this case utilizing a red 660 nanometer color LED 1913 (light emitting diode) for the illumination and photosynthetic growth of macroalgae, however LED 1913 could be any illumination emitting device. Most illumination devices which create their own illumination will use electricity and thus need protection when exposed to water; LED 1913 is therefore sealed to lens 1914 via lens attachment 1912 which might be any commercially available transparent or translucent sealant, encapsulant or potting material, and might be a very thin layer of 0.1 mm or a much thicker layer as shown. By filling the area between LED 1913 and lens 1914 with a sealant such as lens attachment 1912, water ingress is further prevented should moisture enter overmold 1911 from the top near lens 1914. Illumination from LED 1913 travels through lens attachment 1912 and subsequently enters lens 1914, and after traveling through lens 1914 illumination enters the surrounding ambient air or water (not shown). LED 1913, lens attachment 1912, and lens 1914 together comprise a "pre-mold structure" which is assembled before the step of applying overmold 1911.

Lens attachment 1912 and LED 1913 are surrounded and sealed by overmold 1911. Overmold 1911 protects LED 1913 from moisture ingress from ambient water immersion, and also conducts heat away from LED 1913 into the ambient air or water, and further becomes the outer shell or casing for the final apparatus 1900. Overmold 1911 is made of an epoxy resin with aluminum oxide (alumina) powder filler added to the resin before curing, however other thermally conductive and electrically insulating fillers could be added such as boron nitride powder or diamond powder. Aluminum oxide is useful because of it's low cost and generally white color which reflects more light, and boron nitride because of it's very high thermal conductivity, brilliant white color, and low weight. Thermoset resins such as epoxy and polyurethanes generally are very water resistant, and epoxy can be very heat resistant also. These resins by themselves (without filler) however, are low in thermal conductivity (generally about 0.12 w/mk) and are generally translucent; thus the addition of filler converts these resins into thermally conductive, electrically resistive, rigid white structures. Injection molding of overmold 1911 using thermoplastics is also possible, however further description below will focus on thermoset resins which are poured while in a liquid state and which solidify (cure) thereafter.

Preventing water and moisture ingress to LED 1913 is of primary importance, and thus the structure of overmold 1911 is as important as the material itself. Any seam, crack, fissure or other non-sealing part of the structure of overmold 1911 might enable moisture from the ambient to reach LED 1913, and thus the minimization of assembly steps or components which introduce possible seams, cracks, or fissures is best. If overmold 1911 material itself is assumed to be essentially a moisture barrier, then the possible points of entry for moisture will be bond lines 1915 and 1917. A bond line is where two materials are mated together in a permanent fashion, and in the example of submersible overmold 1911 the bond lines should be completely waterproof, including the prevention of slow moisture creep that may occur with temperature fluctuations over several months. Bond line 1917 is relatively small, located where electrical power cable 1916 enters overmold 1911; it is usually only a few millimeters in circumference. Bond line 1915 however has a length which is much longer, traveling all the way around lens 1914 where lens 1914 is adhered to overmold 1911. Bond line 1915 also has a depth defined as the distance from the top outer surface of overmold 1911 down to lens attachment 1912. As long as these bond lines (1915, 1917) are waterproof, LED 1913 should remain free of moisture ingress. Reducing the length of the bond lines (1915, 1917) will correspondingly reduce the opportunity for seams, cracks, or fissures to be present; reducing the size of lens 1914 will help accomplish this. A problem arises however in how to manufacture apparatus 1900, because LED 1913 is "floating" in overmold 1911 and thus becomes difficult to position properly when overmold 1911 is being poured (as a liquid) and hardened. By "floating" it is meant that there is no bracket to hold LED 1913 while overmold 1911 solidifies because any such bracket would introduce a bond line which might allow moisture ingress.

1913A shows LED 1913 by itself in a side view. 1918 is the top or front of LED 1913, and 1919 is the bottom or back of LED 1913, and 1920 (the domed section) is the area where illumination is emitted. For maximum thermal heat transfer from LED 1913 to overmold 1911, heat should be extracted from both the front 1918 and back 1919 of LED 1913. However because lens-attachment 1912 is generally not heat conductive (transparent materials, except diamond, conduct heat poorly), this would necessitate lens-attachment 1912 being smaller than shown so that overmold 1911 would cover a substantial portion of the front of LED 1913.

Figure 20:
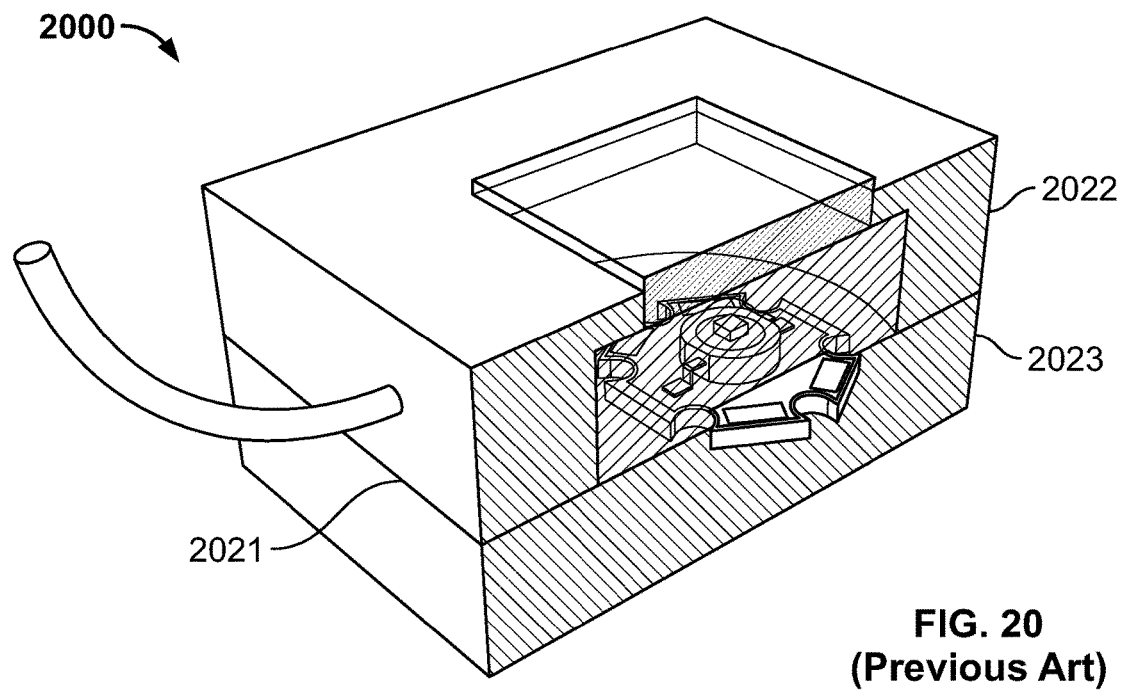
FIG. 20 shows a perspective sectioned view of a previous art submersible illumination emitter.

FIG. 20 show shows a previous art waterproof illumination apparatus 2000 manufactured by a common 2-layer encapsulation technique. In previous art techniques such as this, a first encapsulant layer 2023 was first poured or placed into position. This may have been done by a first pouring of a thermoset resin such as polyurethane or epoxy, or by a first injection molding of a thermoplastic. It may also have been done by simply placing a pre-molded and pre-solidified part 2023 into position. The LED and lens-attachment was then put into position on top of first layer 2023. Second encapsulant layer 2022 was then molded on top of first encapsulant layer 2023; this second encapsulant layer may also have been a poured thermoset resin, and was probably an opaque thermally conductive material. This created a very long bond line 2021 all the way around the illumination structure, and was the largest bond line of the entire illumination structure which allowed for a much greater chance of seams, cracks, or fissures especially if there was any flexing of the overmold during mounting or heating. This was in addition to the fact that it required at least two separate molding steps compared to the single step of the present invention. Thus these previous art techniques not only added to the manufacturing steps and costs but also increased the failure rate. A goal of the present invention is to allow full encapsulation of the illumination emitter in a single step and to so without a bond line between encapsulation layers.

Figure 21:
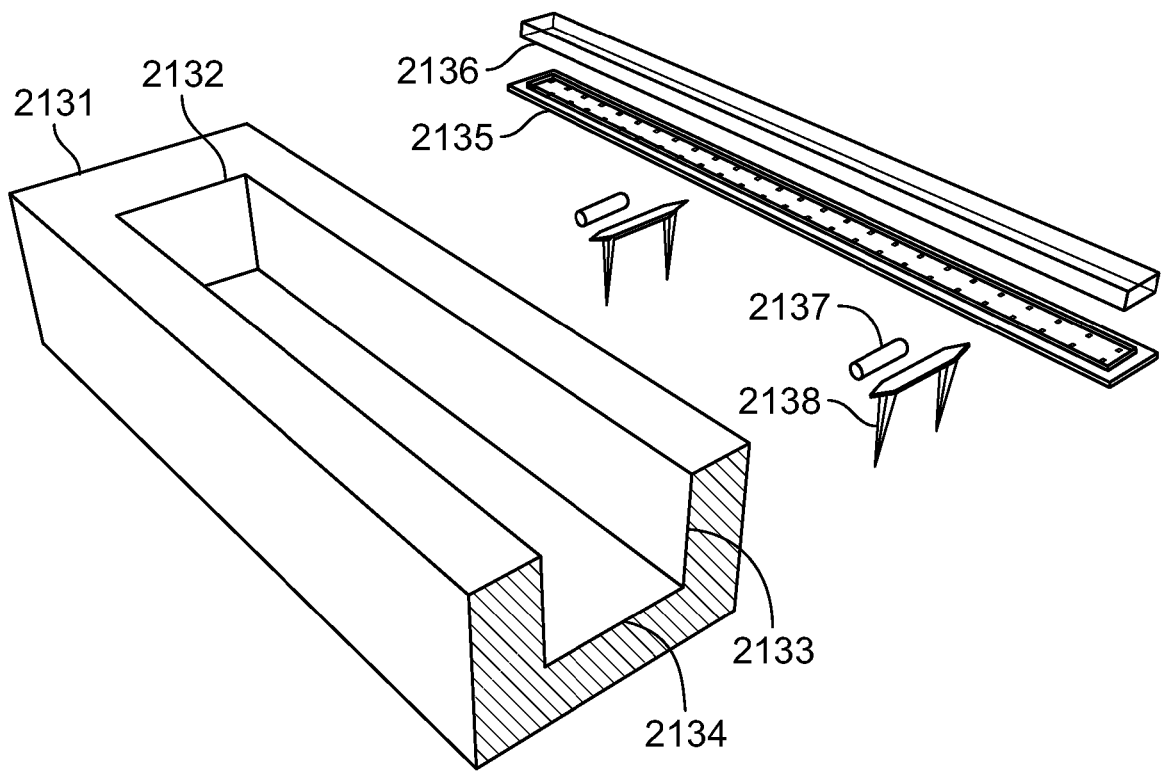
FIG. 21 shows a perspective sectioned view of components of a submersible illumination emitter embodiment before molding.

FIG. 21 shows components of the current invention before the overmolding step. 2131 is a mold for pouring resin into; it is a standard flexible mold made with silicone rubber, but could be any other mold making material. The front of mold 2131 is sectioned off so as to show the inside of mold cavity 2132 more clearly. The top of mold 2131 is the same as the top of the mold cavity 2132 in this embodiment, and becomes the maximum "fill level" outer perimeter which is the maximum height that liquid resin can be filled up to in the cavity 2132. The dimensions of mold cavity 2132 are defined by side walls 2133 and bottom 2134. The illumination emitter in this embodiment is LED 2135 which in this case is a "Chip On Board" (COB) LED strip with aluminum backing (electric cable not shown). Lens 2136 is shaped to compliment the shape of LED 2135 and is a strip of transparent or translucent acrylic; lens 2136 might is attached to LED 2135 via a very thin 0.1 mm layer of transparent silicone or urethane. Since LED 2135 and lens 2136 are long and narrow in this embodiment, it can be helpful if they are somewhat flexible so as to minimize potential cracking if the user flexes it. Float 2137 and brace 2138 are also shown before attachment to lens 2135. Buoyancy floats 2137 might be used if the fill level is more than a centimeter deep, whereas braces 2138 might be used if the fill level is less than a centimeter deep. Taken together and when assembled, LED 2135, lens 2136, floats 2137, and braces 2138 form a pre-mold structure which is then lowered into mold cavity 2132.

Figure 22:
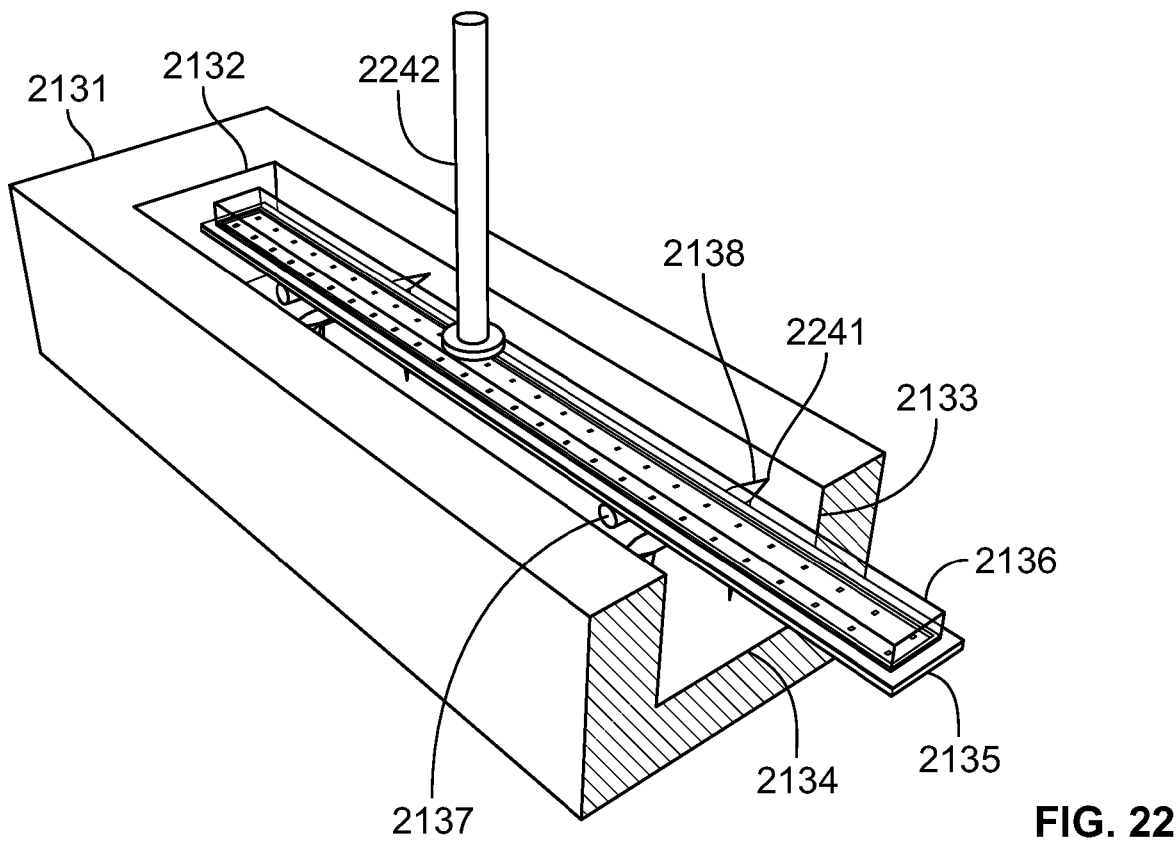
FIG. 22 shows another perspective sectioned view of the components of FIG. 21, of an embodiment of the current invention

FIG. 22 shows the components of FIG. 21 assembled and ready for resin to be poured into mold cavity 2132, but with the addition of optional holding device 2242. The front of mold 2131 is sectioned off so LED 2135 and lens 2136 can be seen in molding position. Optional holding device 2242 is an external substantially rigid device which releasably attaches to the pre-mold structure, primarily by attaching to a portion of lens 2136; the device 2242 does not subsequently become part of the resulting overmold like float 2137 or brace 2138 does; instead holding device 2242 releasably adheres to an outer surface of lens 2136 or other section of the pre-mold structure which does not become covered with resin. Such releasability might be accomplished with water soluble glue such as PVA (polyvinyl acetate, e.g. "Elmer's glue"), or a suction cup, or van der Waals forces which result simply by pressing a soft surface such as vinyl to a rigid lens 2136 surface. The holding of the pre-mold structure by holding device 2242 allows resin to be poured into mold cavity 2132 in a single pour and thus without any bond lines between multiple layers, because there is only one layer. When holding device 2242 is utilized, it probably will not be necessary to utilize floats 2137 or braces 2138. Holding device however 2242 does require attachment and detachment to lens 2136, as well as an external anchor somewhere outside of mold cavity 2132.

If holding device 2242 is not utilized, then the present invention can utilize floats 2137 or braces 2138 or other positioning mechanisms. Braces 2138 are shown extending downwards and sideways; this disposes the pre-mold structure approximately in the center of mold cavity 2132 laterally, and at the top of mold cavity 2132 vertically, such that poured resin fills beneath and to the sides of the pre-mold structure, especially LED 2135 and lens 2136. Braces 2138 will subsequently become part of the cured (solidified) overmold and will contribute bond lines 2241 at outer perimeters where brace 2138 contacts wall 2133 of mold cavity 2132. However these bond lines can be exceeding small due to the pinpoint contact point of brace 2138, and may be as little as 4 mm in circumference, or about 1 square mm in area, thus making it the smallest bond line in the illumination apparatus. The total length of bond lines on the outer surfaces of the overmold should be minimized, and can be expressed as a ratio of total length of bond lines to total surface area of the outer surface of the overmold; this is termed the "bond line ratio".

For example, if mold cavity 2132 is 170 mm long, 30 mm wide, and 20 mm high, once demolded the entire illumination structure would have an approximate external surface area of 18,200 square mm assuming that the height of lens 2136 above the overmold is negligible. Thus a 1 square mm contact point 2241 would have a bond line length (circumference) of 4 mm, and when occupying 8 separate contact points (4 for each brace 2138), would total about 32 mm of bond line. These 8 contact points 2241 would then have a bond line ratio of 32/18200=0.0018 which is a very small value and would offer minimal moisture entrance area compared to the bond line of the lens 2136 itself. However more or larger brace contact points 2241 might be used to provide more support for larger, longer, heavier, or more complex illumination emitters 2135 and lenses 2136, and thus contact points 2241 might have a bond line ratio of 0.002, or 0.01, or 0.1 not including bond lines of lens 2136 or the electrical power cable (not shown). Braces 2138 could alternately extend downward only, which would eliminate the bond lines 2241 on side walls 2133; in this case the weight of the pre-mold structure would push down on braces 2138 causing a friction fit with bottom surface 2134 of mold cavity 2132 which would hold lens 2136 in position as the poured resin cured. If points of entry of moisture are desired to be minimized even further, floats 2137 could be utilized instead of braces 2138; when used without additional positioning structures, floats 2137 become encapsulated entirely and leave no bond lines at all, and require no post-cure holding device removal. Floats 2137 are made of closed cell foam, but could be a sealed canister or balloon. Positioning of the pre-mold structure during pouring and curing could alternately be via magnetism, for example a small magnet (not shown) disposed next to floats 2137; an external magnet or metal bar could then hold the pre-mold structure in position without physically contacting the structure. This small magnet would then become encapsulated with float 2137. Or a small magnet (not shown) could simply be set on top of lens 2136; as long as the magnetism from the external magnet or metal bar were not too strong, the small magnet would stay in position on lens 2136 by friction, and the pre-mold structure would then still be positionable, and the small magnet easily lifted up off of lens 2136 after molding.

Figure 23:
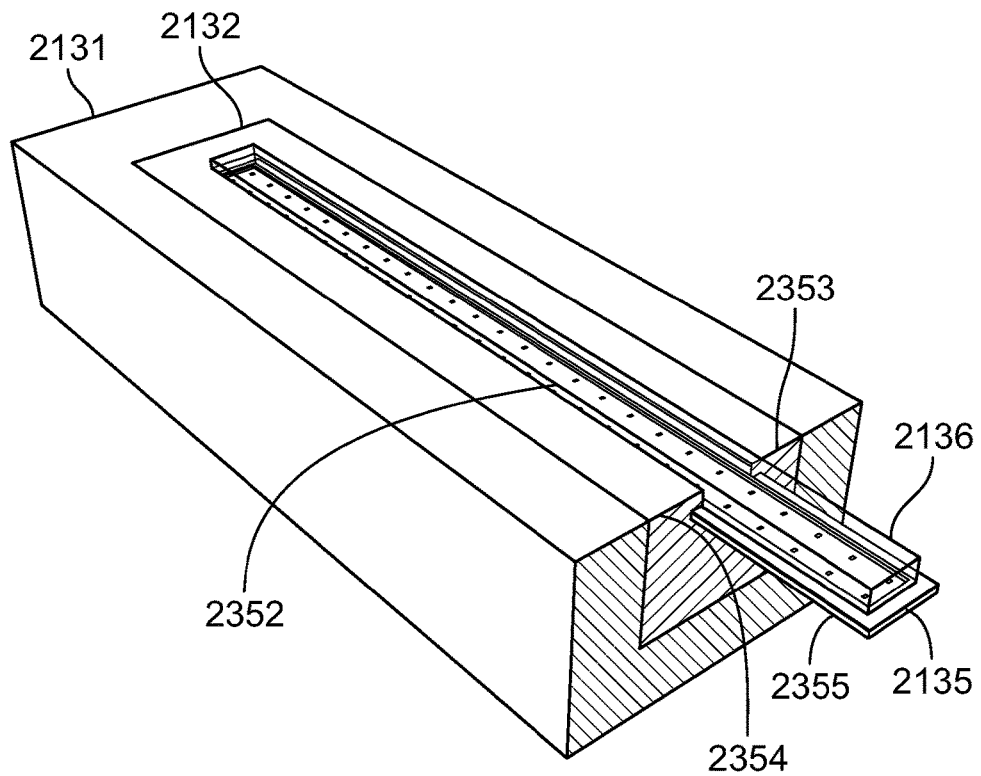
FIG. 23 shows a perspective sectioned view of the resulting molded embodiment using components of FIGS. 21 and 22.

FIG. 23 shows the mold cavity 2132 of FIG. 22 filled with resin 2353; the front of mold 2131 is again sectioned off so LED 2135 and lens 2136 can be seen in position with poured resin 2353 which cures to form overmold 2353. Of particular interest in this figure is fill level 2351 which is defined by the top of mold cavity 2132 and thus becomes an outer perimeter of the upper portion of poured resin overmold 2353. A thicker lens 2136 would protrude farther up out of resin 2353 thus allowing illumination to be refracted differently, however bond line thickness 2354 of lens 2136 would not be affected. In order to increase bond line thickness 2354 (thus increasing water resistance), fill level 2351 would need to be increased (raised upwards), however this would overflow mold cavity 2132 and/or spill onto lens outer surface 2352, thus a taller mold cavity 2132 would be needed. Alternately, instead of a taller mold cavity 2132 the pre-mold structure could be placed into a lower position than shown before pouring resin 2353, by adjusting the positioning of the holding device, braces or floats (all not shown). The top 2355 of LED 2135 is shown in partial contact with overmold 2353. Some LED 2135 devices generate substantial heat on this top 2355 side of LED 2135 and therefore benefit by a larger contact area between top 2355 and poured resin overmold 2353. Obtaining this overlap with overmold 2353 with a single layer/pour of encapsulant resin is not easily done without the lens positioning techniques of the present invention.

Figure 24:
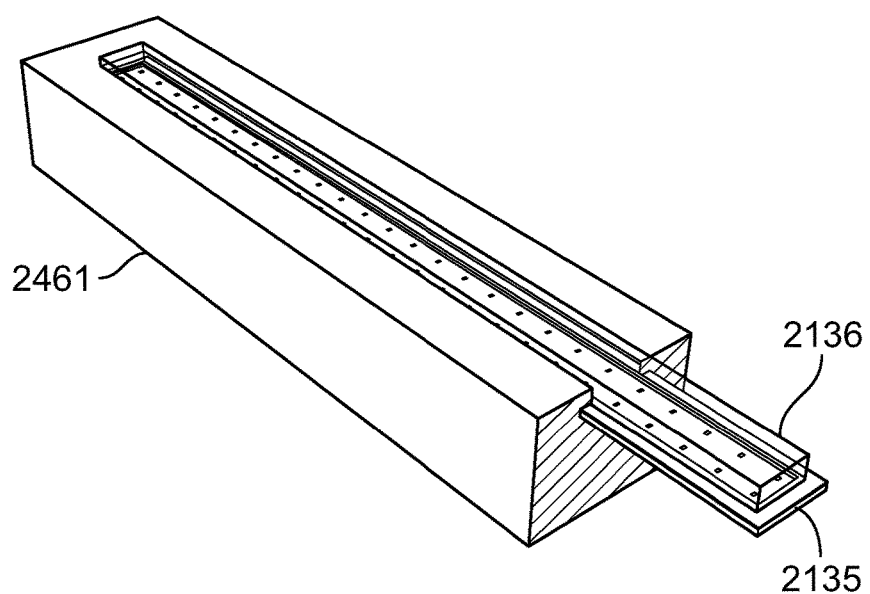
FIG. 24 shows a perspective sectioned view of the resulting demolded embodiment of FIGS. 21, 22 and 23.

FIG. 24 shows a cured and finished illumination apparatus 2400 (electric cable not shown) demolded; the front of cured overmold 2461 is sectioned off so LED 2135 and lens 2136 can be seen. Any internal floats or braces are no longer visible in cured overmold 2461, and any external positioning devices have been removed. Note there are no bond lines at all except for one required for lens 2136; any bond line for an electric cable would be negligible compared to the lens 2136 bond line. It is envisioned that a transparent or translucent layer of resin (not shown) could be applied to the top of the entire overmold 2461 including lens 2136 in order to provide additional protection from moisture ingress through the lens 2136 bond line, however there are no low cost transparent or translucent resins or thermoplastics available which are also thermally conductive more than 0.5 w/mk and therefore this extra sealing layer will provide undesired thermal insulation on the top of overmold 2461 which will need to be accounted for, in addition to requiring an entire extra overmolding step and possibly and extra day of curing. This underscores the importance of the ability to provide the required physical, thermal, electrical, optical and sealing properties in a single overmolding step.

Apparatus 2400 is shown as having been made with long rectangular LED 2135 and long rectangular lens 2136, however it is envisioned that LEDs with smaller and more concentrated illumination output areas be used such as LED 1913 in FIG. 19. The side view 1913A in particular shows that the domed area 1920 where illumination is emitted from would require a much smaller lens 2136 in FIG. 24; this small lens could be a simple transparent or translucent coating applied to dome 1920 before encapsulation. For example common 3 watt power LEDs surface mounted to star shaped printed circuit boards (pcb's) as shown in FIG. 19 typically have a domed or flat illumination emitting area 1920 of about 5 mm in diameter which is only about 16 mm in circumference. The long rectangular LED 2135 and lens 2136 in FIG. 24 in comparison might typically be 6 watts, 150 mm in length, and 10 mm in width, giving a circumference (and bond line) of 320 mm. Thus for the same wattage, two of the round LEDs 1913 would give a total bond line of 32 mm compared to one long rectangular LED 2135 which would have a 320 mm bond line. This 10-to-1 reduction of bond line distance is very significant.

Example: Using mold dimensions as stated in FIG. 22, the resultant overmold would be 170 mm long, 30 mm wide, and 20 mm high, with an approximate external surface area of 18,200 square mm. A typical round shaped electrical power cord might be 3 mm in diameter, with a bond line distance of about 9 mm. Using a single pouring of resin as described herein, the only bond lines would be from the lenses and the power cord; the long rectangular LED 2135 would give a total bond line of 320+9=329, which gives a bond line ratio of 329/18200=0.018 which is nine times higher than for two of the round LEDs 1913 whose total bond line is 32+9=41 and thus whose bond line ratio would be 41/18200=0.002

Adding a second overmold layer adds a 400 mm bond line around the overmold. With a long rectangular lens 2136 the total bond line ratio then becomes 729/18200=0.04 whereas with two round LEDs the total ratio becomes 441/18200=0.024 which again is substantially lower. Adding two braces 2138 of FIG. 21 with pointed tips adds 32 mm of bond line, which increase the total ratio to 0.042 with a long rectangular lens 2136, or 0.003 with two round LEDs. The total bond line ratio including overmold layers, power cables, lenses and braces is preferred to be less than 0.1, and more preferably less than 0.05, and even more preferably less than 0.01, and even more preferably less than 0.005, and most preferably less than 0.001 which can be achieved with a small power cable and a very high output single LED similar in dimensions to LED 1913 but without any braces or second overmold layers. This example size of 18,200 square mm of overmold 2461 could contain more individual round LEDs 1913 and still keep them within operating temperature; 12 watts of total power usage (4 round LEDs) is typical with such a mass of overmold 2461. When operated in air, the external surface temperature of overmold 2461 will generally stay below 50 C while the temperature of the LED surfaces (1918, 1919 of FIG. 19) will generally stay below 60 C which is suitable for long term operation.

Figure 25:
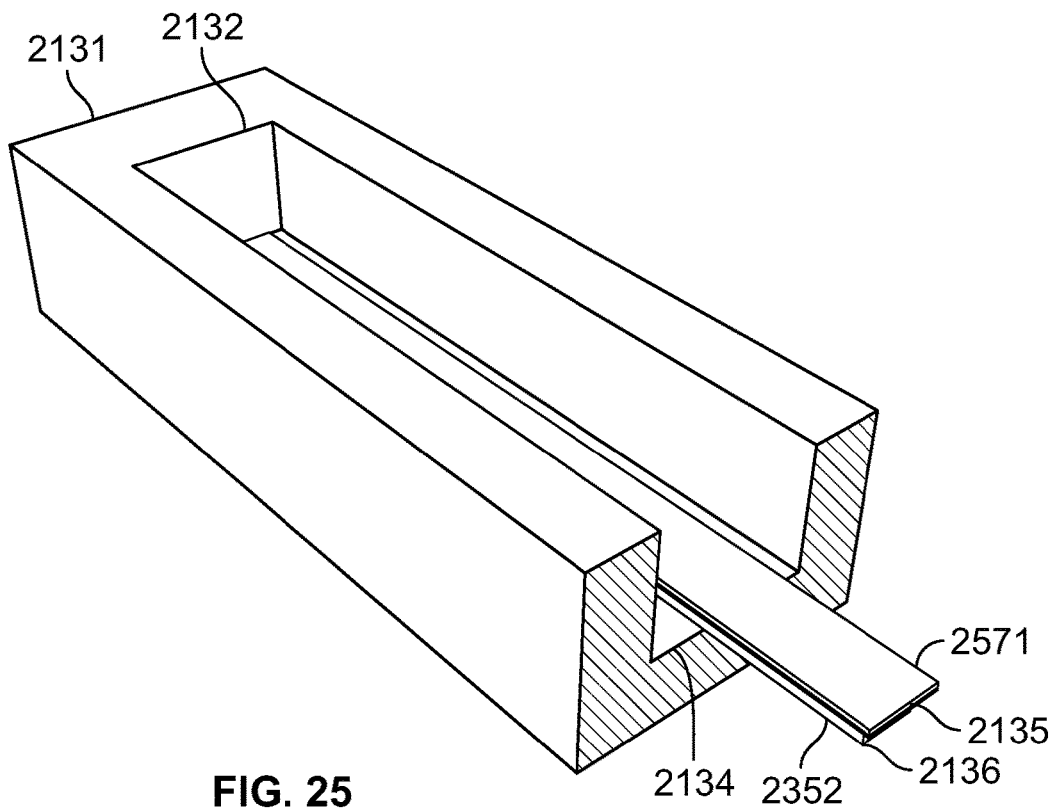
FIG. 25 shows a perspective sectioned view of components of another submersible illumination emitter embodiment before molding.

FIG. 25 shows an alternate positioning method for pre-mold structure 2571 shown here consisting only of LED 2135 and lens 2136, but facing downwards inside mold 2131. Front of mold 2131 is again sectioned off. Lens 2136 outer surface 2352 (facing downwards) is secured into position onto mold cavity 2132 floor 2134 such that when resin is poured into mold cavity 2132 the resin will substantially not flow beneath outer surface 2352; thus when demolded, outer surface 2352 will be substantially free of resin and will therefore allow illumination to travel from LED 2135 to ambient via the bottom of the resulting solidified overmold. Outer surface 2352 of lens 2136 could be held onto bottom wall 2134 by the weight of pre-mold structure 2571, or by added weight (not shown) on top of pre-mold structure 2571 which would subsequently be encapsulated within pre-mold structure 2571, or by a weak adhesive or mold release gel, or even by simple van der Waals forces that occur from pressing outer surface 2352 against a soft silicone bottom floor 2134 surface. Not only does the positioning technique of FIG. 25 eliminate all floats, braces and bond lines (except for lens 2136 and a power cable), but the resulting demolded illumination apparatus will have its lens 2136 outer surface 2352 in flush alignment with the exterior of the bottom of the overmold, thus allowing the resulting demolded apparatus lens outer surface 2352 to be held flat against transparent aquarium or sump walls without illumination escaping laterally.

Figure 26:
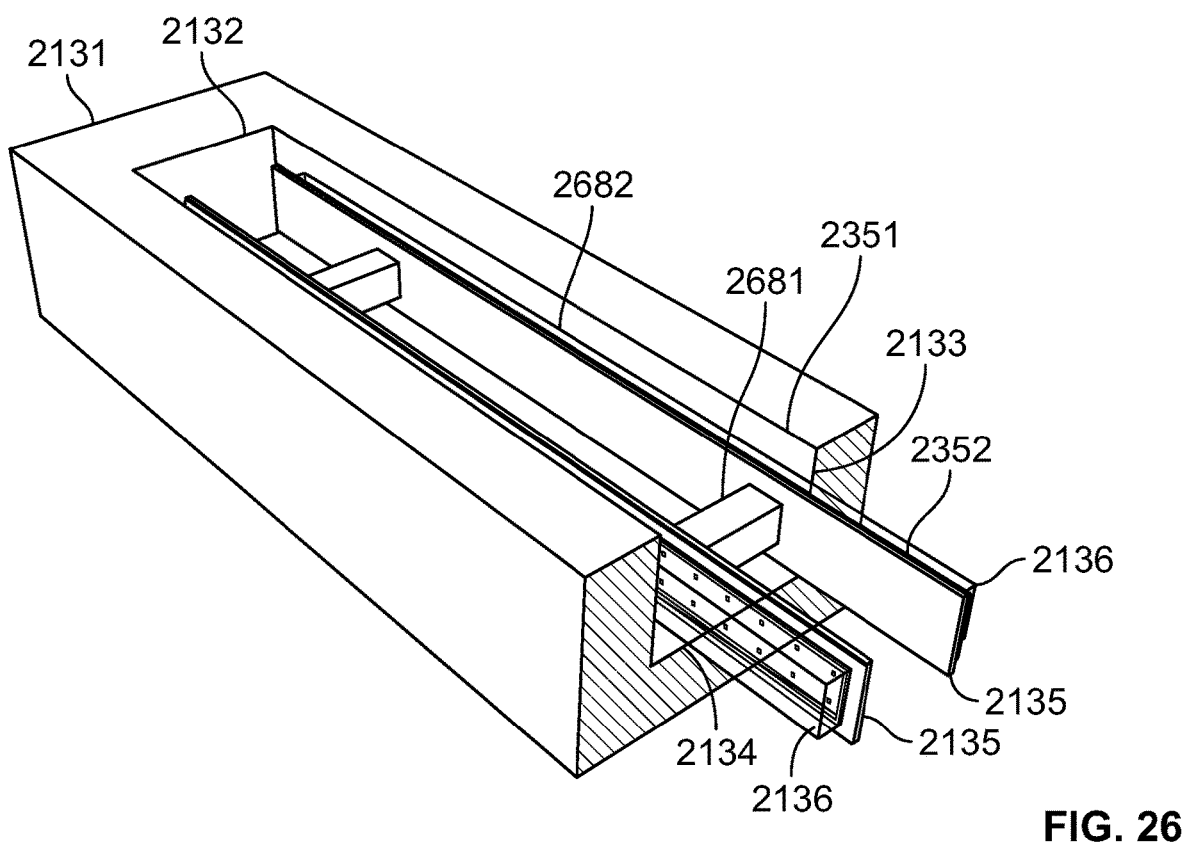
FIG. 26 shows a perspective sectioned view of components of another submersible illumination emitter embodiment before molding.

FIG. 26 shows another alternate positioning method for molding (again with front of mold 2131 sectioned off), this time for pre-mold structure 2682 shown here consisting of two each of LED 2135, lens 2136, brace 2681, and with the outer surface 2352 of each LED 2135 positioned facing apart, held against side walls 2133 of mold cavity 2132 by braces 2681. Similar to FIG. 25, lens 2136 outer surface 2352 is secured into position on mold cavity 2132 side walls 2133 such that when resin is poured into mold cavity 2132 the resin will substantially not flow onto outer surface 2352; thus when demolded, LED lens outer surfaces 2352 will be substantially free of resin and will therefore allow illumination to travel from both LED 2135 to ambient via the sides of the resulting overmold. And although braces 2681 will be encapsulated with the resulting overmold, they will not add any bond lines to the structure because they do not reach the external surfaces of the mold. Lastly, the pressure or adhesion of the outer surfaces 2352 into side walls 2133 allows pre-mold structure 2682 to remain above bottom floor 2134 without the need to set on floor 2134, and also to remain below fill level 2351; this positioning above floor 2134 and below fill level 2351 means that no part of pre-mold structure 2682 will be exposed to ambient once demolded, except lenses 2136 and a power cable.

Figure 27:
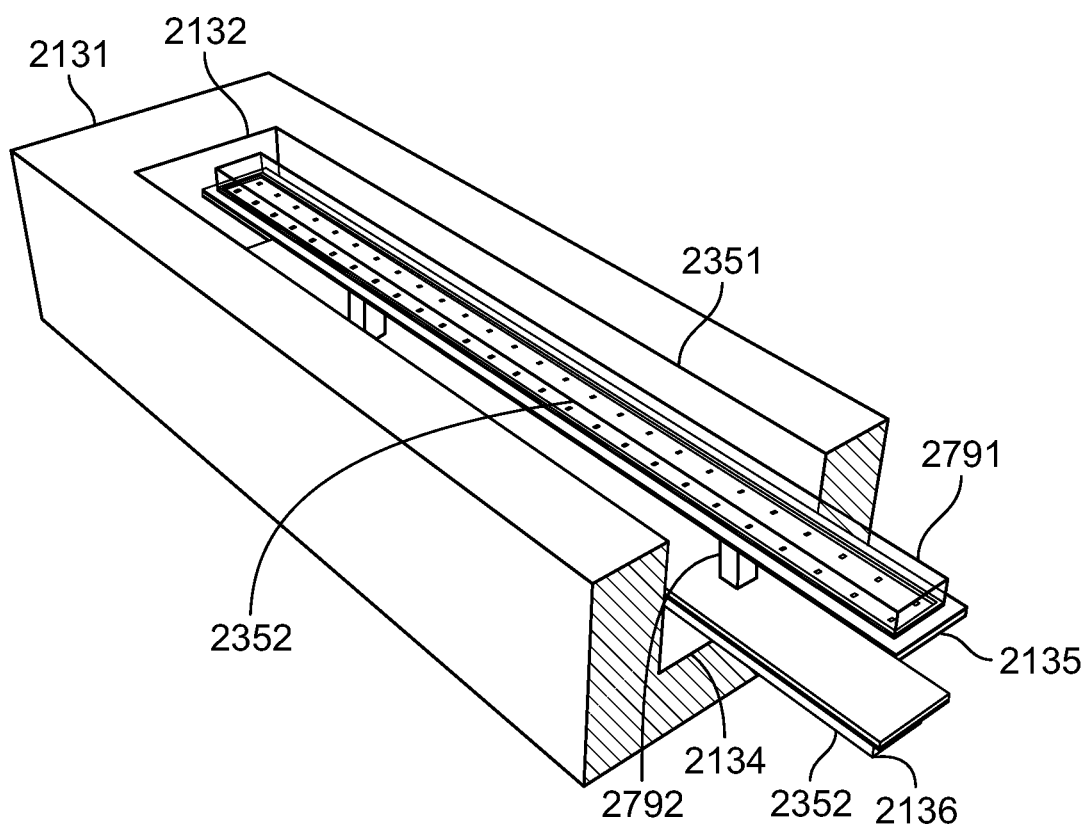
FIG. 27 shows a perspective sectioned view of components of yet another submersible illumination emitter embodiment before molding.

FIG. 27 shows another alternate positioning method for molding (again with front of mold 2131 sectioned off), this time with pre-mold structure 2791 which consists here of two each of LED 2135, lens 2136, and vertical brace 2792. Bottom facing lens outer surface 2352 is adhered to or removably attached or weighted to bottom floor 2134 as in FIG. 25, and vertical braces 2792 are sized to position upper facing lens outer surface 2352 slightly above fill level 2351 such that when resin is poured into mold cavity 2132 the bottom facing lens outer surface 2352 is substantially not covered by the resin, and the upper facing lens outer surface 2352 remains above fill level 2351 thus remaining resin-free. Demolding of the cured resin (not shown) will result in an overmold with illumination emitter 2135 lenses 2136 on top and bottom and will have been accomplished in a single resin layer step with no bond lines added other than the required bond lines for the lenses and power cable.

Examples Claims—Illumination Devices

1. A water submersible and ambient air cooled illumination apparatus, comprising:
   an illumination emitter;
   a lens;
   an overmold, the overmold being substantially thermally conductive, substantially electrically non-conductive, and substantially non-metallic, the overmold to position the lens to be in optical communication with the illumination emitter and to enable illumination and heat from the illumination emitter to travel to surrounding ambient air or water;
   whereas the illumination apparatus can operate without moisture damage when submerged in water and without heat damage in ambient air.
2. The illumination apparatus of claim 1, wherein a total bond line ratio is less than 0.1

3. The illumination apparatus of claim 1, wherein the overmold substantially contacts a bottom side and a top side of the illumination emitter.
4. The illumination apparatus of claim 1, wherein the overmold is a single layer.
5. The illumination apparatus of claim 4, wherein the overmold has an additional bond line from a brace, the additional bond line not exceeding a 0.002 bond line ratio.
6. The illumination apparatus of claim 1, wherein the overmold substantially contacts a top side of the illumination emitter.
7. The illumination apparatus of claim 6, wherein the overmold is a single layer.
8. The illumination apparatus of claim 7, wherein the overmold has an additional bond line from a brace, the additional bond line not exceeding a 0.002 bond line ratio.
9. The illumination apparatus of claim 1, further comprising a translucent coating which substantially coats both the lens and a top portion of the overmold.
10. The illumination apparatus of claim 9, wherein the coating is transparent.
11. The illumination apparatus of claim 10, wherein the overmold is a single layer.
12. The illumination apparatus of claim 11, wherein the overmold has an additional bond line from a brace, the additional bond line not exceeding a 0.002 bond line ratio
13. A method for making a water submersible and ambient air cooled illumination apparatus, comprising:
placing a pre-mold structure inside a mold cavity;
positioning the pre-mold structure such that an outer surface of an illumination emitter lens is positioned at least at an outer perimeter of the mold cavity;
placing within the mold cavity a liquid overmold material that is substantially thermally conductive, substantially electrically non-conductive, and substantially non-metallic, such that the outer surface of the lens is substantially not covered by the overmold material;
allowing the overmold material to solidify;
demolding the solidified overmold material;
whereas the resulting demolded illumination apparatus can operate in ambient air or submerged in water without moisture or heat damage to the emitter.
14. The method for making an illumination apparatus of claim 13, wherein the outer surface of the lens is above a fill level.
15. The method for making an illumination apparatus of claim 13, wherein the lens is held in position by a holding force.
16. The method for making an illumination apparatus of claim 15, wherein the holding force is van der Waals forces between a mold cavity wall and an outer surface of the illumination emitter lens.
17. The method for making an illumination apparatus of claim 15, wherein the holding force is an external holding device.
18. The method for making an illumination apparatus of claim 15, wherein the holding force is buoyancy.
19. The method for making an illumination apparatus of claim 15, wherein the holding force is magnetism.
20. The method for making an illumination apparatus of claim 15, wherein the holding force is an internal brace.
21. The method for making an illumination apparatus of claim 20, wherein the brace extends to a bottom floor of the mold cavity.
22. The method for making an illumination apparatus of claim 20, wherein the brace extends between at least two separate pre-mold structures.
23. The method for making an illumination apparatus of claim 13, comprising the additional steps of:
coating both the lens and the overmold with a liquid translucent coating.
allowing the liquid translucent coating to solidify.
24. The method for making an illumination apparatus of claim 23 wherein the coating is transparent.
25. The method for making an illumination apparatus of claim 13, wherein the pre-mold structure includes braces.
26. The method for making an illumination apparatus of claim 13, wherein the pre-mold structure includes floats.
27. The method for making an illumination apparatus of claim 13, wherein the pre-mold structure includes magnets.
28. A water submersible and ambient air cooled illumination apparatus substantially as hereinbefore described with reference to FIGS. 19-27.
29. A method for making a water submersible and ambient air cooled illumination apparatus substantially as hereinbefore described with reference to FIGS. 19-27.

3D Printed Macroalgal Attachment Material

The surfaces to which macroalgae attach preferably should be rough and porous so as to allow the algae to hold on without detachment during the rapid water and/or gas bubble flow that is required for enhanced growth. A porous surface allows the attachment points of the macroalgae to hold on better, especially if the orifices which make up the porous network allow the algal cells to circle around back to themselves so that they can form a loop, much like vines wrapping around a trellis will connect back to themselves. Previous work by the applicant in 2008 includes using plastic knitting canvas material roughed up by hand (detailed in applicant's U.S. Pat. No. 9,115,008), and ribbons and rocky textures in applicant's pending U.S. application Ser. No. 14/380,926, both of which are herein incorporated by reference in their entirety. While these previously described attachment surfaces do work well, their manufacture requires a fair amount of labor, such as the roughing of the canvas, or the gluing of the ribbons or rocks. Other available manufacturing techniques such as injection molding come at a high initial price yet are still not able to include extremely thin features which enhance algal attachment, especially "slime" algae attachment. The present invention makes use of current low cost 3D printing technology to solve these issues, and applicant's Green Grabber® algal attachment screens are examples of the results. Following are definitions specific to the present 3D printed macroalgal attachment material methods and apparatuses.

"Solid Polymer"—A polymer (28120, 29220, 29230) that is below it's melting temperature and thus does not flow, although it can still be elastic if mechanical pressure is applied to it. The solid polymer (28120, 29220, 29230) can be any shape, e.g. a non-porous smooth sheet 28130; a rough sheet 28120 in which water cannot penetrate; a regular pattern of cross members (28112, 28113) in which water can penetrate; or a random pattern of random shapes, or a regular pattern of repeated shapes. The shapes can be organic or geometric; planar or non-planar.

"Melted Polymer"—A polymer 29248 that is above it's melting temperature and thus flows with gravity. Melted polymer can be poured out of a cup. Melted polymer that has cooled enough to become solid 29247 is termed "solidified".

"Heating Element"—A solid object 29210, usually but not necessarily metal, which can be brought to a high enough temperature to melt a solid polymer (28120, 29220, 29230). This solid polymer could be the shape of a filament 29220 that comes into contact with heating element 29210. Solid polymer filament 29220 may enter an orifice in heating element 29210 and exit heating element 29210 in melted state 29248; this is an established and desired 3D printing methodology. Alternately, heating element 29210 can be made to come into contact with solid polymer 29250, causing solid polymer 29250 to become melted polymer 29257. This melted polymer 29257 will often adhere to heating element 29210, and while this does occur frequently, it is usually not desired in 3D printing methodologies because it tends to drag melted polymer 29257 into places where the user does not want it. A heating element 29210 that is not part of a 3D printer may also be used, e.g. a heated object 29210, possibly under computer motion control, which just touches, melts, and then moves melted polymer 29257; this could be thought of as "sculpting" the polymer.

Figure 29:
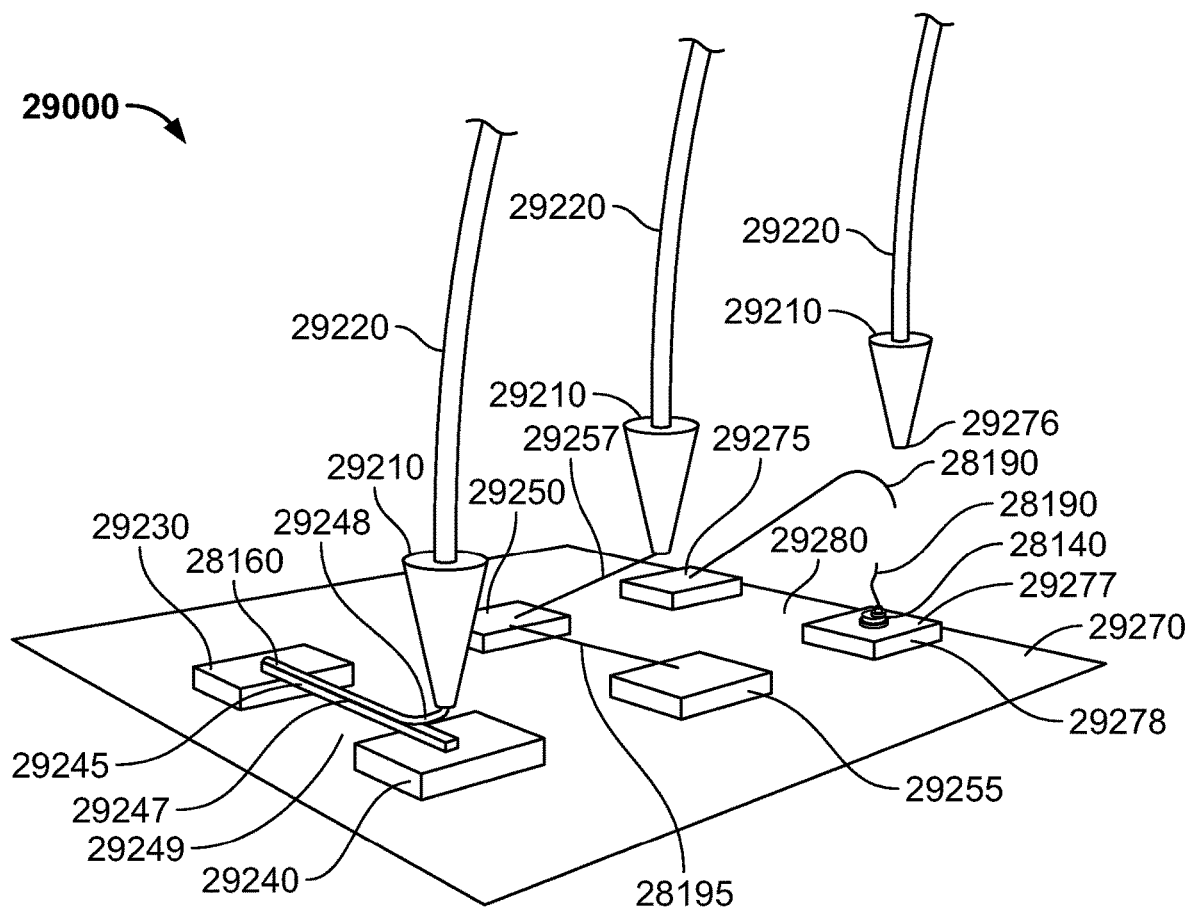
FIG. 29 shows a perspective drawing representing 3D printed methods for making macroalgal attachment materials of the current invention.

"Layer"—a single thickness of 3D printed solidified polymer 29245 that is attached to a surface 29230, the surface 29230 usually being below layer 29245 or at least below a section of layer 29245. Layer 29245 can be planar as shown in FIG. 29, as is the case in most current 3D melting-filament printers, or layer 29245 could be curved in one or more axes as can be done on "polar" or multi-axis "reticulated arm" melting-filament printers. A 3D printed object 28000 is usually built with many layers on top of each other; the first layer often being attached to a usually planar surface such as a metal or glass "bed" 29270 so as to secure the resulting solidified 3D printed object 28000 in a stationary position while heating element 29210 moves in relation to object 28000. A first layer might be a bottom layer 29245 as shown in FIG. 29000 which is not the bottom first layer of the entire object 28000, but instead is just the bottom first layer of the section where layer 29245 is placed. Additional layers 29247 can then be added to first layer 29245.

"Extrude"—The process of utilizing a melting-filament 3D printer and 3D printer heated nozzle 29210 to push solid polymer filament 29220 into the heated nozzle 29210 such that when the polymer exits nozzle 29210 the polymer 29248 is melted and the moving nozzle can therefore "print" or "lay-down" or "deposit" this melted polymer 29248 onto something below it. If the extruded polymer 29248 is deposited onto a planar surface such as glass or metal bed 29270, then polymer 29248 solidifies and attaches to bed 29270; if the extruded polymer 29248 is deposited onto a previously deposited layer 29245 of polymer, then polymer 29247 welds itself to the previous layer 29245. The resultant deposited and solidified polymer 29247 is an "extrusion", and this extrusion process is standard in the art. An extrusion 29245 can also done in mid-air if the extrusion 29245 is attached at both ends so as to keep it from falling.

"Hairline Thread"—a very thin cross-section of solidified polymer (28190, 28195), usually less than 0.5 mm in diameter, and sometimes less than 0.1 mm, that is only attached at one or both ends and is otherwise suspended in mid-air. A hairline thread (28190, 29195) can be made by the movement of heating element 29210 from a first location 29275 to a second location 29276 when there is melted polymer 29248 adhered to the outside of heating element 29210; the shape of the hairline thread (28190, 28195) may very well resemble a human hair. When hairline threads (28190, 28195) are made in 3D printing it is sometimes called "stringing", and this process does not require the 3D printing nozzle 29210 to be extruding at the time that the threads (28190, 28195) are being formed. Hairline threads (28190, 28195) are commonly thinner than the orifice diameter where melted filament 29248 exits nozzle 29210, and thus hairline threads (28190, 28195) cannot be easily extruded directly from such nozzles 29210 because the extruded polymer 29248 would be thicker than desired.

"Bridge"—a section (28160, 29245) of a 3D printed object 28000 which crosses a void (29249, 29280) much like a highway bridge crosses a river. The cross-section of solidified polymer bridge (28160, 29245) is thicker than a hairline thread (28190, 28195) and is usually greater than 0.5 mm in diameter and is usually several printed layers thick. A bridge (28160, 29245) is attached to sections of solid polymer (29230, 29240) on both ends of the bridge (28160, 29245), and the bridge (28160, 29245) may be of any cross-sectional shape such as round or square or organic (irregular).

"Cross Members"—Main structural sections (28112, 28113) of some types of macroalgal attachment material 28000, often resembling a screen. The area directly between cross members (28112, 28113) is open and herein is called a void. Cross members (28112, 28113) can be formed into the shape of a sheet 28110 resembling a porous screen so water and light can penetrate macroalgal attachment material 28000 thus enhancing photosynthesis. Alternately, cross members (28112, 28113) could be attached to a non-porous sheet 28130 such that water and light cannot penetrate; this is shown by label 28120 where porous screen 28110 is attached to non-porous sheet 28130. Many other shapes of cross members (28112, 28113) are possible besides a screen shape, such as amorphous rock shapes, tree shapes, man-made wall shapes, etc., so long as there is an open void directly between at least two of the cross members (28112, 28113).

"Void"—An open area between solidified polymer such as cross members (28112, 28113), the area having substantially no polymer except possibly for hairline threads 28195. Voids are generally 1-10 mm across, and preferably between 2-7 mm across.

"Polymer Sheet"—A general sheet of polymer 28120, with or without holes or voids, that is smooth planar 28170 or with shapes such as cross members (28112, 28113) or a combination of these. A polymer sheet 28120 can also be just a flat polymer screen 28110 as explained above.

"Lump"—A protruding irregularity 28140 on the surface of an otherwise planar or regular-patterned sheet of polymer (28110, 28120, 28130). Lumps 28140 are generally 1-5 mm in diameter, and extend generally 1-5 mm out from the sheet (28110, 28120, 28130). Lumps 28140 can be created either by the deposition of melted polymer 29248 from a 3D printing nozzle, or by the contact and subsequent moving away of a heating element 29210 with a solid polymer 29250, or a combination of both.

"Bed"—A flat surface 29270 that solidified polymer 29250 is adhered to in melting-filament 3D printing. The bed 29270 can cause a smooth (possibly planar) surface on the bottom 28180 of the printed part 28000, no matter what shape the rest of the printed part 28000 is. A glass bed 29270 especially, can give a mirror-smooth finish on the bottom 28180 of printed part 28000. Such smooth surfaces do not contribute to the ability of macroalgae to attach.

"Porous"—A material having the ability of gas bubbles to at least partially penetrate it without diverting around it, or water to at least partially pour through it without the flowing over the sides of it.

"Non Porous"—A material having the ability to prevent gas bubbles from penetrating it, or water from pouring through it.

Several types of 3D printing methodologies are available, but most are not at the low cost level needed for simple "algae attachment screens". And the almost universal desire of all 3D printer users is to create the finest detail, using the smallest layer 29245 heights, and with the least artifacts and errors as possible; this makes cost go up even further when fine detail is involved because the printers must run slower and more precise, or use polymer at a reduced rate in thinner layers 29245, thus taking longer to complete. Interestingly, these very artifacts which users wish to avoid can make a macroalgal attachment surface more effective, and as of December 2015 had not yet been implemented to make very rough macroalgal attachment materials.

In particular, melting-filament printing (called Fused Deposition Modeling (FDM) and Fused Filament Fabrication (FFF) printing) have a "flaw" which turns out to be a benefit for algal attachment: they can have "hairline threads" (28190, 28195, 29257). These hairline threads (28190, 28195, 29257) can occur when the print nozzle 29210 in a FDM/FFF melting-filament printer tries to move the heating element nozzle 29210 in a non-printing (non-extruding) move from a first location 29275 to a second location 29276, but during this move nozzle 29210 leaks melted polymer 29257 when it is not supposed to, or, melted polymer 29248 that is adhered onto the outside of printer nozzle 29210 drags across a previously printed surface. In other words, there are areas 29275 where the nozzle is supposed to print (extrude) melted polymer, and areas 29276 where it is not supposed to, but nozzle 29210 must still move past these non-printing areas 29276 to get to the next area 29277 that needs printing. It's during these non-printing moves (called "travels") that undesired hairline threading (28190, 28195, 29257) can occur, and if there are enough of these hairline threads, a 3D printed object can look like it is covered in spider webs.

One explanation for this undesired release of melted polymer (28190, 28195, 29257) is that 3D printing nozzles 29210 have a "melt zone" or "melt pool" inside them which is between the solid polymer filament 29220 (going into the nozzle 29210), and the output orifice (not shown) of nozzle 29210 at its bottom. After printing a first location 29250, nozzle 29210 stops pushing filament 29220 out and then moves to second location 29255 that needs printing; however during this move to second location 29255 the "melt pool" inside nozzle 29210 starts draining out of nozzle 29210, and thus lets out a little bit of melted filament 28195 during this move. So, in between first printed area 29250 and second printed area 29255, this little bit of melted filament causes a hairline thread 28195 to appear between the two areas. Hairline threads 28195 and hairline threading ("stringing") are normally avoided using many different techniques including:

1. Retracting melted polymer 29248 back into the nozzle 29210 during non-printing travel moves; 2. Reducing nozzle 29210 temperature; 3. Moving nozzle 29210 faster during non-printing travel moves; 4. Wiping nozzle 29210 before non-printing travel moves; 5. Allowing previously-printed layers 29245 to cool more before printing a next layer 29247 on top of it; 6. Reducing overall amounts of polymer 29220 being pushed through nozzle 29210; 7. Reducing bed 29270 temperature; 8. Using PLA polymer. 9. Not allowing nozzle 29210 to travel across previously printed areas; 10. Using a smaller orifice for nozzle 29210. So interestingly, if you do the opposite of some or all of these techniques, you can encourage hairline threads (28190, 28195, 29257) which will enable better macroalgal attachment because the more places algae can grab on to, the better the algae can grow longer without being washed away by air/water interface turbulence. These techniques are detailed below:

1. A very common technique to avoid hairline threading (28190, 28195, 29257) is to "retract" melted filament 29248 back into nozzle 29210, usually 1-3 mm for direct drive type filament printers, or 5-10 mm for Bowden type filament printers, before a non-printing travel move. Turning off this retraction can cause large amounts of hairline threads (28190, 28195, 29257) especially when the nozzle 29210 is moving across large areas of the printed object.

2. Polymers 29220 used in 3D printing such as ABS tend to start flowing and hairline threading (28190, 28195, 29257) more as the temperature of nozzle 29210 increases, so the usual goal is to reduce nozzle 29210 temperature enough that threading (28190, 28195, 29257) stops but the extrusion process continues. ABS polymer tends to start threading more at 240 C, so increasing the nozzle 29210 temperature above 240 C will generate more of the desired hairline threads (28190, 28195, 29257).

3. Non-printing moves, called "travels", are usually done much faster than printing, thus nozzle 29210 can get to the new printing location before melted polymer 29248 drains out of nozzle 29210. If nozzle 29210 is printing (moving) at 30 to 60 mm per second across bed 29270, then a non-printing "travel" move is usually more than 100 mm/s. So by not speeding up these non-printing travels, nozzle 29210 will slowly cross over printed areas, enabling melted polymer 29248 to flow out of nozzle 29210 thus cause hairline threads (28190, 28195, 29257). In particular, slowing the travel speed down to 30 mm per second is preferred; 20 mm per second is more preferred, and 10 mm per second is most preferred.

4. Wiping nozzle 29210 is a printing option that causes nozzle 29210 to remove excess melted polymer 29248 from the nozzle 29210 tip/orifice before traveling to the next printing location. It does this by making non-printing moves of nozzle 29210 across an already-printed layer 29230 while in contact with the layer 29230, which then scrapes melted filament 29248 off nozzle 29210. Thus, by turning off this "wiping" feature, more threading (28190, 28195, 29257) will occur.

5. Printed parts 28000 which are about 4 square cm (2 cm by 2 cm) or less cause heated nozzle 29210 to stay very near the same printing location 29230, going back and forth within the 4 square cm area and causing the printed solidified polymer 28160 in that location to stay hot because of the radiated and convected heat from the nearby nozzle 29210. Since the previously-printed layer 29245 in this case can thus still be somewhat melted when nozzle 29210 comes back to print the next layer 29247, previously-printed layer 29245 tends to stick to nozzle 29210 and get dragged around. The usual solution is to use a print-cooling fan (not shown) to blow air onto the just-printed section 29245, or to have nozzle 29210 move far away after each layer for a few seconds, for example about 5 cm, so previously-printed layer 29245 can cool (solidify) before nozzle 29210 comes back for the next layer 29247. Generally if nozzle 29210 can be moved 5 cm away from original part 2 cm by 2 cm part 28000, and stay away for at least 30 seconds, original part 28000 (and original layer 29245) will be solidified and ready for a next layer 29247. So by not allowing this cooling to take place (by not using a cooling fan, or by not moving the nozzle farther away), previously-printed layer 29245 on original part 28000 will still be somewhat melted and will adhere much more to nozzle 29210 and will thus create more threading (28190, 28195, 29257). When printing a large flat algae-attachment screen, this process can be done by computer modeling a screen 28000 in several separate 4 square cm pieces (2 cm by 2 cm squares) that are touching each other, and then instructing the printer to print each square completely (from first bottom layer to last top layer) before moving to the next 4 square cm piece. If external dimensions of nozzle 29210 are narrow enough, and if the adjoining squares are not too many layers tall, then nozzle 29210 will be able to move to the adjacent square and start printing its first bottom layer 29255 without hitting the top layers of the previous square. This is usually possible because macroalgal attachment materials are often less than 2 mm thick.

6. Allowing too much (called "over extruding") melted polymer 29248 to be pushed out of nozzle 29210, compared to the amount needed for proper printing, causes threading (28190, 28195, 29257) because the excess polymer "squeezes out sideways" from below nozzle 29210 and tends to stick to the outside of nozzle 29210 and get dragged around. So, by over extruding purposely, such as by using 10 to 50 percent more polymer 29220 than required for a "proper" print, threading (28190, 28195, 28257) can be obtained. The exact volumetric amounts of polymer flow vary by nozzle 29210 size and printing speed, but all melting-filament printers are calibrated for best polymer flow before printing, so after this calibration for a normal proper print, the extrusion rate can then be increased 10 to 50 percent above this extrusion rate.

7. Temperature of bed 29270 is usually set so extruded polymer has good adhesion of the first layer 29278 to bed 29270; on subsequent (upper) layers, bed 29270 temperature is sometimes reduced so as to not add extra unneeded heat to the remaining layers that are yet to print. Too much heat from bed 29270 can cause upper layers 29245 to stay melted longer, contributing to threading (28190, 28195, 29257). Commonly the first layer 29278 may print with bed temperatures of 100C to 110C for ABS plastic filament, and be reduced to 80 C or 90 C on subsequent layers. So by not reducing bed 29270 temperature, or instead increasing bed 29270 temperature beyond what is needed for good first-layer 29278 polymer adhesion to bed 29270, more heat will flow upwards. A bed 29270 heat of 130C for ABS plastic, especially if the entire printed object 28000 is a thin (e.g. 2-5 mm) screen laid flat on bed 29270, will greatly add to threading (28190, 28195, 29257).

8. Of the two common melting-filament polymers 29220 currently used in 3D printing, PLA and ABS, using PLA will easily print at lower temperatures and do so with little threading (28190, 28195, 29257). So by using ABS polymer filament 29220 instead, and at higher temperatures, more threading (28190, 28195, 29257) will occur. And a newer filament, PETG, is known to have even more threading (28190, 28195, 29257) even when precautions are taken. So by using PETG, threading (28190, 28195, 29257) will be maximized.

9. A printer option called "avoid crossing perimeters" or "combing" causes nozzle 29210 to not cross over outer walls of previously printed locations, and instead keeps nozzle 29210 inside of the outer walls of printed object 28000 so that any threading will disappear inside object 28000 and not be seen outside of final printed object 28000. So by turning this feature off, and also possibly computer modeling object 28000 such that many non-printing travel moves occur over previously printed areas, threading (28190, 28195, 29257) will be increased. One way to do this computer modeling is to have several different heights of model 28000, such that they are islands next to, but touching, one another. The height difference of the islands does not need to be great; only one printed layer's 29245 thickness, which is usually 0.1 to 0.3 mm. The height differences may be invisible to the user but nozzle 29210 will still have to make non-printing travel moves from one island to the next, thus maximizing threading (28190, 28195, 29257) as nozzle 29210 travels over previously printed locations.

10. Smaller nozzle 29210 orifices (not shown) such as 0.2 and 0.3 mm diameter will offer greater resistance to melted polymer 29248 draining out of nozzle 29210 during non-printing travel moves. So by using larger nozzle 29210 orifices such at 0.4 and 0.5 mm, and especially 0.6 mm diameter, draining will be increased especially on long travel moves. These larger nozzle 29210 orifice diameters will also allow more melted polymer 29248 to be extruded during printing, thus further increasing the amount of polymer that adheres to the outside of the nozzle 29210 which subsequently gets dragged around.

Now is described how to stretch melted polymer 29248 with a heating element so as to form hairline threads (28190, 28195, 29257). The heating element can be a 3D printer nozzle 29210, or another heated object 29210 that does not extrude, but the stretching of polymer will still occur because of the adhesion of melted polymer 29248 to the outside of heating element 29210. The direction of hairline threads (28190, 28195, 29257), and contact or non-contact of hairline threads (28190, 28195, 29257) with each other, can be controlled by the direction of travel of the heating element 29210 when stretching the melted polymer 29248. By having heating element 29210 move in the same direction each time when stretching polymer 29248, subsequently solidified hairline threads (28190, 28195, 29257) will substantially be in the same direction. And by pausing movement of heating element 29210 during the stretch, melted polymer 29248 that is farther from heating element 29210 is allowed to solidify in a stretched and upwards location 29276 thus reducing the chance of the melted hairline thread 28190 falling down and solidifying onto another hairline thread 28195. The pause of movement can be from 0.5-5 seconds if no print-cooling fan is used; a print-cooling fan (not shown) will reduce the pause time needed. The advantage of having all hairline threads 28190 substantially in the same direction and non-touching is it allows "comb harvesting", which is the ability to harvest algae from hairline threads with one motion of a comb-harvesting device without the "comb" getting stuck in and/or damaging hairline threads 28190. This comb-harvesting is described in detail in co-pending U.S. application Ser. No. 14/380,926 which is herein incorporated by reference in its entirety.

Some applications of algal attachment material 28000 focus on dark slime macroalgal growth, or brown slime growth such at dinoflagellates or diatoms. This type of growth does not attach as well to surfaces the way green hair algae does, and thus needs more "holding" or support from attachment material 28000. U.S. Pat. No. 8,764,985 by Adey details these supporting mechanisms, and is herein incorporated by reference in its entirety. In these cases of more slime-based algae, the preferred mechanical structure of attachment material 28000 is more of a web of hairline threads (28190, 28195, 29257) that are touching/connected, and thus the preferred direction of hairline threads is non-uniform (e.g., random), especially if the threads 28195 re-attach at their ends, thus forming a supporting "web" for the algae. To make this web of touching/connected hairline threads 28195, heating element 29210 need only direct it's movement back and forth over previously solidified hairline threads 28195.

A furthering of the hairline thread concept is "bridging". Although thicker than hairline threads (28190, 28195, 29257), bridges (28160, 29245) still allow macroalgae to encircle the bridge (28160, 29245) and attach back to itself. Although bridging is an established and desired technique in 3D printing, it is usually for larger parts of a printed object where the bridge is several centimeters high or long, for example the top of a door in a house model. In contrast, for algal attachment, what is preferred is a large number of very small bridges (28160, 29245) with sizes of the order of 1-5 mm span, with 1-2 mm high passage 29249 below it, such that the passage 29249 created under the bridge (28160, 29245) has a cross sectional area (span times height) less than 10 square mm, and preferably less than 5 square mm. These bridges (28160, 29245) allow algae to stay inside the passage 29249 under the bridge (28160, 29245), and not be removed when the algae is harvested by the user, thus shortening the re-growth time of the next growth cycle because there will still be algae there for growth. The algae stay attached because the small passages 29249 are too narrow to allow cleaning brushes or scrapers to get inside, thus the algae are not brushed away during harvesting. A high concentration of these bridges (28160, 29245) per square centimeter allows maximum algal attachment: At least 2 bridges (28160, 29245) per square cm is desired; more desired is 4 bridges per square cm, and most desired is 8 bridges per square cm. Note that bridges can also be irregular organic shapes, instead of the straight or curved shapes of 28160 as shown.

Another type of stretched melted polymer is a lump. Lumps 28140 are very durable compared to hairline threads (28190, 28195, 29257) and will resist damage when macroalgae is harvested from macroalgal attachment material 28000, especially if a mechanical scraper is used such as a rubber scraping tool or stiff brush. Some macroalgae may also be so well-attached to hairline threads (28190, 28195, 29257) that the threads break off when the algae is harvested. Lumps 28140, however, are by comparison short and thick, and should resist breakage from most types of macroalgae attachment and harvesting. And the combination of hairline threads (28190, 28195, 29257) and lumps 28140 provides attachment surfaces for both slime algae (dinoflagellates, diatoms, etc) and the sturdier hair macroalgae (cladophora, ulva, spirogyra, etc) on one attachment material 28000. Note that lumps can also be irregular organic shapes, instead of the cylindrical shape 28140 shown.

When nozzle 29210 or heating element 29210 contacts solid polymer (28120, 29278) or deposits melted polymer 29248 onto solid polymer (28120, 29278, 29245), for example at a first position 29277, melted polymer 29248 adheres to both the solid polymer (28120, 29278) and the nozzle/heating element 29210. When nozzle/heating element 29210 is subsequently moved to a second position 29276, a "lump" 28140 will remain on solid polymer (28120, 29278). A hairline string 28190 may also be formed on top of lump 28140. The lump 28140 is generally larger than the contact area where nozzle/heating element 29210 touches the solid polymer (28120, 29278), especially if nozzle 29210 is extruding melted polymer 29248. Further, by pausing the movement of the nozzle/heating element 29210 a few millimeters above lump 28140 as the nozzle/heating element 29210 moves away from lump 28140, the thickness and height of lump 28140 can be altered. This pause may be from 0.5-5 seconds, and may occur from 1-10 mm from the lump, before the nozzle/heating element 29210 then proceeds to the second position 29276.

One last ability of a purposely "rough-printed" object 28000, such as applicant's Rough 3D™ technique, is the ability to include grommets 28197 within the rough textures during the printing of printed part 28000; the grommets 28197 can be used to attach finished object 28000 to water delivery pipes (if a waterfall algae scrubber configuration), spargers (if gas bubble upflow algae scrubber configuration), or other frames (if horizontal river/floway algae scrubber configurations). Not only does this allow grommet 28197 to be covered in the same rough textures as the remainder of object 28000, but grommet 28197 is stronger because it is becomes welded to the screen material during the 3D printing process which also increases production speed because a separate process is not needed to attach grommet 28197 to object 28000. Although called a grommet 28197, it can be any shape which allows anchors (not shown) to pass through the object 28000, and grommet 28197 should be printed thick enough to not rip away from the anchor when the growth surfaces are at their thickest growth. And although shown as circular, grommets 28197 could as well be square or other shapes, and can be positioned in the middle, front or back of material 28000.

Example Claims—3D Printed Macroalgal Attachment Material

1. A method for making macroalgal attachment material, comprising:
   (i) elevating the temperature of a heating element above the melting temperature of a solid polymer;
   (ii) moving the heating element to a first location, the first location enabling the heating element to be in mechanical contact with the solid polymer for a sufficient amount of time to melt the solid polymer such that resulting melted polymer adheres to the heating element;
   (iii) moving the heating element to a second location, the second location not in mechanical contact with the solid polymer of the first location, and the second location being far enough from the first location such that melted polymer that is adhered to the heating element is stretched into a lump;
   (iv) repeating steps (i) through (iii) in different locations until a desired number of lumps have been produced;
   whereby the lumps provide attachment points for freshwater and saltwater macroalgae.
2. The method for making macroalgal attachment material of claim 1, wherein motion of the heating element is paused during its travel from the first location to the second location such that the resulting shape of the lump is altered.

3. The method for making macroalgal attachment material of claim 2, wherein the heating element is paused 0.5-5 seconds at a distance of 1-10 mm from the first location.
4 The method for making macroalgal attachment material of claim 2, wherein the heating element moves away from the lump in such a way as to leave a hairline thread extending from the lump.
5. The method for making macroalgal attachment material of claim 4, wherein the hairline threads are directed to be in a substantially uniform direction and are substantially non-touching.
6. The method for making macroalgal attachment material of claim 4, wherein the hairline threads are directed to be in a substantially non-uniform direction and are substantially attached to one another.
7. The method for making macroalgal attachment material of claim 1, wherein the method uses a melting-filament 3D printer.
8. The method for making macroalgal attachment material of claim 1, wherein the polymer is PETG.
9. The method for making macroalgal attachment material of claim 1, wherein the heated bed temperature is more than 130 C.
10. The method for making macroalgal attachment material of claim 1, wherein steps (i) through (iv) result in lumps on a solid polymer sheet, the solid polymer sheet having a planar bottom surface.
11. The method for making macroalgal attachment material of claim 10, further comprising:
    (vi) performing steps (i) through (iv) again such that a second planar sheet of solid polymer with lumps is formed, the second solid polymer sheet also having a planar bottom surface;
    (vii) adhering the bottom planar surface of the first sheet of solid polymer to the bottom planar surface of the second sheet of polymer such as to form a single thicker sheet of solid polymer with lumps on both sides.
12. A macroalgal attachment material, comprising:
    a first sheet of polymer, the first sheet of polymer having a top surface and a bottom surface;
    a plurality of lumps positioned on the top surface of the first sheet of polymer, whereby the lumps of polymer provide attachment points for freshwater and saltwater macroalgae.
13. The macroalgal attachment material of claim 12, wherein the lumps extend 1-5 mm from the top surface of the sheet of polymer.
14. The macroalgal attachment material of claim 12, wherein the lumps are 1-5 mm in diameter.
15. The macroalgal attachment material of claim 12, wherein a plurality of lumps have a hairline thread extending from the lump.
16. The macroalgal attachment material of claim 15, wherein the hairline threads are in a substantially uniform direction and are substantially non-touching.
17. The macroalgal attachment material of claim 15, wherein hairline threads are in a substantially non-uniform direction and are substantially attached to each other.
18. The macroalgal attachment material of claim 12, wherein the polymer is PETG.
19. The macroalgal attachment material of claim 12, further comprising:
    a second sheet of solid polymer, the second sheet of solid polymer having a top surface and a planar bottom surface;
    a plurality of lumps positioned on the top surface of the second sheet of polymer, an attachment mechanism, the attachment mechanism to attach the planar bottom surface of the first sheet of solid polymer to the planar bottom surface of the second sheet of solid polymer.
20. The macroalgal attachment material of claim 12, wherein the sheet of solid polymer includes one or more grommets as a single unified component with the polymer sheet.
21. A method for making macroalgal attachment material, comprising:
    (i) elevating the temperature of a heating element above the melting temperature of a solid polymer;
    (ii) moving the heating element to a first location on the solid polymer, the first location enabling the heating element to be in mechanical contact with the solid polymer for a sufficient amount of time to melt the solid polymer such that the resulting melted polymer adheres to the heating element;
    (iii) moving the heating element to a second location of solid polymer such that melted polymer that is adhered to the heating element is stretched from the first location to the second location, the melted polymer then having a first end and a second end, and also such that the path of the stretched melted polymer crosses a void.
    (iv) placing the heating element in mechanical contact with solid polymer at the second location for sufficient time to weld the second end of melted polymer to the solid polymer at the second location;
    (v) removing the heating element from the second location of solid polymer so as to enable the stretched melted polymer to solidify into a hairline thread;
    (vi) repeating steps (i) through (v) until a desired number of hairline threads have been created.
22. The method for making macroalgal attachment material of claim 21, wherein the resulting stretched and solidified polymer is a hairline thread less than 0.5 mm in diameter.
23. The method for making macroalgal attachment material of claim 21, wherein the hairline threads are attached to a polymer sheet with a non-porous backing.
24. The method for making macroalgal attachment material of claim 21, wherein the hairline threads are attached to a polymer sheet that is porous.
25. The method for making macroalgal attachment material of claim 21, wherein the polymer is PETG.
26. The method for making macroalgal attachment material of claim 21, wherein the process uses a melting-filament 3D printer.
27. The method for making macroalgal attachment material of claim 21, wherein steps (i) through (iv) result in a first solid polymer sheet and attached hairline threads, the first solid polymer sheet having a planar bottom surface;
28. The method for making macroalgal attachment material of claim 27, further comprising the steps of:
    (vii) performing steps (i) through (vi) again such that a second sheet of solid polymer with hairline threads is formed, the second solid polymer sheet also having a planar bottom surface;

(viii) adhering the bottom planar surface of the first sheet of solid polymer to the bottom planar surface of the second sheet of solid polymer such as to form a single thicker sheet of solid polymer with hairline threads on both sides.

29. The method for making macroalgal attachment material of claim 21, wherein the sheet of solid polymer is non-porous.

30. The method for making macroalgal attachment material of claim 21, wherein the sheet of solid polymer is porous.

31. A macroalgal attachment material, comprising:
    a first sheet of solid polymer, the top surface of the first sheet of solid polymer having shapes which form voids;
    a plurality of hairline threads, each hairline thread crossing a void and connecting to solid polymer on each end of the hairline thread;
    whereby the hairline threads provide surfaces for freshwater and saltwater macroalgae to attach.

32. The macroalgal attachment material of claim 31, wherein the polymer is PETG.

33. The macroalgal attachment material of claim 31, wherein the first sheet of solid polymer sheet has a planar bottom surface.

34. The macroalgal attachment material of claim 31, wherein the first sheet of solid polymer sheet is non-porous.

35. The macroalgal attachment material of claim 31, wherein the first sheet of solid polymer sheet is porous.

36. The macroalgal attachment material of claim 31, wherein the first sheet of solid polymer defines cross members.

37. The macroalgal attachment material of claim 36, wherein the cross members are at right angles to one another.

38. The macroalgal attachment material of claim 33, further comprising:
    a second sheet of solid polymer, the bottom surface of the second sheet of solid polymer having a planar surface, and the top surface of the second sheet of solid polymer having shapes which form voids;
    a plurality of hairline threads, each hairline thread crossing a void and connecting to solid polymer on each end of the hairline thread;
    an attachment means, the attachment means to attach the bottom planar surface of the first sheet of polymer to the bottom planar surface of the second sheet of polymer such as to form a single thicker sheet of polymer with connected hairline threads on both sides;
    whereby the hairline threads provide attachment points for freshwater and saltwater macroalgae.

39. The macroalgal attachment material of claim 31, wherein the sheet of solid polymer includes one or more grommets.

40. A method for making macroalgal attachment material, comprising:
    (i) utilizing a melting-filament 3D printer nozzle to extrude a first extrusion of melted polymer such that the first extrusion welds to a first location on a solid polymer;
    (ii) extruding the nozzle at a second location on the solid polymer such that the melted polymer welds to the second location of solid polymer, and also such that a pathway from the first location to the second location crosses a void, thereby extruding a bridge;
    (iii) moving the nozzle away from the second location such that the extruded bridge solidifies;
    (iv) extruding at least a second extrusion on top of the first extrusion, the second extrusion to weld to and thicken the first extrusion;
    (v) repeating steps (i) through (iv) a plurality of times at different locations on the solid polymer until the desired number of bridges have been constructed;
    whereby the resulting polymer bridges provide surfaces for freshwater and saltwater macroalgae to wrap around.

41. The method for making macroalgal attachment material of claim 40, wherein the cross section of the resulting passage under each bridge is less than 10 square mm.

42. The method for making macroalgal attachment material of claim 40, wherein the polymer is PETG.

43. The method for making macroalgal attachment material of claim 40, wherein the resulting plurality of solidified polymer bridges defines a first sheet, the first sheet having a top surface and a planar bottom surface, the top surface containing the bridges.

44. The method for making macroalgal attachment material of claim 43, further comprising:
    (vi) repeating steps (i) through (v) so as to form a second sheet of solidified polymer, the second sheet having a top surface and a planar bottom surface, the top surface containing the polymer bridges;
    (vii) adhering the planar bottom surface of the first sheet of polymer to the planar bottom surface of the second sheet of polymer such as to form a single thicker sheet of polymer that has polymer bridges on both sides.
    whereby the resulting polymer bridges provide surfaces for freshwater and saltwater macroalgae to wrap around.

45. The method for making macroalgal attachment material of claim 44, wherein the resulting thicker sheet of solid polymer is non-porous.

46. The method for making macroalgal attachment material of claim 44, wherein the resulting thicker sheet of solid polymer is porous.

47. A macroalgal attachment material, comprising:
    a first sheet of solid polymer; the first sheet of solid polymer having a top surface and a planar bottom surface;
    a plurality of polymer bridges welded to the top surface;
    whereby the bridges provide attachment surfaces for freshwater and saltwater macroalgae to wrap around.

48. The macroalgal attachment material of claim 47, wherein cross sectional area of the passage under each bridge is less than 10 square mm.

49. The macroalgal attachment material of claim 47, wherein a concentration of polymer bridges is at least 2 per square cm.

50. The macroalgal attachment material of claim 47, wherein the first sheet of solid polymer is porous.

51. The macroalgal attachment material of claim 47, wherein the first sheet of solid polymer is non-porous.

52. The macroalgal attachment material of claim 47, wherein the polymer is PETG.

53. The macroalgal attachment material of claim 47, further comprising a second sheet of solid polymer; the second sheet of solid polymer having a top surface and a planar bottom surface;

a plurality of polymer bridges welded to the top surface of the second sheet of solid polymer;
an attachment means, the attachment means to attach the planar bottom surface of the first sheet of solid polymer to the planar bottom surface of the second sheet of solid polymer such that the resulting thicker sheet of solid polymer has polymer bridges on both sides;
whereby the polymer bridges provide attachment surfaces for freshwater and saltwater macroalgae to wrap around.

53. The macroalgal attachment material of claim 47, wherein the macroalgal attachment material includes one or more grommets.

54. A method for instructing a melting-filament 3D printer to print macroalgal attachment material, comprising using three or more of the following techniques:
No filament retraction is used;
Nozzle temperature is higher than 240 C;
Polymer is PETG;
Non-printing travel moves are less than 30 mm per second;
Nozzle wiping is not used;
Printing is done in sequential 2×2 cm squares, where each 2×2 cm square is completed from first bottom layer to last top layer before the next 2×2 cm square is started;
Extrusion is set to be over-extruded by at least 20 percent;
Heated bed temperature is higher than 130 C;
Non-printing travel moves are allowed to cross already-printed areas;
Nozzle orifice diameter is 0.5 mm or larger;
Whereby the resulting solidified polymer material will provide attachment surfaces for freshwater and saltwater macroalgae.

Figure 28:
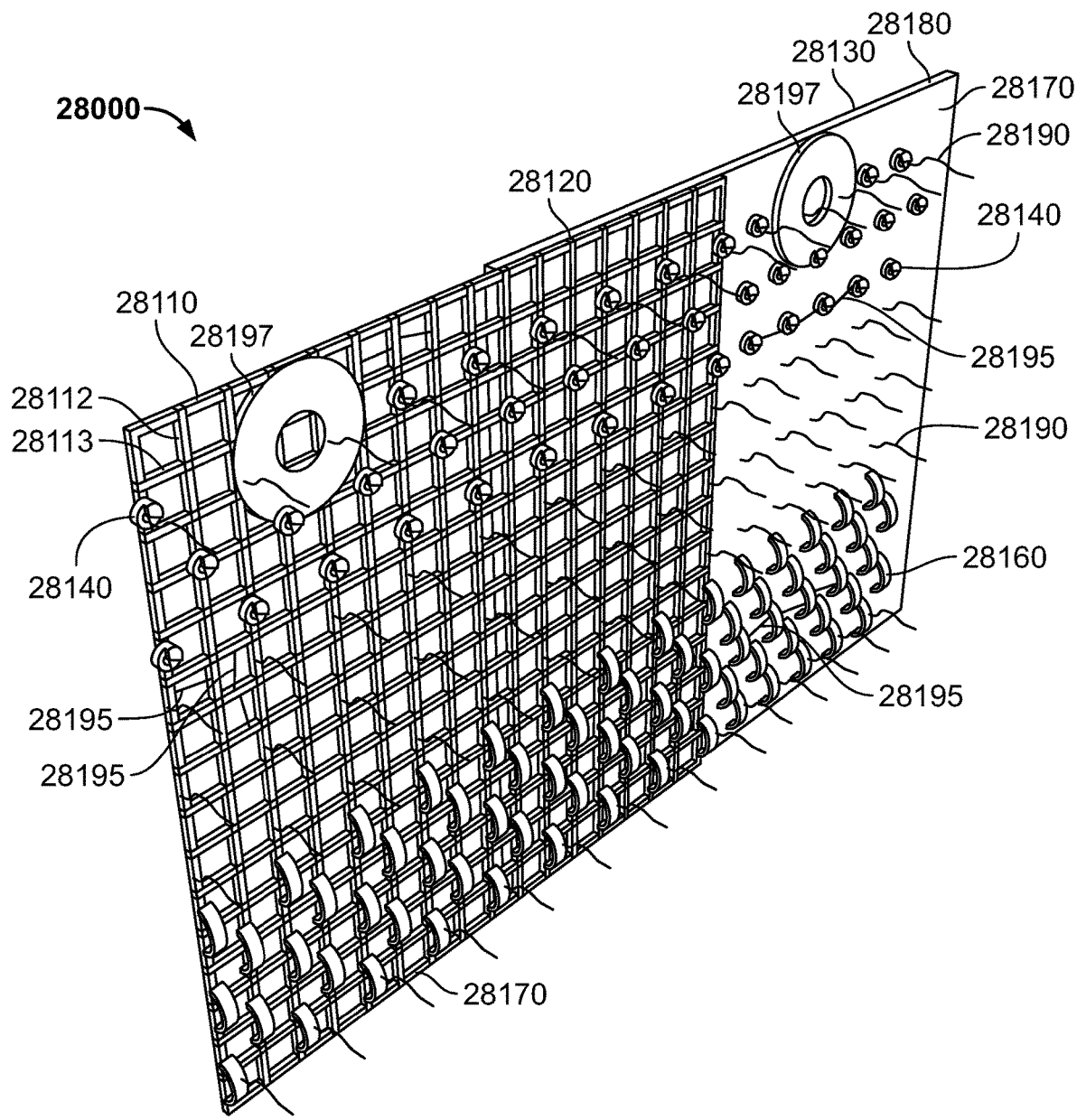
FIG. 28 shows a perspective view of 3D printed macroalgal attachment material that is an embodiment of the current invention.

55. A macroalgal attachment material substantially as hereinbefore described with reference to FIGS. 28-29.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting. Further, referenced patents and applications are incorporated herein by reference in their entirety. Where a definition or use of a term in a reference, which is incorporated by reference herein is inconsistent or contrary to the definition of that term provided herein, the definition of that term provided herein applies and the definition of that term in the reference does not apply. Nothing herein is to be construed as an admission that the present invention is not entitled to antedate such references by virtue of prior invention.

The invention claimed is:

1. Reservoir drain structure for waterfall algae scrubbers, comprising:
a waterfall algae scrubber water reservoir structure;
a waterfall algae scrubber water reservoir compartment movable from a first position which contacts the reservoir structure, to a second position, and which defines a water inlet and a reservoir compartment floor (1740), the reservoir compartment floor defining a water outlet (920);
a macroalgal attachment material suspended from the reservoir compartment floor and substantially below the water outlet;
wherein water travels from the water inlet, across the water reservoir compartment floor, through the water outlet to the macroalgal attachment material when the reservoir compartment is in the first position.

2. The reservoir drain structure of claim 1, wherein the reservoir compartment further defines at least one sidewall (1730).

3. The reservoir drain structure of claim 2, wherein the at least one sidewall is at least 3 cm above the reservoir compartment floor;
thereby enabling water to be deeper within the reservoir compartment thus providing a more uniform amount of water flow across the length of the water outlet.

4. The reservoir drain structure of claim 1, wherein the reservoir compartment in the first position is supported by the reservoir structure.

5. The reservoir drain structure of claim 1, wherein the reservoir compartment in the second position does not contact the reservoir structure;
thereby enabling greater access to the macroalgal attachment material for cleaning and harvesting.

6. The reservoir drain structure of claim 1, wherein the water inlet is located on a side of the reservoir compartment;
thereby enabling water to enter from a side location to spread laterally across the reservoir compartment.

7. The reservoir drain structure of claim 1, wherein the reservoir compartment in the first position is disposed entirely within the reservoir structure;
thereby enabling containment of the reservoir compartment inside of aquarium filtration compartments.

8. The reservoir drain structure of claim 1, wherein all sides of the reservoir compartment define a sidewall (1730);
thereby directing all water within the reservoir compartment to go down through the water outlet without escaping the reservoir compartment laterally.

9. The reservoir drain structure of claim 1, wherein an upper portion of the macroalgal attachment material is disposed within the water outlet;
thereby enabling the macroalgal attachment material to be secured from above the water outlet.

10. Reservoir drain structure for waterfall algae scrubbers, comprising:
a waterfall algae scrubber water reservoir structure defining a water inlet, a water outlet (920), and at least one sidewall (1730);
a macroalgal attachment material suspended from the water reservoir structure and substantially below the water outlet;
at least one growth containment wall (1810) contacting the water reservoir structure;
wherein water travels from the water inlet, through the water outlet, to the macroalgal attachment material.

11. The reservoir drain structure of claim 10, wherein the height of the at least one sidewall is at least 3 cm;
thereby enabling water to be deeper within the reservoir structure thus providing a more uniform amount of water flow across the length of the water outlet.

12. The reservoir drain structure of claim 10, further comprising a lateral removal slot;
wherein the macroalgal attachment material can be removed laterally (1465) without requiring a user to reach into the reservoir structure.

13. The reservoir drain structure of claim 10, wherein the water inlet is a top opening (1410) of the reservoir structure.

14. The reservoir drain structure of claim 10, wherein the water inlet defines a pole mount coupler (420);

thereby enabling the reservoir structure to be supported by a pole mount (410) connected to the pole mount coupler.

15. The reservoir drain structure of claim 10, wherein the at least one growth containment wall encircles the macroalgal attachment material;

thereby preventing algal growth or water from escaping laterally.

16. Reservoir drain structure for waterfall algae scrubbers, comprising:

a waterfall algae scrubber water reservoir structure defining a water inlet, at least one water reservoir structure sidewall (1730), and a water outlet border (1520);

a water outlet structure movable from a first position which contacts the water reservoir structure to a second position, and which defines a water outlet (920);

a macroalgal attachment material suspended from the water outlet structure and substantially below the water outlet;

whereby in the first position water travels from the water inlet to the water outlet structure, through the water outlet, to the macroalgal attachment material.

17. The reservoir drain structure of claim 16, wherein the height of the at least one sidewall is at least 3 cm high;

thereby enabling water to be deeper within the reservoir structure thus providing a more uniform amount of water flow across the length of the water outlet.

18. The reservoir drain structure of claim 16, wherein the water inlet is located on a side of the reservoir structure;

thereby enabling water to enter from a side location to spread laterally across the water outlet structure.

19. The reservoir drain structure of claim 16, wherein the water inlet is a top opening (1410) of the reservoir structure;

thereby enabling water to enter the reservoir structure from an aquarium compartment overflow (1770).

20. The reservoir drain structure of claim 16, wherein all sides of the reservoir structure define a reservoir structure sidewall (1730);

thereby directing all water within the reservoir structure to go down through the water outlet without escaping the reservoir structure laterally.

\* \* \* \* \*